(12) United States Patent
Liu et al.

(10) Patent No.: US 12,221,448 B2
(45) Date of Patent: Feb. 11, 2025

(54) SELECTIVE PI3Kδ INHIBITOR AND USE THEREOF

(71) Applicant: TARAPEUTICS SCIENCE INC., Bengbu (CN)

(72) Inventors: Qingsong Liu, Anhui (CN); Jing Liu, Anhui (CN); Xiaofei Liang, Anhui (CN); Feng Li, Anhui (CN); Ziping Qi, Anhui (CN); Zongru Jiang, Anhui (CN); Qingwang Liu, Anhui (CN); Kailin Yu, Anhui (CN); Zhenquan Hu, Anhui (CN); Beilei Wang, Anhui (CN); Li Wang, Anhui (CN)

(73) Assignee: TARAPEUTICS SCIENCE INC., Bengbu (CN)

( * ) Notice: Subject to any disclaimer, the term of this patent is extended or adjusted under 35 U.S.C. 154(b) by 867 days.

(21) Appl. No.: 17/299,498

(22) PCT Filed: Dec. 12, 2018

(86) PCT No.: PCT/CN2018/120685
§ 371 (c)(1),
(2) Date: Jun. 3, 2021

(87) PCT Pub. No.: WO2020/113642
PCT Pub. Date: Jun. 11, 2020

(65) Prior Publication Data
US 2022/0024931 A1    Jan. 27, 2022

(30) Foreign Application Priority Data

Dec. 4, 2018  (CN) .......................... 201811471591.5

(51) Int. Cl.
*C07D 487/04* (2006.01)
*A61P 19/02* (2006.01)

(52) U.S. Cl.
CPC ............ *C07D 487/04* (2013.01); *A61P 19/02* (2018.01)

(58) Field of Classification Search
CPC .......... A61P 11/00; A61P 19/02; A61P 35/00; A61P 35/02; A61P 37/00; A61P 37/08; C07D 487/04
See application file for complete search history.

(56) References Cited

U.S. PATENT DOCUMENTS 8,703,777 B2 *  4/2014  Ren ........................ A61K 45/06
                                                         514/263.22

FOREIGN PATENT DOCUMENTS

| CN | 1440408   A | 9/2003 |
|----|-------------|--------|
| CN | 101965335 A | 2/2011 |
| CN | 105431437 A | 3/2016 |
| JP | 2003-531209 A | 10/2003 |
| JP | 2011-509259 A | 3/2011 |
| JP | 2016-523892 A | 8/2016 |
| WO | 2017/187324 A1 | 11/2017 |

OTHER PUBLICATIONS

Non-Hodgkin Lymphoma Causes, Risk Factors, and Prevention. American Cancer Society. Feb. 15, 2024. p. 1-12 (Year: 2024).*
Chinese Office Action dated Dec. 9, 2022 received in Chinese Application No. 201811471591.5, 11 pages.
Li, F., et al., "Discovery of (S)-2-(1-(4-Amino-3-(3-fluoro-4-methoxyphenyl)-1 H-pyrazolo[3,4-d]pyrimidin-1-yl)propyl)-3-cyclopropyl-5-fluoroquinazolin-4(3 H)-one (IHMT-PI3Kδ-372) as a Potent and Selective PI3Kδ Inhibitor for the Treatment of Chronic Obstructive Pulmonary Disease", Journal of Medicinal Chemistry 2020, Published Nov. 12, 2020, pp. 13973-13993, vol. 63.
International Search Report dated Sep. 11, 2019 issued in PCT/CN2018/120685.
Ma, Chenchen et al. "Discovery of Novel Quinazolinone Derivatives as High Potent and Selective PI3Kdelta and PI3Kdelta/y Inhibitors", European Journal of Medicinal Chemistry (Mar. 23, 2018, No. 151, pp. 9-17.

(Continued)

*Primary Examiner* — Noble E Jarrell
*Assistant Examiner* — Richard Grant Peckham
(74) *Attorney, Agent, or Firm* — Scully, Scott, Murphy & Presser, P.C.

(57) ABSTRACT

The present application relates to a compound serving as a selective PI3Kδ kinase inhibitor, comprising the compound shown in formula (I) or a pharmaceutically acceptable salt, solvate, ester, acid, metabolite or prodrug thereof, wherein X, $R_1$, $R_2$, $R_3$, $R_4$, $R_5$ and $R_6$ are as defined in the description. The present application also relates to a method for using the kinase inhibitor to inhibit PI3Kδ kinase activity or to treat or prevent diseases or conditions associated with tyrosine kinase activity of PI3Kδ, as well as a use thereof.

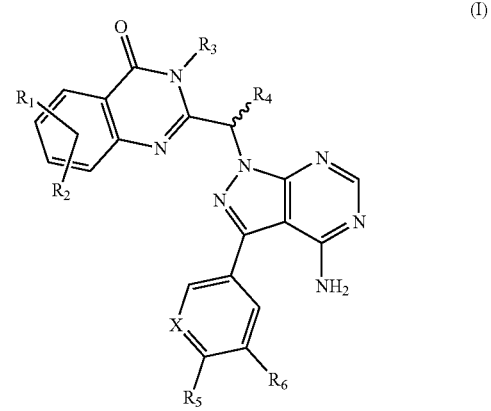

13 Claims, 1 Drawing Sheet

(56) References Cited

OTHER PUBLICATIONS

Vivanco et al., "The Phosphatidylinositol 3-Kinase-AKT Pathway in Human Cancer" Nature Reviews—Cancer (Jul. 2002), vol. 2, issue 7, pp. 489-501.

Al-Alwan, Monther M. et al., "Requirement for Phosphoinositide 3-Kinase p110delta Signaling in B Cell Antigen Receptor-Mediated Antigen Presentation", Journal of Immunology (2007), 178, pp. 2328-2335.

Bilancio, Antonio et al., "Key role of the p110delta isoform of PI3K in B-cell antigen and IL-4 receptor signaling: comparative analysis of genetic and pharmacologic interference with p110delta function in B cells", Blood (Jan. 15, 2006), vol. 107, issue 2, pp. 642-650.

Newcomb, Dawn C. et al., "Phosphatidylinositol 3-Kinase Is Required for Rhinovirus-induced Airway Epithelial Cell Interleukin-8 Expression", The Journal of Biological Chemistry (2005), vol. 280, issue 44, pp. 36952-36961.

Knight Z.A. et al., "A Pharmacological Map of the PI3-K Family Defines a Role for p110a in Insulin Signaling", Cell 125(4):733-747 (May 19, 2006).

European Extended Search Report dated Jul. 25, 2022 received in European Application No. 18 942 216.5.

\* cited by examiner

SELECTIVE PI3Kδ INHIBITOR AND USE THEREOF

TECHNICAL FIELD

This application relates to a compound serving as a selective PI3Kδ kinase inhibitor, and a method and use for using such a compound to inhibit PI3Kδ kinase activity.

BACKGROUND OF THE INVENTION

Phosphatidylinositol 3-kinase (PI3K) is a member of the lipid kinase family and an important part of the PI3K/AKT/mTOR signaling pathway. It can mediate the phosphorylation process within the body, thereby affecting a series of processes such as cell growth, proliferation, differentiation, migration and apoptosis. Studies have found that abnormal activation of the PI3K pathway is closely related to occurrence and progression of a variety of diseases, and different types of PI3Ks play different functions. PI3K family type I kinases mainly include PI3Kα, PI3Kβ, PI3Kγ and PI3Kδ. Among them, PI3Kα mutations are related to occurrence and progression of tumors; PI3Kβ can activate platelets and is related to progression of thrombotic diseases, and in PTEN-deficient tumors, PI3Kβ may promote tumor malignancy; PI3Kγ and PI3Kδ are mainly related to the immune system and hematopoietic system, and are closely related to occurrence of immunogenesis, hematological tumors and inflammation. PI3Kδ is a subtype of PI3K, and is mainly found in white blood cells. In recent years, PI3Kδ has been selected as a target to develop selective PI3Kδ inhibitors, which can treat lymphomas and hematological tumors related to B cells. Studies have shown that inhibition of PI3Kδ is effective in the treatment of hematological tumors, and thus PI3Kδ kinase has become a target for the treatment of hematological tumors, such as chronic lymphocytic leukemia (CLL), non-Hodgkin's lymphoma (NHL), Hodgkin's lymphoma (HL), mantle cell lymphoma (MCL), etc. In addition, PI3Kδ is a very critical protein in the development of B cells, and blocking the function of PI3Kδ can affect the function of B cells (Vivanco and Sawyers, Nature Reviews Cancer, 2002, vol. 2, issue 7, 489-501). Recent studies have shown that PI3Kδ mutations are related to induced respiratory infections and injuries, and studies have confirmed that inhibition of PI3Kδ is effective in the treatment of experimental arthritis, suggesting that PI3Kδ may be a target for the treatment of autoimmune diseases. Therefore, inhibition of PI3Kδ will play a role in the treatment of autoimmune diseases related to rheumatoid arthritis (RA), systemic lupus erythematosus (SLE) and asthma, etc. (J. Immunol., 2007, 178, 2328-2335; Blood, 2006, vol. 107, issue 2, 642-650). PI3K inhibitors are expected to provide therapeutic benefits via their role in regulating T-cell-mediated inflammatory responses associated with respiratory diseases such as asthma, COPD, and cystic fibrosis (J. Biol. Chem., 2005, vol. 280, issue 44, 36952).

Through experiments, the inventor found a selective PI3Kδ kinase inhibitor, as well as a method and use for using the kinase inhibitor to inhibit PI3Kδ kinase activity.

SUMMARY OF THE INVENTION

The invention provides a selective PI3Kδ kinase inhibitor.
More specifically, the invention provides a selective PI3Kδ kinase inhibitor, comprising a compound of formula (I) or a pharmaceutically acceptable salt, solvate, ester, acid, metabolite or prodrug thereof:

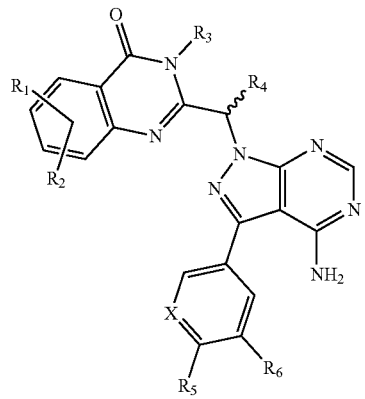

wherein,
X is selected from the group consisting of CH and N;
$R_1$ and $R_2$ are each independently selected from the group consisting of hydrogen, halogen, and $C_{1-6}$ haloalkyl;
$R_3$ is $C_{3-8}$ cycloalkyl;
$R_4$ is selected from the group consisting of hydrogen and $C_{1-6}$ alkyl;
$R_5$ is selected from the group consisting of hydrogen, $C_{1-6}$ alkyl, $C_{1-6}$ alkoxy, $C_{2-6}$ alkylamido, and $C_{1-6}$ alkylaminoacyl;
$R_6$ is selected from the group consisting of hydrogen, hydroxy, halogen, $C_{1-6}$ alkyl, and $C_{1-6}$ alkoxy;
or $R_5$ and $R_6$ together form a phenyl group or a dioxolane group.

In a preferred embodiment, X is CH.
Preferably, $R_1$ and $R_2$ are each independently selected from the group consisting of hydrogen, fluorine, and methyl.
Further preferably, $R_3$ is selected from the group consisting of cyclopropyl, cyclobutyl, cyclopentyl, and cyclohexyl.
Still preferably, $R_4$ is selected from the group consisting of hydrogen, methyl, and ethyl.
Further preferably, $R_5$ is selected from the group consisting of hydrogen, $C_{1-3}$ alkyl, $C_{1-3}$ alkoxy, $C_{2-3}$ alkylamido, and $C_{1-3}$ alkylaminoacyl; particularly preferably, $R_5$ is methoxy.
Still preferably, $R_6$ is selected from the group consisting of hydrogen, hydroxy, halogen, $C_{1-3}$ alkyl, and $C_{1-3}$ alkoxy; particularly preferably, $R_6$ is selected from the group consisting of hydrogen, fluorine, and methoxy.

The invention also relates to a pharmaceutical composition comprising the above compound or a pharmaceutically acceptable salt, solvate, ester, acid, metabolite or prodrug thereof, and a method and use for using the compound or pharmaceutical composition to inhibit PI3Kδ kinase activity, and a method and use for the treatment, prevention or amelioration of diseases, disorders or conditions which are regulated by or affected by PI3Kδ kinase activity or in which PI3Kδ kinase activity is involved.

DETAILED DESCRIPTION OF THE INVENTION

Terminology

Figure 1A:
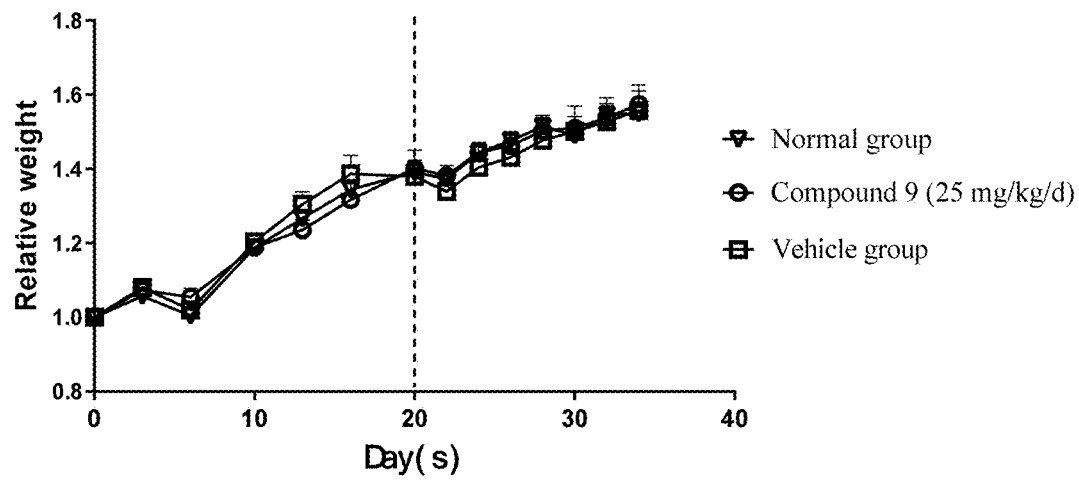
FIG. 1a shows the effect of Compound 9 of the invention, vehicle, and physiological saline on body weight of rats after administration.

Unless defined otherwise, all technical and scientific terms used herein have the same meaning as is commonly understood by one of skill in the art to which the claimed subject matter belongs.

Unless otherwise indicated, conventional methods of mass spectroscopy, NMR, HPLC, protein chemistry, biochemistry, recombinant DNA techniques and pharmacology, within the skill of the art are employed in the invention. Unless specific definitions are provided, the nomenclature employed in connection with, and the laboratory procedures and techniques of, analytical chemistry, synthetic organic chemistry, and medicinal and pharmaceutical chemistry described herein are those known in the art. The foregoing techniques and procedures can be generally performed of conventional methods well known in the art and as described in various general and more specific references that are cited and discussed throughout the present specification.

The term "alkyl" refers to an aliphatic hydrocarbon group, which may have branched or straight chain. Depending on the structure, an alkyl group can be a monoradical or a diradical (i.e., an alkylene group). In the invention, the alkyl group is preferably an alkyl having 1 to 8 carbon atoms, and more preferably a "lower alkyl" having 1 to 6 carbon atoms, and even more preferably an alkyl having 1 to 4 carbon atoms. Typical alkyl groups include, but are not limited to, methyl, ethyl, propyl, butyl, pentyl, hexyl, and the like. It should be understood that the "alkyl" mentioned herein includes all possible configurations and conformations of the alkyl group. For example, the "propyl" mentioned herein includes n-propyl and isopropyl, "butyl" includes n-butyl, isobutyl, and tert-butyl, "pentyl" includes n-pentyl, isopentyl, neopentyl, tert-pentyl, and pent-3-yl.

The term "alkoxy" refers to an —O-alkyl group, where the alkyl is as defined herein. Typical alkoxy groups include, but are not limited to, methoxy, ethoxy, propoxy, butoxy, pentyloxy, hexyloxy, and the like.

The term "alkoxyalkyl" refers to an alkyl radical, as defined herein, substituted with an alkoxy group, as defined herein.

The term "cycloalkyl" refers to a monocyclic or polycyclic radical that contains only carbon and hydrogen. Cycloalkyl groups include groups having from 3 to 12 ring atoms. Depending on the structure, a cycloalkyl group can be a monoradical or a diradical (e.g., an cycloalkylene group). In the invention, the cycloalkyl group is preferably a cycloalkyl having 3 to 8 carbon atoms, and more preferably a "lower cycloalkyl" having 3 to 6 carbon atoms. Examples of cycloalkyl groups include, but are not limited to, cyclopropyl, cyclobutyl, cyclopentyl, cyclohexyl, cycloheptyl, cyclooctyl, cyclopentenyl, cyclohexenyl, cycloheptenyl, and adamantyl.

The term "alkyl(cycloalkyl)" or "cycloalkylalkyl" refers to an alkyl radical, as defined herein, substituted with a cycloalkyl group, as defined herein. Non-limiting cycloalkylalkyl groups include cyclopropylmethyl, cyclobutylmethyl, cyclopentylmethyl, cyclohexylmethyl, and the like.

The term "aromatic" refers to a planar ring having a delocalized 7l-electron system containing $4n+2$ $\pi$ electrons, where n is an integer. Aromatic rings can be formed from five, six, seven, eight, nine, or more than nine atoms. Aromatics can be optionally substituted. The term "aromatic" includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

As used herein, the term "aryl" refers to an aromatic ring wherein each of the atoms forming the ring is a carbon atom. Aryl rings can be formed from five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

The term "aryloxy" refers to an —O-aryl group, where the aryl is as defined herein.

The term "heteroaryl" refers to an aryl group that includes one or more ring heteroatoms selected from the group consisting of nitrogen, oxygen and sulfur. An N-containing "heteroaryl" moiety refers to an aromatic group in which at least one of the skeletal atoms of the ring is a nitrogen atom. Depending on the structure, the heteroaryl group may be a monoradical or a diradical (i.e., a heteroarylene group). Examples of heteroaryl groups include, but are not limited to pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, indazolyl, indolizinyl, phthalazinyl, pyridazinyl, isoindolyl, pteridinyl, purinyl, oxadiazolyl, thiadiazolyl, furyl, benzofuranyl, benzothiophenyl, benzothiazolyl, benzoxazolyl, quinazolinyl, naphthyridinyl, furopyridinyl, and the like.

The term "alkyl(aryl)" or "aralkyl" refers to an alkyl radical, as defined herein, substituted with an aryl group, as defined herein. Non-limiting alkyl(aryl) groups include benzyl, phenethyl, and the like.

The term "alkyl(heteroaryl)" or "heteroarylalkyl" refers to an alkyl radical, as defined herein, substituted with a heteroaryl group, as defined herein.

As used herein, the term "heteroalkyl" refers to an alkyl group, as defined herein, in which one or more skeletal chain atoms is a heteroatom, e.g., oxygen, nitrogen, sulfur, silicon, phosphorus or combinations thereof. The heteroatom(s) may be placed at any interior position of the heteroalkyl group or at the position at which the heteroalkyl group is attached to the remainder of the molecule.

As used herein, the term "heterocycloalkyl" or "heterocyclyl" refers to a non-aromatic ring wherein one or more atoms forming the ring is a heteroatom selected from the group consisting of nitrogen, oxygen and sulfur. Heterocycloalkyl rings can be formed by three, four, five, six, seven, eight, nine, or more than nine atoms. Heterocycloalkyl rings can be optionally substituted. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, imidazolidine, pyrrolidone, pyrazoline, pyrazolidine, imidazoline, imidazolidine, 1,3-diox ole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Depending on the structure, a heterocycloalkyl group can be a monoradical or a diradical (i.e., a heterocycloalkylene group).

The term "alkyl(heterocycloalkyl)" or "heterocycloalkylalkyl" refers to an alkyl radical, as defined herein, substituted with a heterocycloalkyl group, as defined herein.

The term "alkoxy(heterocycloalkyl)" or "heterocycloalkylalkoxy" refers to an alkoxy radical, as defined herein, substituted with a heterocycloalkyl group, as defined herein.

The term "halo" or "halogen" refers to fluoro, chloro, bromo and iodo.

The terms "haloalkyl", "haloalkoxy" and "haloheteroalkyl" include alkyl, alkoxy or heteroalkyl structures in which at least one hydrogen is replaced with a halogen atom. In certain embodiments in which two or more hydrogen atoms are replaced with halogen atoms, the halogen atoms are the same or different as one another.

The term "hydroxy" refers to an —OH group.

The term "cyano" refers to a —CN group.

The term "ester group" refers to a chemical moiety having the formula —COOR, where R is selected from the group consisting of alkyl, cycloalkyl, aryl, heteroaryl (connected through a ring carbon atom), and heterocyclyl (connected through a ring carbon atom).

The term "amino" refers to an —$NH_2$ group.

The term "aminoacyl" refers to a —CO—$NH_2$ group.

The term "alkylaminoacyl" refers to a —CO—NH—R group, where R is an alkyl group as defined herein.

The term "amide" or "amido" refers to —NR—CO—R', wherein R and R' are independently hydrogen or alkyl.

The term "alkylamino" refers to an amino substituent which is further substituted with one or two alkyl groups, specifically refers to the group —NRR', wherein R and R' are each independently selected from the group consisting of hydrogen or lower alkyl, with the proviso that —NRR' is not —$NH_2$. "Alkylamino" includes groups of compounds in which the nitrogen atom of —$NH_2$ is attached to at least one alkyl group. Examples of alkylamino groups include, but are not limited to, methylamino, ethylamino, and the like. "Dialkylamino" includes groups in which the nitrogen atom of —$NH_2$ is attached to at least two other alkyl groups. Examples of dialkylamino groups include, but are not limited to, dimethylamino, diethylamino, and the like.

The terms "arylamino" and "diarylamino" refer to amino substituents further substituted with one or two aryl groups, specifically refer to an —NRR' group, wherein R and R' are each independently selected from the group consisting of hydrogen, lower alkyl, or aryl, where N is connected to at least one or two aryl groups.

The term "cycloalkylamino" refers to an amino substituent further substituted with one or two cycloalkyl groups as defined herein.

The term "heteroalkylamino" refers to an amino substituent further substituted with one or two heteroalkyl groups as defined herein.

The term "aralkylamino" herein refers to an —NRR' group in which R is a lower aralkyl group and R' is hydrogen, lower alkyl, aryl, or lower aralkyl.

The term "heteroarylamino" refers to an amino substituent further substituted with one or two heteroaryl groups as defined herein.

The term "heterocycloalkylamino" refers to an amino radical, as defined to herein, substituted with a heterocycloalkyl group, as defined herein.

The term "alkylaminoalkyl" refers to an alkyl radical, as defined herein, substituted with an alkylamino group, as defined herein.

The term "aminoalkyl" refers to an alkyl substituent further substituted with one or more amino groups.

The term "aminoalkoxy" refers to an alkoxy substituent further substituted with one or more amino groups.

The term "hydroxyalkyl" or "hydroxylalkyl" refers to an alkyl substituent further substituted with one or more hydroxy groups.

The term "cyanoalkyl" refers to an alkyl substituent further substituted with one or more cyano groups.

The term "acyl" refers to a monovalent atomic radical remaining after removal of the hydroxyl group from an organic or inorganic oxyacid, represented by a general formula of R-M(O)—, wherein M is usually C.

The term "carbonyl" is an organic functional group (C=O) formed by carbon atom and oxygen atom through a double bond linkage.

The term "alkanoyl" or "alkylcarbonyl" refers to a carbonyl radical further substituted with an alkyl group. Typical alkanoyl groups include, but are not limited to, acetyl, propionyl, butyryl, valeryl, hexanoyl and the like.

The term "arylcarbonyl" refers to a carbonyl radical, as defined herein, substituted with an aryl group, as defined herein.

The term "alkoxycarbonyl" refers to a carbonyl radical further substituted with an alkoxy group.

The term "heterocycloalkylcarbonyl" refers to a carbonyl radical further substituted with a heterocycloalkyl group.

The terms "alkylaminocarbonyl", "cycloalkylaminocarbonyl", "arylaminocarbonyl", "aralkylaminocarbonyl", and "heteroarylaminocarbonyl" refer to a carbonyl radical, as defined herein, substituted with an alkylamino, cycloalkylamino, arylamino, aralkylamino, or heteroarylamino group, as defined herein, respectively.

The term "alkylcarbonylalkyl" or "alkanoylalkyl" refers to an alkyl radical further substituted with an alkylcarbonyl group.

The term "alkylcarbonylalkoxy" or "alkanoylalkoxy" refers to an alkoxy radical further substituted with an alkylcarbonyl group.

The term "heterocycloalkylcarbonylalkyl" refers to an alkyl radical further substituted with a heterocycloalkylcarbonyl group.

The term "mercapto" refers to an —SH group. The term "alkylthio" refers to a mercapto radical, as defined herein, substituted with an alkyl group as defined herein.

The term "sulfuryl" or "sulfonyl" refers to a functional group remaining after loss of hydroxyl groups from sulfonic acid, and specifically refers to a —$S(=O)_2$— group.

The term "sulfoxide" or "sulfinyl" refers to —S(=O)—.

The term "aminosulfuryl" or "aminosulfonyl" refers to a —$S(=O)_2$—$NH_2$ group.

The term "alkylsulfoxide" or "alkylsulfinyl" refers to alkyl —S(=O)—.

The term "alkylsulfuryl" or "alkylsulfonyl" refers to —$S(=O)_2$—R, where R is an alkyl group.

The term "alkylaminosulfuryl" refers to a sulfuryl radical, as defined herein, substituted with an alkylamino group, as defined herein.

The term "alkylsulfurylamino" or "cycloalkylsulfurylamino" refers to an amino radical, as defined herein, substituted with an alkylsulfuryl group or a cycloalkylsulfuryl group, as defined herein.

The terms "cycloalkylsulfuryl" and "cycloalkylsulfonyl" refer to —$S(=O)_2$—R, where R is a cycloalkyl group.

The terms "alkylsulfonamido" and "cycloalkylsulfonamido" refer to —NH—$S(=O)_2$—R, where R is an alkyl group and a cycloalkyl group, respectively.

The term "quaternary ammonium group" refers to —N⁺RR'R", wherein R, R' and R" are each independently selected from the group consisting of alkyl groups having 1-8 carbon atoms.

The term "optionally" means that one or more events described hereinafter may or may not occur, and include both the event(s) that may occur and the event(s) that may not occur. The term "optionally substituted" or "substituted" refers to that the mentioned group may be substituted with one or more additional groups which are each independently selected from the group consisting of alkyl, cycloalkyl, aryl, heteroaryl, heterocyclyl, hydroxy, alkoxy, cyano, halo, amide, nitro, haloalkyl, amino, methylsulfonyl, alkylcarbonyl, alkoxy carbonyl, heteroarylalkyl, heterocycloalkylalkyl, aminoacyl, amino protecting group, etc., wherein, the amino protecting group is preferably selected from the group consisting of pivaloyl, tert-butoxycarbonyl, benzyloxycarbonyl, 9-fluorenylmethoxycarbonyl, benzyl, p-methoxybenzyl, allyloxycarbonyl, trifluoroacetyl, and the like.

The term "tyrosine protein kinase (TPK)" as used herein is a type of kinase that catalyzes the transfer of γ-phosphate from ATP to tyrosine residues of a protein, catalyzes phosphorylation of tyrosine residues of various substrate proteins, and plays an important role in cell growth, proliferation, and differentiation.

The term "inhibit", "inhibitory", or "inhibitor" of a kinase, as used herein, refers to inhibition of phosphotransferase activity.

A "metabolite" of a compound disclosed herein is a derivative of that compound that is formed when the compound is metabolized. The term "active metabolite" refers to a biologically active derivative of a compound that is formed when the compound is metabolized. The term "metabolized" as used herein, refers to the sum of the processes (including, but not limited to, hydrolysis reactions and reactions catalyzed by enzymes, such as, oxidation reactions) by which a particular substance is changed by an organism. Thus, enzymes may cause specific structural alterations. For example, cytochrome P450 catalyzes a variety of oxidation and reduction reactions while uridine diphosphate glucuronyl transferases catalyze the transfer of an activated glucuronic acid molecule to aromatic alcohol, aliphatic alcohol, carboxylic acid, amine and free sulfhydryl group. Further information on metabolism may be obtained from *The Pharmacological Basis of Therapeutics,* 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidation processes and correspond to the corresponding hydroxy-containing compound. In some embodiments, a compound is metabolized to pharmacologically active metabolites. The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "target protein" refers to a protein molecule or a portion of a protein capable of being bound by a selective binding compound. In certain embodiments, the target protein is tyrosine kinase PI3Kδ (including the wild type or various mutations or combinations thereof).

As used herein, GI₅₀ refers to a drug concentration required for 50% growth inhibition of cells, i.e., a drug concentration at which the growth of 50% cells (such as cancer cells) can be inhibited or controlled by the drug.

As used herein, IC₅₀ refers to an amount, concentration or dosage of a particular test compound that achieves a 50% inhibition of a maximal response, in an assay that measures such response.

As used herein, EC₅₀ refers to a dosage, concentration or amount of a test compound that elicits a dose-dependent response at 50% of maximal expression of a particular response that is induced, provoked or potentiated by the particular test compound.

Kinase Inhibitor of the Invention

The invention provides a selective PI3Kδ kinase inhibitor, comprising a compound of formula (I) or a pharmaceutically acceptable salt, solvate, ester, acid, metabolite or prodrug thereof:

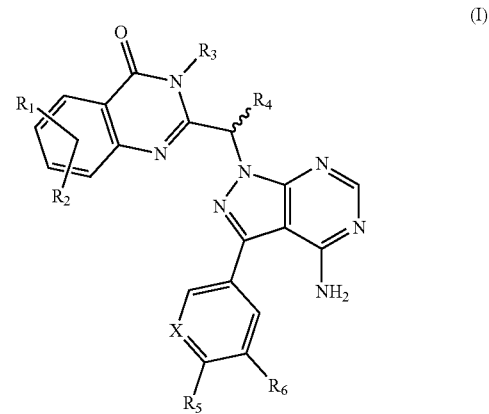

(I)

wherein,

X is selected from the group consisting of CH and N;

$R_1$ and $R_2$ are each independently selected from the group consisting of hydrogen, halogen, and $C_{1-6}$ haloalkyl;

$R_3$ is $C_{3-8}$ cycloalkyl;

$R_4$ is selected from the group consisting of hydrogen and $C_{1-6}$ alkyl;

$R_5$ is selected from the group consisting of hydrogen, $C_{1-6}$ alkyl, $C_{1-6}$ alkoxy, $C_{2-6}$ alkylamido, and $C_{1-6}$ alkylaminoacyl;

$R_6$ is selected from the group consisting of hydrogen, hydroxy, halogen, $C_{1-6}$ alkyl, and $C_{1-6}$ alkoxy;

or $R_5$ and $R_6$ together form a phenyl group or a dioxolane group.

In a preferred embodiment, X is CH.

Preferably, $R_1$ and $R_2$ are each independently selected from the group consisting of hydrogen, fluorine, and methyl; more preferably, both $R_1$ and $R_2$ are hydrogen, or one of them is hydrogen and the other one is fluorine.

Further preferably, $R_3$ is a $C_{3-6}$ cycloalkyl group, such as cyclopropyl, cyclobutyl, cyclopentyl, or cyclohexyl.

Still preferably, $R_4$ is selected from the group consisting of hydrogen, methyl, and ethyl.

Further preferably, $R_5$ is selected from the group consisting of hydrogen, $C_{1-3}$ alkyl (such as methyl, ethyl, isopropyl), $C_{1-3}$ alkoxy (such as methoxy, ethoxy, isopropoxy), $C_{2-3}$ alkylamido (such as acetamido-NH—(C=O)—CH₃) and $C_{1-3}$ alkylaminoacyl (such as methylaminoaeyl-(C=O)—NH—CH₃); particularly preferably, $R_5$ is methoxy.

Still preferably, $R_6$ is selected from the group consisting of hydrogen, hydroxy, halogen (such as fluorine, chlorine), $C_{1-3}$ alkyl (such as methyl), and $C_{1-3}$ alkoxy (such as methoxy); particularly preferably, $R_6$ is selected from the group consisting of hydrogen, fluorine, and methoxy.

In a preferred embodiment, $R_5$ and $R_6$ are not hydrogen at the same time.

In the invention, particularly preferred compounds of formula (I) are selected from the group consisting of the compounds of Table 1 below.

TABLE 1

| No. | Structure |
| --- | --- |
| 1 | 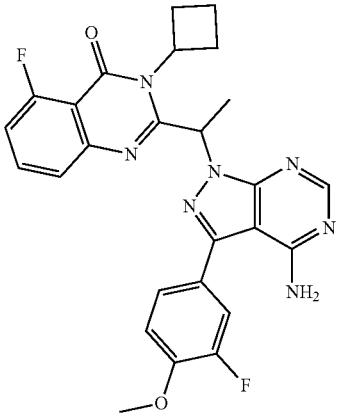 |
| 2 | 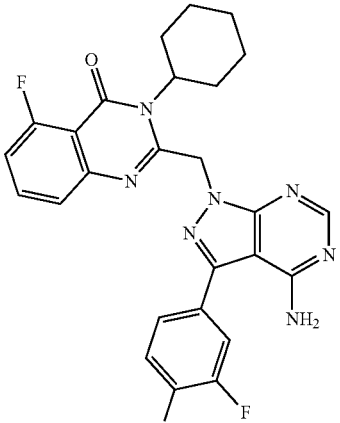 |
| 3 | 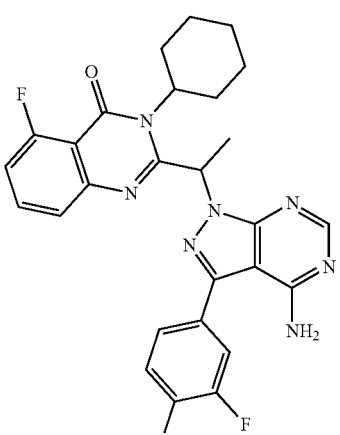 |

TABLE 1-continued

| No. | Structure |
| --- | --- |
| 4 | 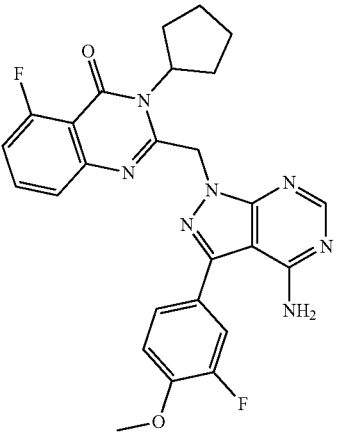 [SMILES: COc1ccc(-c2nn(Cc3nc4cccc(F)c4c(=O)n3C3CCCC3)c3ncnc(N)c23)cc1F] |
| 5 | 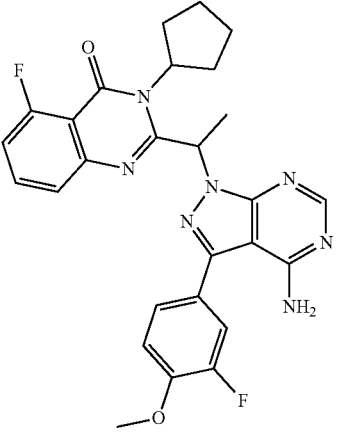 |
| 6 | 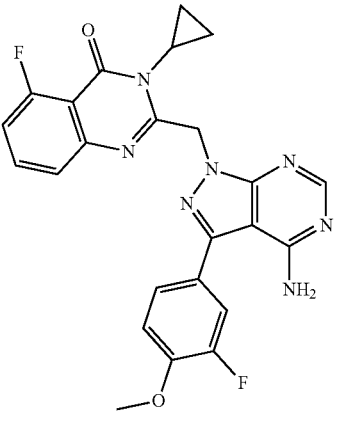 [SMILES: COc1ccc(-c2nn(Cc3nc4cccc(F)c4c(=O)n3C3CC3)c3ncnc(N)c23)cc1F] |

TABLE 1-continued
| No. | Structure |
|---|---|
| 7 | 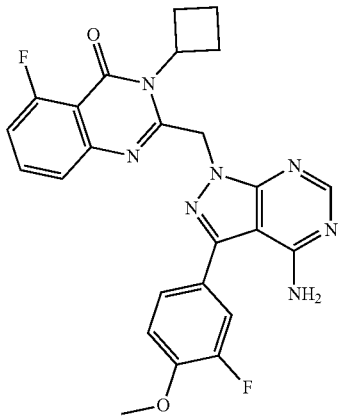 [SMILES: COc1ccc(-c2nn(Cc3nc4cccc(F)c4c(=O)n3C3CCC3)c3ncnc(N)c23)cc1F] |
| 8 | 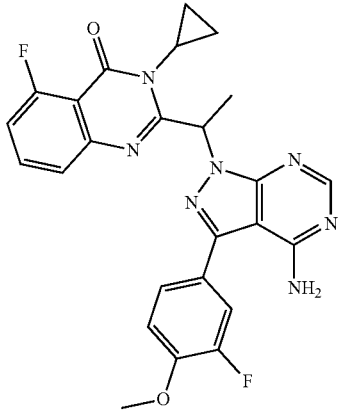 [SMILES: COc1ccc(-c2nn(C(C)c3nc4cccc(F)c4c(=O)n3C3CC3)c3ncnc(N)c23)cc1F] |
| 9 | 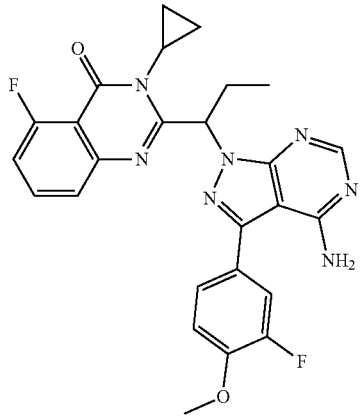 [SMILES: CCC(c1nc2cccc(F)c2c(=O)n1C1CC1)n1nc(-c2ccc(OC)c(F)c2)c2c(N)ncnc21] |
| 10 | 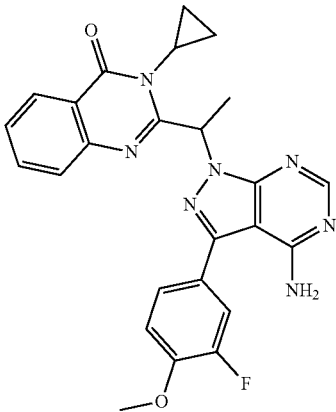 [SMILES: COc1ccc(-c2nn(C(C)c3nc4ccccc4c(=O)n3C3CC3)c3ncnc(N)c23)cc1F] |
| 11 | 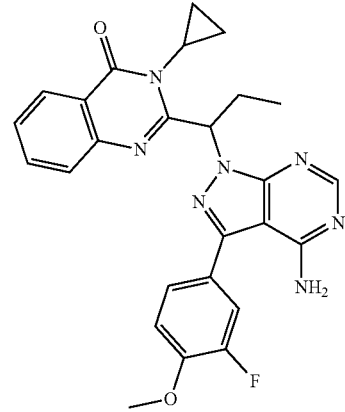 [SMILES: CCC(c1nc2ccccc2c(=O)n1C1CC1)n1nc(-c2ccc(OC)c(F)c2)c2c(N)ncnc21] |
| 12 | 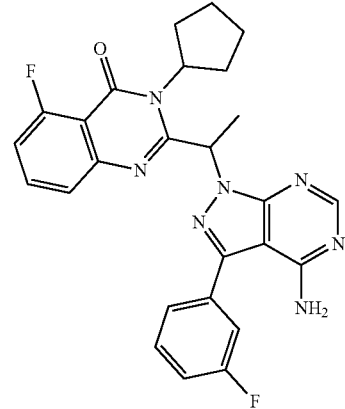 [SMILES: CC(c1nc2cccc(F)c2c(=O)n1C1CCCC1)n1nc(-c2cccc(F)c2)c2c(N)ncnc21] |

TABLE 1-continued

| No. | Structure |
|---|---|
| 13 | 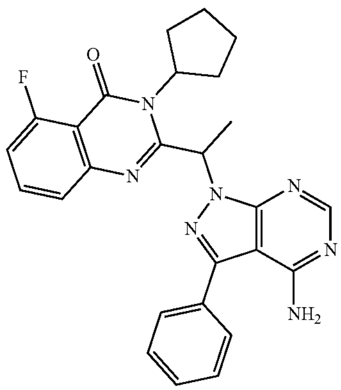 [SMILES: CC(c1nc2cccc(F)c2c(=O)n1C1CCCC1)n1nc(-c2ccccc2)c2c(N)ncnc21] |
| 14 | 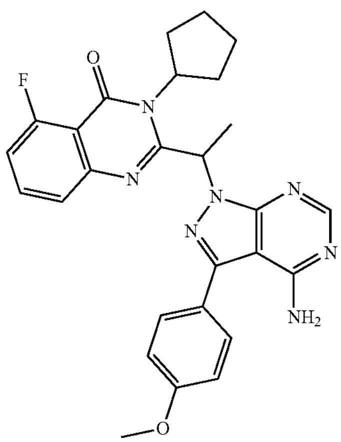 [SMILES: COc1ccc(-c2nn(C(C)c3nc4cccc(F)c4c(=O)n3C3CCCC3)c3ncnc(N)c23)cc1] |
| 15 | 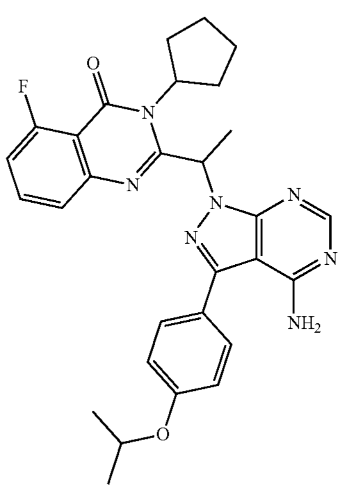 [SMILES: CC(C)Oc1ccc(-c2nn(C(C)c3nc4cccc(F)c4c(=O)n3C3CCCC3)c3ncnc(N)c23)cc1] |
| 16 | |
| 17 | |
| 18 | |

TABLE 1-continued

| No. | Structure |
|---|---|
| 19 | 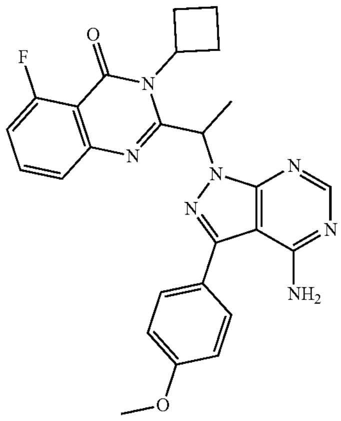 |
| 20 | 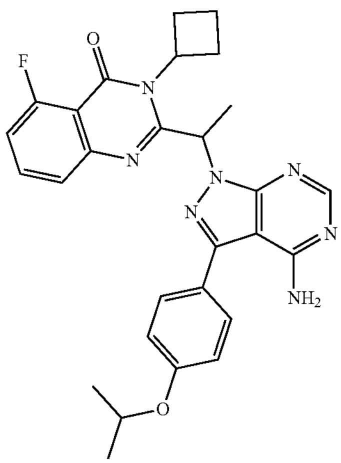 [SMILES: CC(C)Oc1ccc(-c2nn(C(C)c3nc4cccc(F)c4c(=O)n3C3CCC3)c3ncnc(N)c23)cc1] |
| 21 | 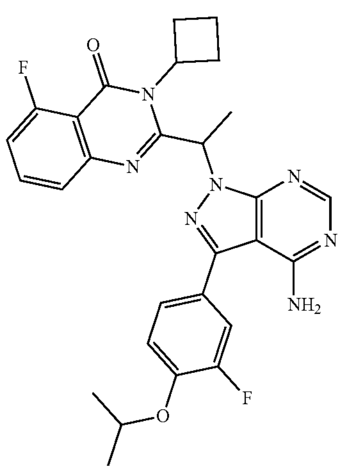 [SMILES: CC(C)Oc1ccc(-c2nn(C(C)c3nc4cccc(F)c4c(=O)n3C3CCC3)c3ncnc(N)c23)cc1F] |
| 22 | |
| 23 | |
| 24 | |

TABLE 1-continued
| No. | Structure |
|---|---|
| 25 | 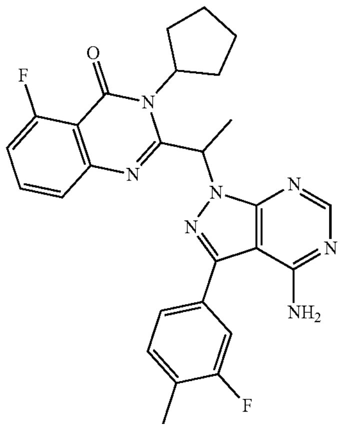 [SMILES: Cc1ccc(-c2nn(C(C)c3nc4cccc(F)c4c(=O)n3C3CCCC3)c3ncnc(N)c23)cc1F] |
| 26 | 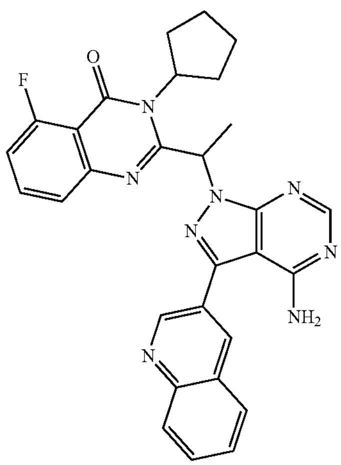 [SMILES: CC(c1nc2cccc(F)c2c(=O)n1C1CCCC1)n1nc(-c2cnc3ccccc3c2)c2c(N)ncnc21] |
| 27 | 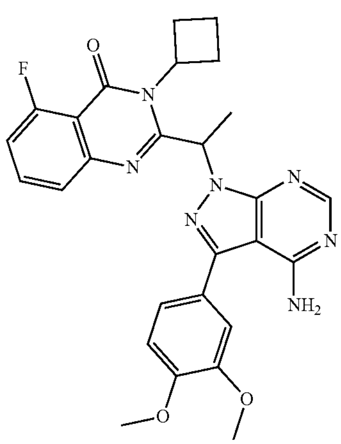 [SMILES: COc1ccc(-c2nn(C(C)c3nc4cccc(F)c4c(=O)n3C3CCC3)c3ncnc(N)c23)cc1OC] |
| 28 | |
| 29 | |
| 30 | |
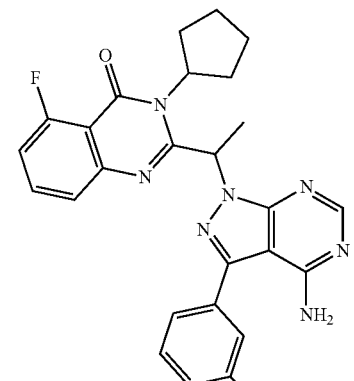

TABLE 1-continued
| No. | Structure |
|-----|-----------|
| 31 | 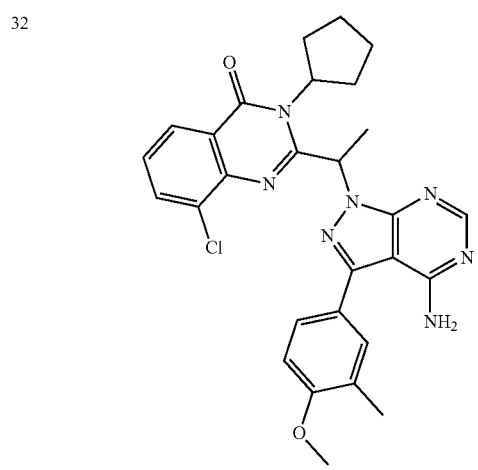 |
| 32 | 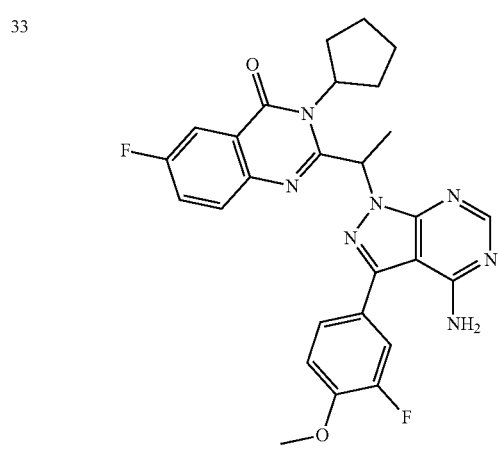 |
TABLE 1-continued
| No. | Structure |
|-----|-----------|
| 34 | 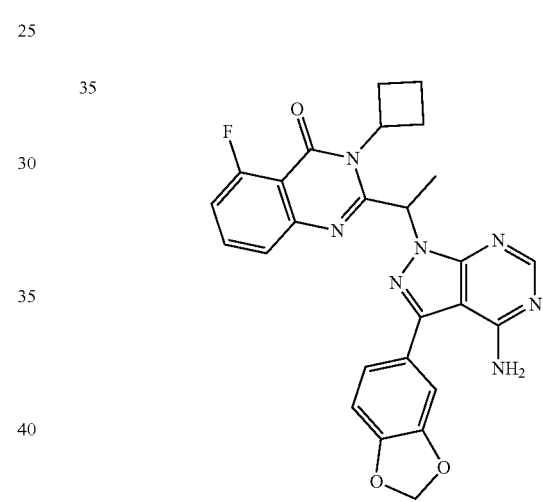 |
| 35 | 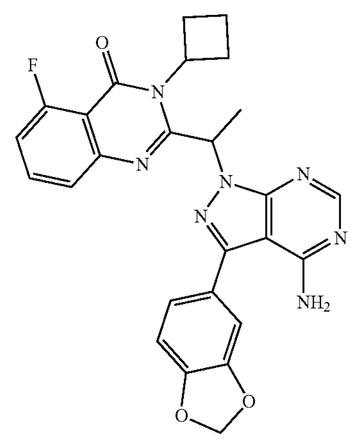 [SMILES: CC(c1nc2cccc(F)c2c(=O)n1C1CCC1)n1nc(-c2ccc3c(c2)OCO3)c2c(N)ncnc21] |
| 36 | 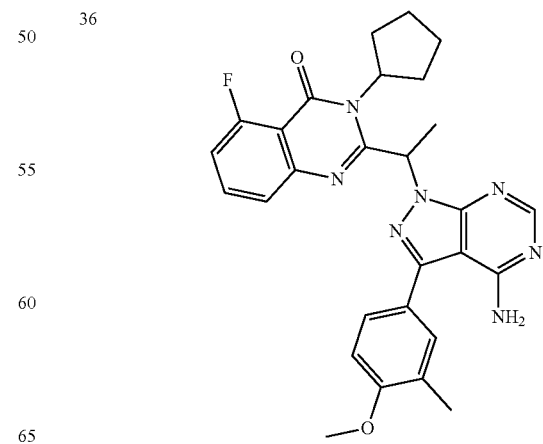 |
33

TABLE 1-continued
| No. | Structure |
|---|---|
| 37 | 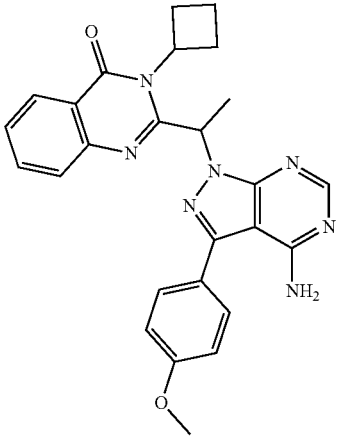 [SMILES: COc1ccc(-c2nn(C(C)c3nc4ccccc4c(=O)n3C3CCC3)c3ncnc(N)c23)cc1] |
| 38 | 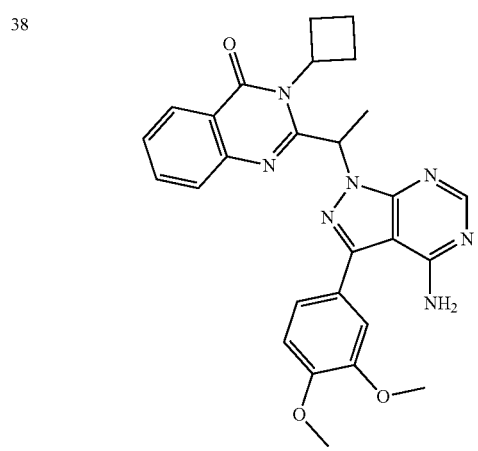 |
| 39 | 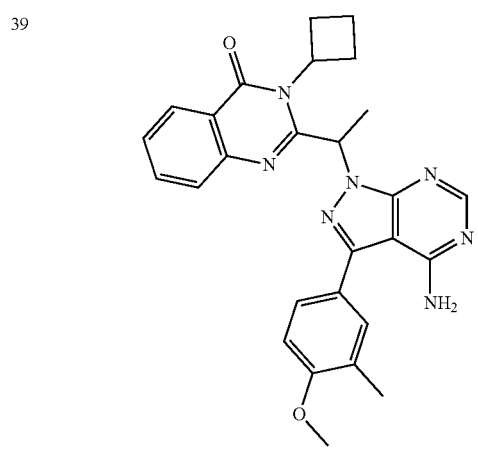 |
| 40 | 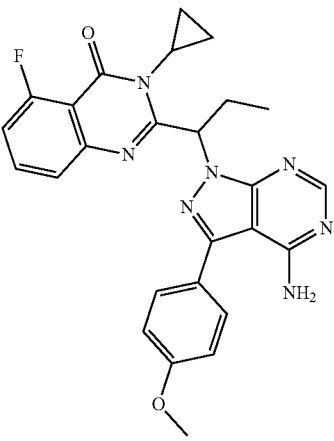 [SMILES: CCC(c1nc2cccc(F)c2c(=O)n1C1CC1)n1nc(-c2ccc(OC)cc2)c2c(N)ncnc21] |
| 41 | 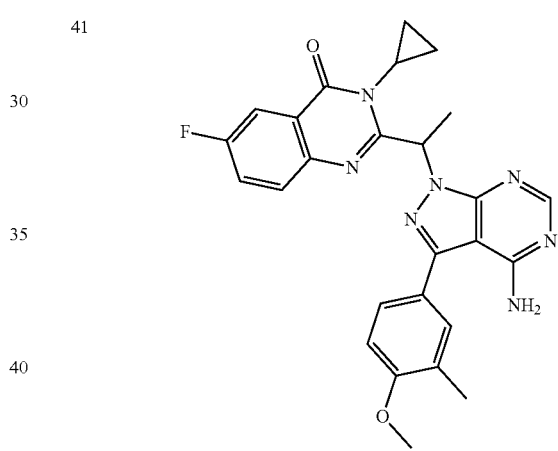 |
| 42 | 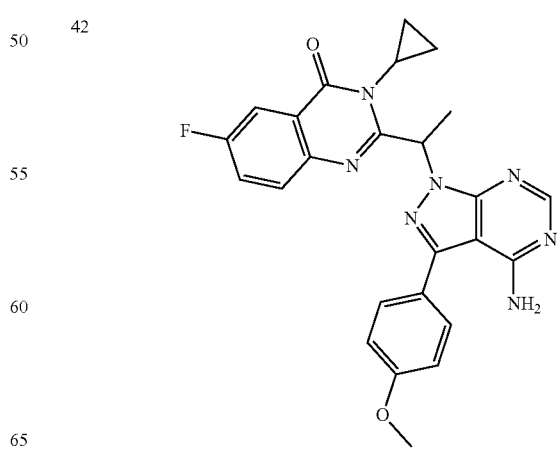 |

TABLE 1-continued
| No. | Structure |
|---|---|
| 43 | 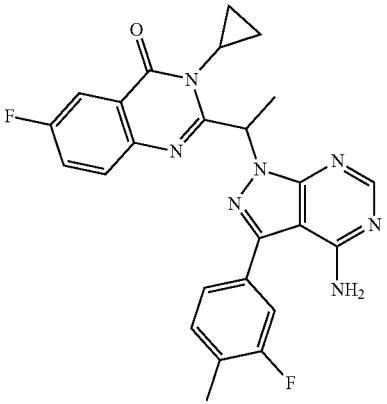 [SMILES: Cc1ccc(-c2nn(C(C)c3nc4ccc(F)cc4c(=O)n3C3CC3)c3ncnc(N)c23)cc1F] |
| 44 | 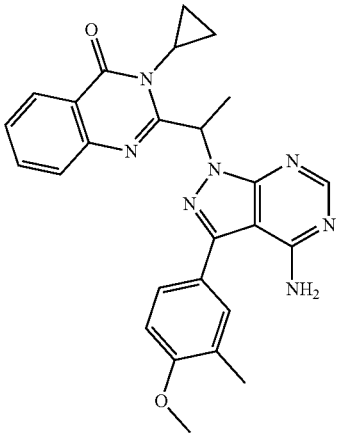 [SMILES: COc1ccc(-c2nn(C(C)c3nc4ccccc4c(=O)n3C3CC3)c3ncnc(N)c23)cc1C] |
| 45 | 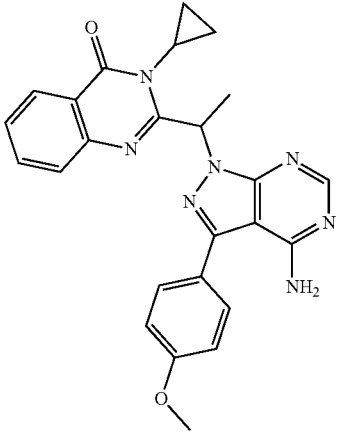 [SMILES: COc1ccc(-c2nn(C(C)c3nc4ccccc4c(=O)n3C3CC3)c3ncnc(N)c23)cc1] |
TABLE 1-continued
| No. | Structure |
|---|---|
| 46 | 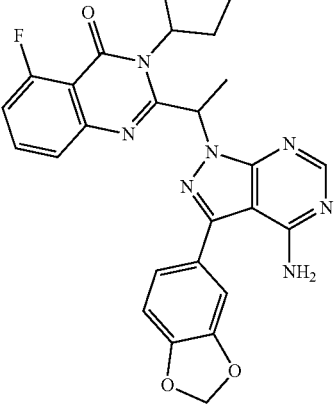 |
| 47 | 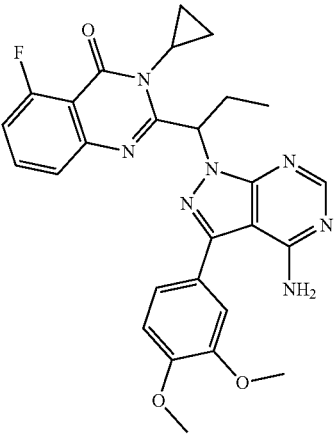 [SMILES: CCC(c1nc2cccc(F)c2c(=O)n1C1CC1)n1nc(-c2ccc(OC)c(OC)c2)c2c(N)ncnc21] |
| 48 | 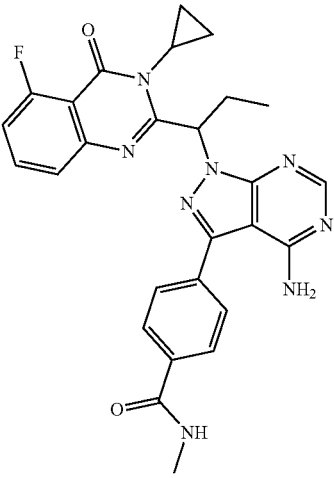 [SMILES: CCC(c1nc2cccc(F)c2c(=O)n1C1CC1)n1nc(-c2ccc(C(=O)NC)cc2)c2c(N)ncnc21] |

TABLE 1-continued
| No. | Structure |
|---|---|
| 49 | 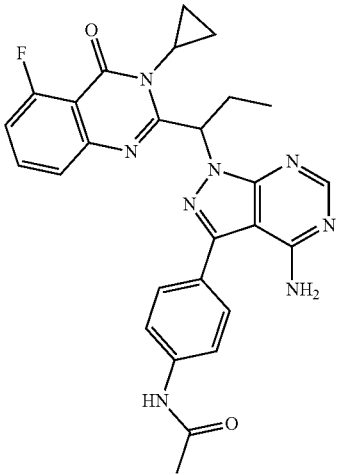 [SMILES: CCC(c1nc2cccc(F)c2c(=O)n1C1CC1)n1nc(-c2ccc(NC(C)=O)cc2)c2c(N)ncnc21] |
| 50 | 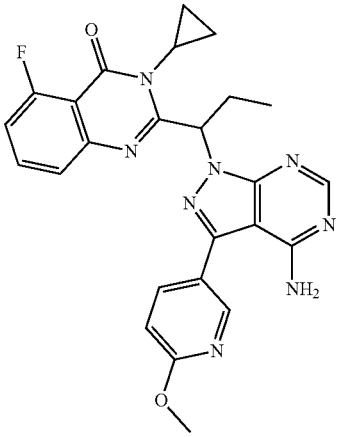 [SMILES: CCC(c1nc2cccc(F)c2c(=O)n1C1CC1)n1nc(-c2ccc(OC)nc2)c2c(N)ncnc21] |
| 51 | 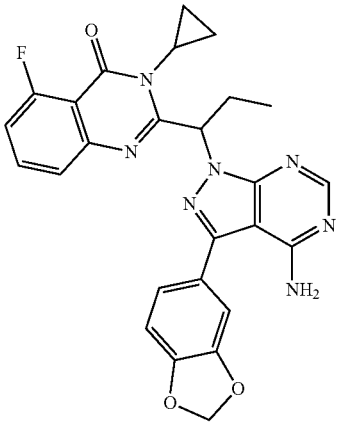 [SMILES: CCC(c1nc2cccc(F)c2c(=O)n1C1CC1)n1nc(-c2ccc3c(c2)OCO3)c2c(N)ncnc21] |†
TABLE 1-continued
| No. | Structure |
|---|---|
| 52 | 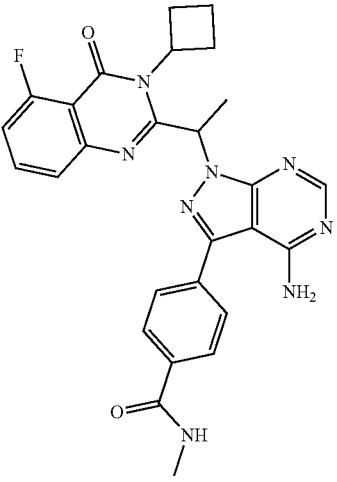 [SMILES: CNC(=O)c1ccc(-c2nn(C(C)c3nc4cccc(F)c4c(=O)n3C3CCC3)c3ncnc(N)c23)cc1] |
| 53 | 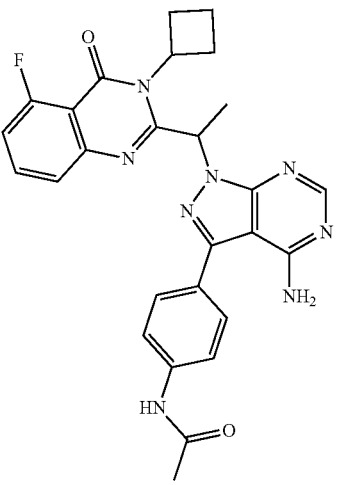 [SMILES: CC(=O)Nc1ccc(-c2nn(C(C)c3nc4cccc(F)c4c(=O)n3C3CCC3)c3ncnc(N)c23)cc1] |
| 54 | 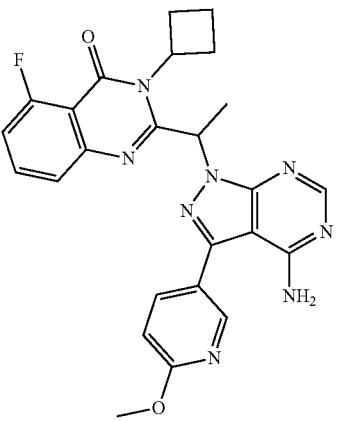 |

TABLE 1-continued
| No. | Structure |
|---|---|
| 55 | 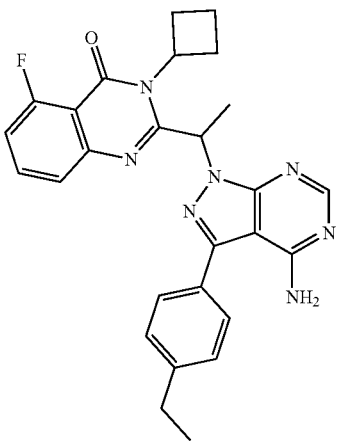 [SMILES: CCc1ccc(-c2nn(C(C)c3nc4cccc(F)c4c(=O)n3C3CCC3)c3ncnc(N)c23)cc1] |
| 56 | 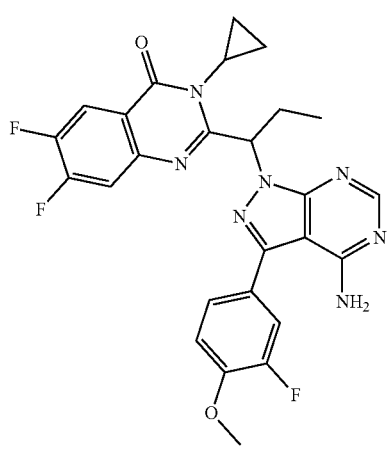 [SMILES: CCC(c1nc2cc(F)c(F)cc2c(=O)n1C1CC1)n1nc(-c2ccc(OC)c(F)c2)c2c(N)ncnc21] |
| 57 | 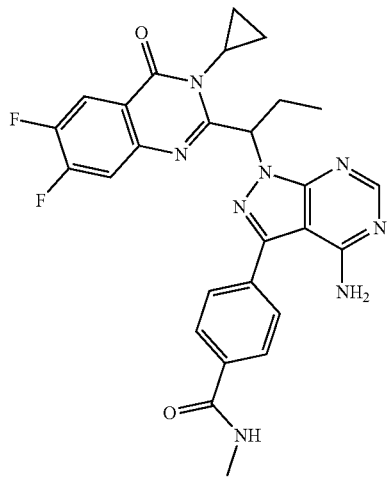 [SMILES: CCC(c1nc2cc(F)c(F)cc2c(=O)n1C1CC1)n1nc(-c2ccc(C(=O)NC)cc2)c2c(N)ncnc21] |
| 58 | 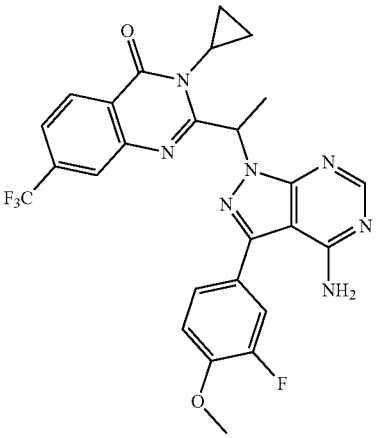 [SMILES: COc1ccc(-c2nn(C(C)c3nc4cc(C(F)(F)F)ccc4c(=O)n3C3CC3)c3ncnc(N)c23)cc1F] |
| 59 | 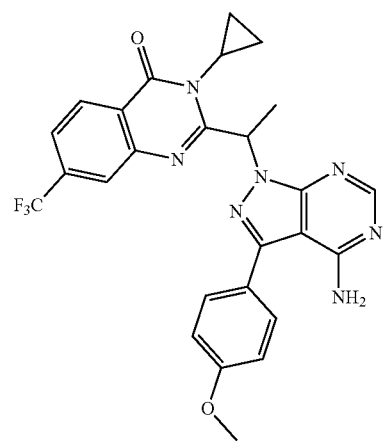 [SMILES: COc1ccc(-c2nn(C(C)c3nc4cc(C(F)(F)F)ccc4c(=O)n3C3CC3)c3ncnc(N)c23)cc1] |
| 60 | 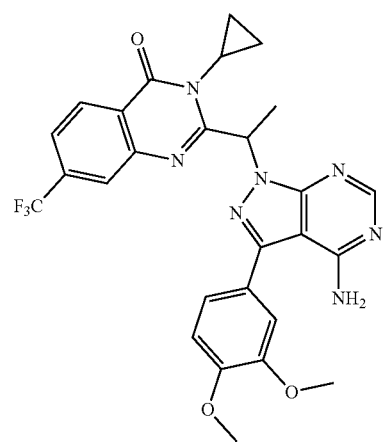 [SMILES: COc1ccc(-c2nn(C(C)c3nc4cc(C(F)(F)F)ccc4c(=O)n3C3CC3)c3ncnc(N)c23)cc1OC] |

TABLE 1-continued
| No. | Structure |
|---|---|
| 61 | 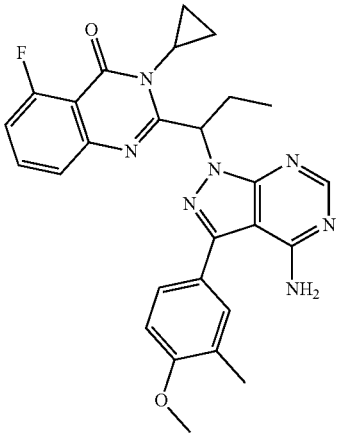 [SMILES: CCC(c1nc2cccc(F)c2c(=O)n1C1CC1)n1nc(-c2ccc(OC)c(C)c2)c2c(N)ncnc21] |
| 62 | 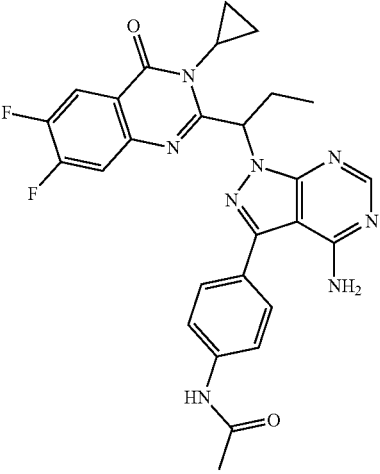 [SMILES: CCC(c1nc2cc(F)c(F)cc2c(=O)n1C1CC1)n1nc(-c2ccc(NC(C)=O)cc2)c2c(N)ncnc21] |
| 63 | 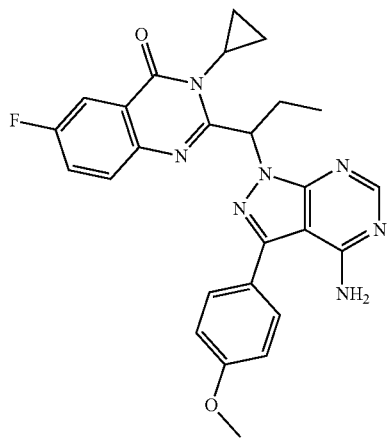 |
TABLE 1-continued
| No. | Structure |
|---|---|
| 64 | 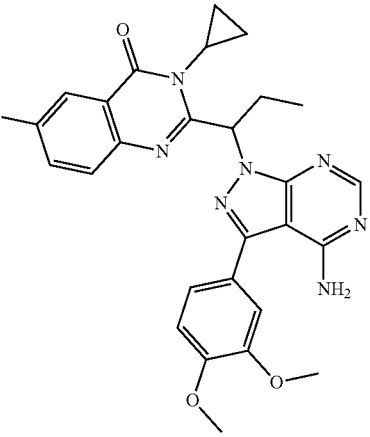 |
| 65 | 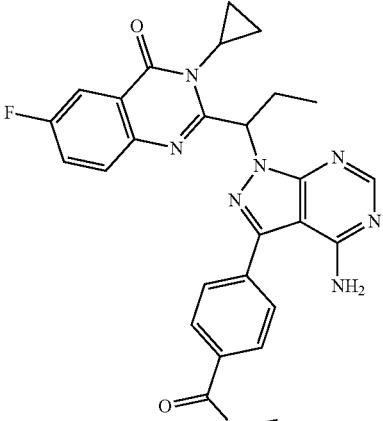 |
| 66 | 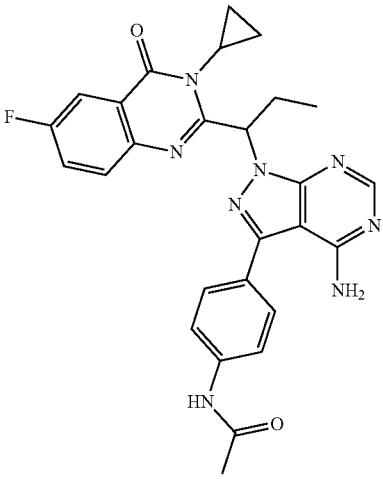 [SMILES: CCC(c1nc2ccc(F)cc2c(=O)n1C1CC1)n1nc(-c2ccc(NC(C)=O)cc2)c2c(N)ncnc21] |

TABLE 1-continued
| No. | Structure |
|---|---|
| 67 | 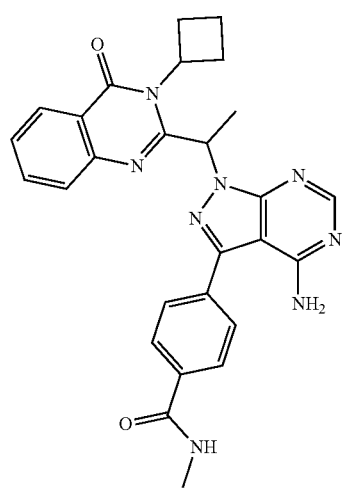 [SMILES: CNC(=O)c1ccc(-c2nn(C(C)c3nc4ccccc4c(=O)n3C3CCC3)c3ncnc(N)c23)cc1] |
| 68 | 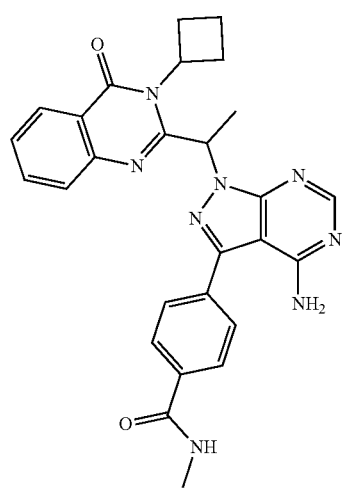 [SMILES: CNC(=O)c1ccc(-c2nn(C(C)c3nc4ccccc4c(=O)n3C3CCC3)c3ncnc(N)c23)cc1] |
| 69 | 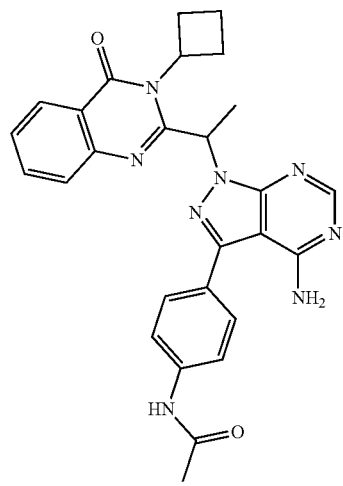 [SMILES: CC(=O)Nc1ccc(-c2nn(C(C)c3nc4ccccc4c(=O)n3C3CCC3)c3ncnc(N)c23)cc1] |
TABLE 1-continued
| No. | Structure |
|---|---|
| 70 | 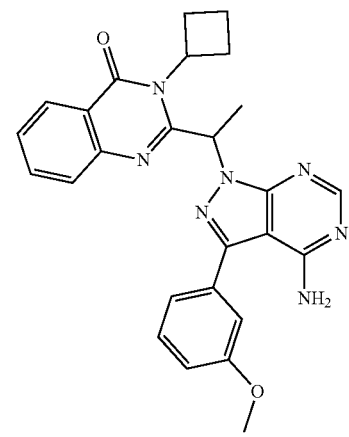 [SMILES: COc1cccc(-c2nn(C(C)c3nc4ccccc4c(=O)n3C3CCC3)c3ncnc(N)c23)c1] |
| 71 | 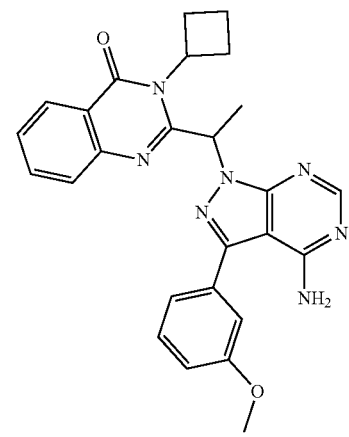 [SMILES: COc1cccc(-c2nn(C(C)c3nc4ccccc4c(=O)n3C3CCC3)c3ncnc(N)c23)c1] |
| 72 | 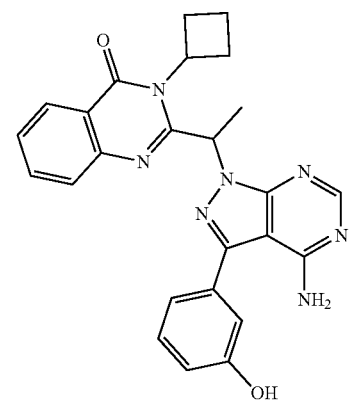 [SMILES: CC(c1nc2ccccc2c(=O)n1C1CCC1)n1nc(-c2cccc(O)c2)c2c(N)ncnc21] |

TABLE 1-continued
| No. | Structure |
|---|---|
| 73 | 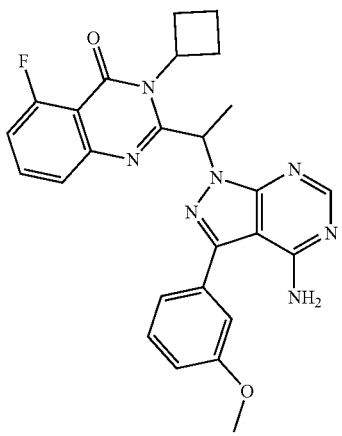 [SMILES: COc1cccc(-c2nn(C(C)c3nc4cccc(F)c4c(=O)n3C3CCC3)c3ncnc(N)c23)c1] |
| 74 | 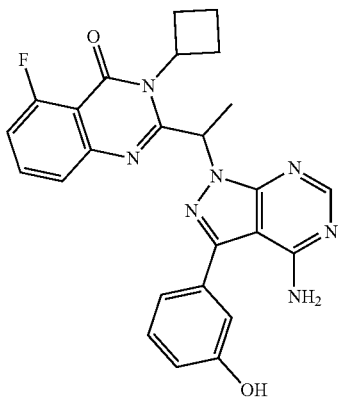 [SMILES: CC(c1nc2cccc(F)c2c(=O)n1C1CCC1)n1nc(-c2cccc(O)c2)c2c(N)ncnc21] |
| 75 | 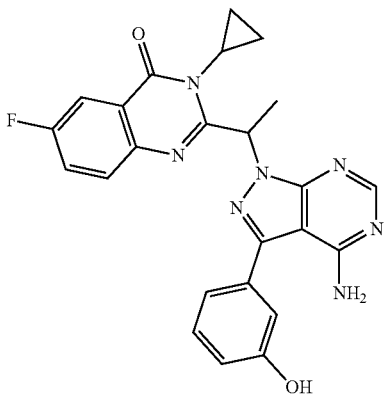 [SMILES: CC(c1nc2ccc(F)cc2c(=O)n1C1CC1)n1nc(-c2cccc(O)c2)c2c(N)ncnc21] |
| 76 | 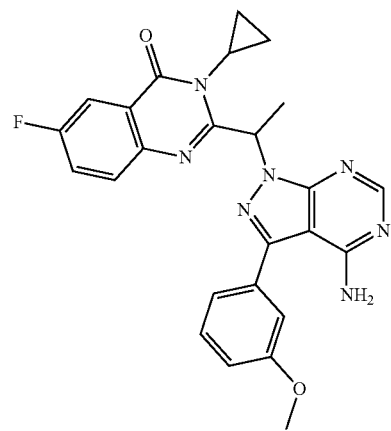 [SMILES: COc1cccc(-c2nn(C(C)c3nc4ccc(F)cc4c(=O)n3C3CC3)c3ncnc(N)c23)c1] |
| 77 | 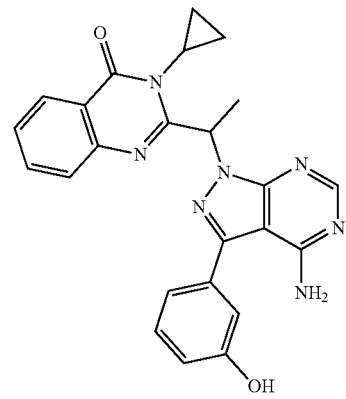 [SMILES: CC(c1nc2ccccc2c(=O)n1C1CC1)n1nc(-c2cccc(O)c2)c2c(N)ncnc21] |
| 78 | 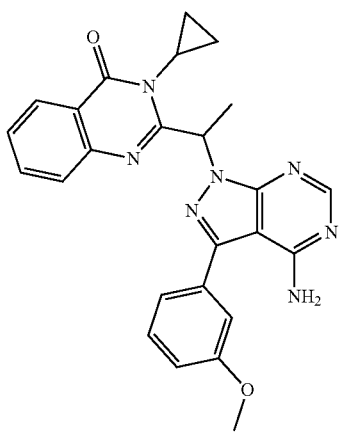 [SMILES: COc1cccc(-c2nn(C(C)c3nc4ccccc4c(=O)n3C3CC3)c3ncnc(N)c23)c1] |

TABLE 1-continued

| No. | Structure |
|---|---|
| 79 | 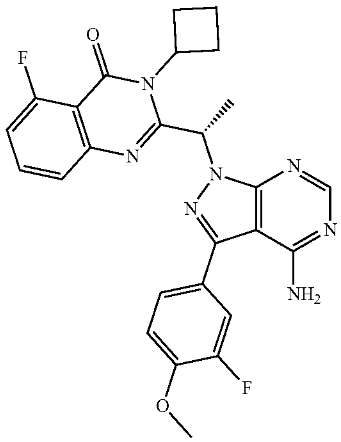 [SMILES: COc1ccc(-c2nn([C@@H](C)c3nc4cccc(F)c4c(=O)n3C3CCC3)c3ncnc(N)c23)cc1F] |
| 80 | 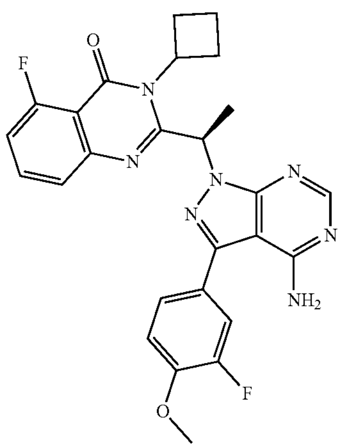 [SMILES: COc1ccc(-c2nn([C@H](C)c3nc4cccc(F)c4c(=O)n3C3CCC3)c3ncnc(N)c23)cc1F] |
| 81 | 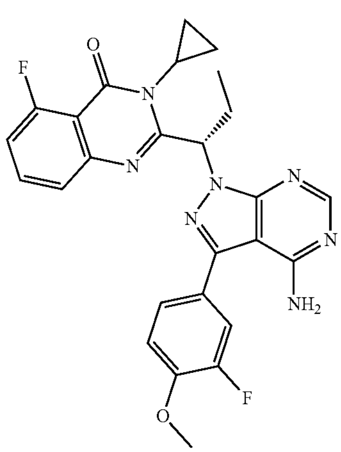 [SMILES: CC[C@@H](c1nc2cccc(F)c2c(=O)n1C1CC1)n1nc(-c2ccc(OC)c(F)c2)c2c(N)ncnc21] |
| 82 | |

The invention also relates to a pharmaceutical composition comprising the above compound or a pharmaceutically acceptable salt, solvate, ester, acid, metabolite or prodrug thereof, and a method and use for using the compound or pharmaceutical composition to inhibit the activity of tyrosine kinase (including the wild type or various mutations or combinations thereof), and a method and use for the treatment, prevention or amelioration of diseases, disorders or conditions that are regulated by or affected by the activity of tyrosine kinase or in which the activity of tyrosine kinase is involved, wherein the tyrosine kinase may be PI3Kδ.

Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein Described herein is a novel kinase inhibitor. The pharmaceutically acceptable salts, solvates, esters, acids, pharmaceutically active metabolites and prodrugs of these compounds are also described herein.

In additional or further embodiments, the compounds described herein are metabolized upon administration to an organism in need thereof to produce a metabolite that is then used to produce a desired effect, including a desired therapeutic effect.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable inorganic acid such as hydrochloric acid, hydrobromic acid, sulfuric acid, nitric acid, phosphoric acid, metaphosphoric acid, and the like; or with an organic acid such as acetic acid, propionic acid, hexanoic acid, cyclopentanepropionic acid, glycolic acid, pyruvic acid, lactic acid, malonic acid, malic acid, citric acid, succinic acid, maleic acid, tartaric acid, fumaric acid, trifluoroacetic acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 4-methylbicyclo-[2.2.2] oct-2-ene-1-carboxylic acid, 2-naphthalenesulfonic acid, tertiary butylacetic acid, glucoheptonic acid, 4,4'-methylenebis-(3- hydroxy-2-ene-1-carboxylic acid), 3-phenylpropionic acid, trimethylacetic acid, lauryl sulfuric acid, gluconic acid, glutamic acid, salicylic acid, hydroxynaphthoic acid, stearic acid, muconic acid, and the like; (2) base addition salts formed when an acidic proton present in the parent compound either is replaced by a metal ion, e.g., an alkali metal ion (e.g. lithium, sodium, potassium), an alkaline earth metal ion (e.g. magnesium, or calcium), or an aluminum ion; or coordinates with an organic base. Acceptable organic bases include ethanolamine, diethanolamine, triethanolamine, trimethylamine, N-methylglucamine, and the like. Acceptable inorganic bases include aluminum hydroxide, calcium hydroxide, potassium hydroxide, sodium carbonate, sodium hydroxide, and the like.

The corresponding counterions of the pharmaceutically acceptable salts may be analyzed and identified using various methods including, but not limited to, ion exchange chromatography, ion chromatography, capillary electrophoresis, inductively coupled plasma, atomic absorption spectroscopy, mass spectrometry, or any combination thereof.

The salts are recovered by using at least one of the following techniques: filtration, precipitation with a non-solvent followed by filtration, evaporation of the solvent, or, in the case of aqueous solutions, lyophilization.

The screening and characterization of the pharmaceutically acceptable salts, polymorphs and/or solvates may be accomplished using a variety of techniques including, but not limited to, thermal analysis, x-ray diffraction, spectroscopy, microscopy and element analysis. The various spectroscopic techniques used include, but are not limited to, Raman, FTIR, UVIS, and NMR (liquid and solid state). The various microscopy techniques include, but are not limited to, IR microscopy and Raman microscopy.

The Pharmaceutical Composition of the Invention

This application also provides a pharmaceutical composition comprising at least one compound of formula (I), or a pharmaceutically acceptable salt, solvate, ester, acid, pharmaceutically active metabolite or prodrug of the compound, and a pharmaceutically acceptable carrier or excipient, and optionally other therapeutic agents.

In the course of treatment, it may be used alone or in combination with one or more other therapeutic agents depending on the situation. The medicament containing the compound of the invention may be administered to the patients through at least one of injection, oral administration, inhalation, rectal and transdermal administration.

Other therapeutic agents may be selected from the group consisting of: immunosuppressants (e.g., tacrolimus, cyclosporin, rapamycin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), allergy vaccines, antihistamines, antileukotrienes, β-agonists, theophylline, anticholinergics, or other selective kinase inhibitors (e.g., mTOR inhibitors, c-Met inhibitors) or her2 antibodies. In addition, the other therapeutic agents may also be Rapamycin, Crizotinib, Tamoxifen, Raloxifene, Anastrozole, Exemestane, Letrozole, Herceptin™ (Trastuzumab), Gleevec™ (Imatinib), Taxol™ (Paclitaxel), Cyclophosphamide, Lovastatin, Minosine, Cytarabine, 5-Fluorouracil (5-FU), Methotrexate (MTX), Taxotere™ (Docetaxel), Zoladex™ (Goserelin), Vincristine, Vinblastine, Nocodazole, Teniposide, Etoposide, Gemzar™ (Gemcitabine), Epothilone, Navelbine, Camptothecin, Daunonibicin, Dactinomycin, Mitoxantrone, Amsacrine, Doxorubicin (Adriamycin), Epirubicin or Idarubicin. Alternatively, other therapeutic agents may be cytokines such as G-CSF (Granulocyte-Colony Stimulating Factor). Alternatively, other therapeutic agents may be for example, but are not limited to, CMF (Cyclophosphamide, Methotrexate and 5-Fluorouracil), CAF (Cyclophosphamide, Adriamycin and 5-Fluorouracil), AC (Adriamycin and Cyclophosphamide), FEC (5-Fluorouracil, Epirubicin and Cyclophosphamide), ACT or ATC (Adriamycin, Cyclophosphamide and Paclitaxel) or CMFP (Cyclophosphamide, Methotrexate, 5-Fluorouracil and Prednisone).

In the embodiments of the invention, when a patient is treated in accordance with the invention, the amount of a given agent will vary depending upon factors such as the particular dosing regimen, the type of the disease or condition and its severity, the characteristics (e.g., weight) of the subject or host in need of treatment, but can be routinely determined in a manner known in the art according to the particular circumstances surrounding the case, including, e.g., the specific agent being administered, the route of administration, the condition being treated, and the subject or host being treated. In general, doses employed for adult human treatment will typically be in the range of 0.02-5000 mg per day, such as about 1-1500 mg per day. The desired dose may be conveniently presented in a single dose or as divided doses administered simultaneously (or over a short period of time) or at appropriate intervals, for example as two, three, four or more sub-doses per day. It will be appreciated by those skilled in the art that, although the above dosage ranges are given, the specific effective amounts may be appropriately adjusted depending on the condition of the patient and the judgment of the practitioner.

Use of the Compound of the Invention

The "treatment" of the invention can be therapeutic (such as symptomatic treatment) and/or prophylactic.

Preferred is a use for the treatment of a proliferative disease selected from a benign or malignant tumor, including but not limited to: brain cancer, kidney cancer, liver cancer, adrenal cancer, bladder cancer, breast cancer, lymphoma, gastric cancer, gastric tumor, esophageal cancer, ovarian cancer, colorectal cancer, prostate cancer, pancreatic cancer, lung cancer, vaginal cancer, pancreatic cancer, thyroid carcinoma, neck cancer, CNS cancer, malignant glioma, myeloproliferative diseases, sarcoma, glioblastoma, multiple myeloma, gastrointestinal cancer, colorectal cancer, head and neck tumor, brain tumor, epidermal hyperplasia, psoriasis, prostate hyperplasia, neoplasia, epithelial neoplasia, lymphoma, breast cancer, or leukemia. Other diseases include Cowden syndrome, Lhermitte-Dudos disease and Bannayan-Zonana syndrome or diseases in which the PI3K/PKB pathway is aberrantly activated. Preferred is the treatment of lymphoma and hematological tumors, and more preferred is the treatment of chronic lymphocytic leukemia, non-Hodgkin's lymphoma, Hodgkin's lymphoma, mantle cell lymphoma, or the like diseases.

Compounds according to the invention are also of use in the treatment of inflammatory or obstructive airways diseases, resulting, for example, in reduction of tissue damage, airways inflammation, bronchial hyperreactivity, remodeling or disease progression. Inflammatory or obstructive airways diseases to which the invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. For convenience this particular asthmatic condition is referred to as "wheezy-infant syndrome".

Prophylactic efficacy in the treatment of asthma can be evidenced by reduced frequency or severity of symptomatic attack, e.g. of acute asthmatic or bronchoconstrictor attack, improvement in lung function or improved airways hyper-reactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant form any previously administered symptomatic asthma therapy.

Other inflammatory or obstructive airways diseases and conditions to which the invention is applicable include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy.

The invention is also applicable to the treatment of bronchitis of whatever type or genesis including, e.g., acute, arachidic, catarrhal, fibrinous, chronic or phthinoid bronchitis. Further inflammatory or obstructive airways diseases to which the invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Compounds according to the invention are also of use in the treatment of the following diseases, disorders or conditions mediated by phosphatidylinositol 3-kinase: respiratory diseases, allergies, rheumatoid arthritis, osteoarthritis, rheumatic disorders, psoriasis, ulcerative colitis, Crohn's disease, septic shock, proliferative disorder, atherosclerosis, allograft rejection after transplantation, diabetes, stroke, obesity or restenosis, leukemia, interstitialoma, thyroid carcinoma, systemic mastocytosis, eosinophilia syndrome, fibrosis, rheumatoid arthritis, polyarthritis, scleroderma, lupus erythematosus, graft versus host disease, neurofibromatosis, pulmonary hypertension, Alzheimer's disease, seminoma, dysgerminoma, mastocytoma, lung cancer, bronchial carcinoma, dysgerminoma, testicular intraepithelial neoplasia, melanoma, breast cancer, neuroblastoma, papillary/follicular thyroid carcinoma, malignant lymphoma, non-Hodgkin's lymphoma, type 2 multiple endocrine neoplasia, pheochromocytoma, thyroid carcinoma, parathyroid hyperplasia/adenoma, colon cancer, colorectal adenoma, ovarian cancer, prostate cancer, glioblastoma, brain tumor, malignant glioma, pancreatic cancer, malignant pleural mesothelioma, hemangioblastoma, hemangioma, kidney cancer, liver cancer, adrenal cancer, bladder cancer, gastric cancer, rectal cancer, vaginal cancer, cervical cancer, endometrial cancer, multiple myeloma, neck and head tumors, neoplasia and other hyperplastic or proliferative diseases, or combinations thereof. The medicament of the invention is particularly suitable for treating diseases selected from the group consisting of rheumatoid arthritis and systemic lupus erythematosus.

Compounds of the invention are also of use in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Loeffler's syndrome, eosinophilic pneumonia, parasitic (in particular metazoan) infestation (including tropical eosinophilia), bronchopulmonary aspergillosis, polyarteritis *nodosa* (including Churg-Strauss syndrome), eosinophilic granuloma and eosinophil-related disorders affecting the airways occasioned by drug-reaction.

Compounds of the invention are also of use in the treatment of inflammatory or allergic conditions of the skin, for example psoriasis, contact dermatitis, atopic dermatitis, alopecia areata, erythema multiforme, dermatitis herpetiformis, scleroderma, vitiligo, hypersensitivity angiitis, urticaria, bullous pemphigoid, lupus erythematosus, pemphigus, epidermolysis bullosa acquisita, and other inflammatory or allergic conditions of the skin.

Compounds of the invention may also be used for the treatment of other diseases or conditions, such as diseases or conditions having an inflammatory component, for example, treatment of diseases and conditions of the eye such as conjunctivitis, keratoconjunctivitis sicca, and vernal conjunctivitis, diseases affecting the nose including allergic rhinitis, and inflammatory disease in which autoimmune reactions are implicated or having an autoimmune component or aetiology, including autoimmune haematological disorders (e.g. haemolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary billiary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy).

Other diseases or conditions that can be treated with the compounds of the invention include septic shock, rheumatoid arthritis, osteoarthritis, proliferative diseases such as cancer, atherosclerosis, allograft rejection after transplantation, stroke, obesity, restenosis, diabetes such as type I diabetes (juvenile diabetes) and type II diabetes, diarrheal diseases, ischemia/reperfusion injury, retinopathy such as diabetic retinopathy or hyperbaric oxygen induced retinopathy, and conditions characterized by increased intraocular pressure or secretion of aqueous humor, such as glaucoma.

The effectiveness of the compounds of the invention in inhibiting inflammatory conditions such as inflammatory airways diseases can be demonstrated in animal models, such as mouse or rat models of airways inflammation or other inflammatory conditions, as described in e.g., Szarka et al., J. Immunol. Methods (1997) 202:49-57; Renzi et al., Am. Rev. Respir. Dis. (1993) 148:932-939; Tsuyuki et al., J. Clin. Invest. (1995) 96:2924-2931; and Cernadas et al., Am. J. Respir. Cell Mol. Biol. (1999) 20:1-8.

Preparation of the Compound

Compounds of formula (I) may be synthesized using standard synthetic techniques known to those of skill in the art or using methods known in the art in combination with methods described herein. In addition, solvents, temperatures and other reaction conditions presented herein may vary according to those of skill in the art. As a further guide, the following synthetic methods may also be utilized.

The reactions can be employed in a linear sequence to provide the compounds described herein or they may be used to synthesize fragments which are subsequently joined by the methods described herein and/or known in the art.

In certain embodiments, provided herein are methods of making and methods of using tyrosine kinase inhibitor compounds described herein. In certain embodiments, compounds described herein can be synthesized using the following synthetic schemes. Compounds may be synthesized using methodologies analogous to those described below by the use of appropriate alternative starting materials.

The starting materials used for the synthesis of the compounds described herein may be synthesized or can be obtained from commercial sources. The compounds described herein, and other related compounds having different substituents can be synthesized using techniques and materials known to those of skill in the art. General methods for the preparation of compounds as disclosed herein may be derived from known reactions in the field, and the reactions may be modified by the use of appropriate reagents and conditions, as would be recognized by the skilled person, for the introduction of the various moieties into the molecules as provided herein.

The products of the reactions may be isolated and purified, if desired, using conventional techniques, including, but not limited to, filtration, distillation, crystallization, chromatography and the like. Such products may be characterized using conventional means, including physical constants and spectral data.

Example 1: 2-(1-(4-amino-3-(3-fluoro-4-methoxyphenyl)-1H-pyrazolo [3,4-d]pyrimidin-1-yl)ethyl)-3-cyclobutyl-5-fluoroquinazolin-4(3H)-one

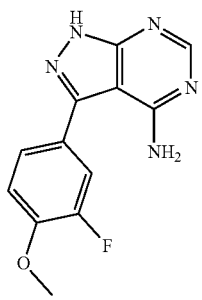

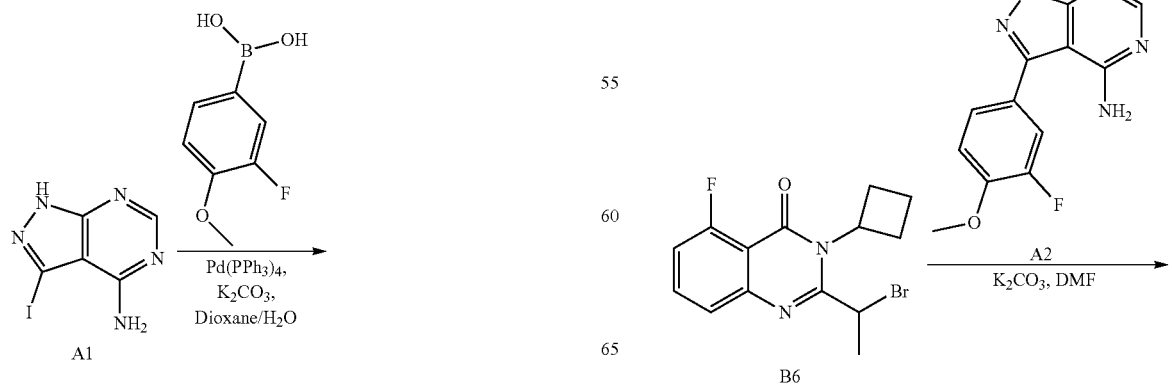

-continued

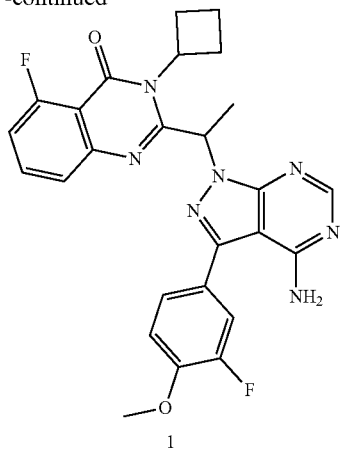

1

3-(3-Fluoro-4-methoxyphenyl)-1H-pyrazolo[3,4-d]pyrimidin-4-amine (A2): 3-iodo-1H-pyrazolo[3,4-d]pyrimidin-4-amine (2.0 g) was added in a round bottom flask, followed by addition of 1,4-dioxane (30 ml), water (10 ml), (3-fluoro-4-methoxyphenyl) boric acid (5.2 g), Pd(PPh$_3$)$_4$ (1.8 g), and potassium carbonate (2.1 g). The reaction system was allowed for reaction at 130° C. for 24 hours under the protection of argon. After the reaction, the system was evaporated to dry the solvent under reduced pressure, and the resultant was diluted with water and filtered. The filtered solid product was washed with dichloromethane to obtain crude product A2. LC/MS: M+H 260.09.

2-Fluoro-6-nitrobenzoyl chloride (B2): 2-fluoro-6-nitrobenzoic acid (14.0 g) was added in a round bottom flask, followed by addition of tetrahydrofuran (50 ml) and N,N-dimethylformamide (0.5 ml). The system was then cooled to 0° C. with an ice-water bath, and oxalyl chloride (7.7 ml) was slowly added thereto. The reaction system was stirred at 0° C. for one hour, then returned to room temperature, and was allowed for reaction for another 14 hours. After the reaction, the system was evaporated to dry the solvent under reduced pressure to obtain a crude oil B2. LC/MS: M+H 203.99.

N-Cyclobutyl-2-fluoro-6-nitrobenzamide (B3): cyclobutylamine (9.8 ml) was added in a round bottom flask, followed by addition of tetrahydrofuran (50 ml), and N,N-diisopropylethylamine (39 ml). The system was then cooled to 0° C. with an ice-water bath, and 2-fluoro-6-nitrobenzoyl chloride (15.4 g) was slowly added thereto. The reaction system was stirred at 0° C. for one hour, then returned to room temperature, and was allowed for reaction for another 12 hours. After the reaction, the system was evaporated to dry the solvent under reduced pressure, and the resultant was diluted with water and extracted with ethyl acetate. The organic phase was washed with water and saturated brine, respectively, and dried with anhydrous sodium sulfate. The organic phase was filtered and evaporated to dryness under reduced pressure to obtain a crude product. The crude product was purified by pressurized silica gel column chromatography to obtain compound B3. LC/MS: M+H 239.09.

N-Cyclobutyl-2-fluoro-6-nitro-N-propionylbenzamide (B4): N-cyclobutyl-2-fluoro-6-nitrobenzamide (6 g) was added in a microwave reactor, followed by addition of propionic anhydride (50 ml). The reaction system was allowed for reaction at 140° C. and 150 watts for 3 hours. After the reaction, the system was diluted with methanol and evaporated to dryness under reduced pressure to obtain a black oily crude product B4. LC/MS: M+H 295.11.

3-Cyclobutyl-2-ethyl-5-fluoroquinazolin-4(3H)-one (B5): N-cyclobutyl-2-fluoro-6-nitro-N-propionylbenzamide (7.4 g) was added in a round bottom flask, followed by addition of glacial acetic acid (50 ml). The system was then cooled to 0° C. with an ice-water bath, and zinc powder (8.2 g) was slowly added thereto. The reaction system was stirred at 0° C. for one hour, then returned to room temperature, and was allowed for reaction for another 5 hours. After the reaction, the system was evaporated to dry the solvent under reduced pressure, and the resultant was diluted with saturated sodium bicarbonate and extracted with ethyl acetate. The organic phase was washed with water and saturated brine, respectively, and dried with anhydrous sodium sulfate. The organic phase was filtered and evaporated to dryness under reduced pressure to obtain a crude product. The crude product was purified by pressurized silica gel column chromatography to obtain compound B5. LC/MS: M+H 247.13.

2-(1-Bromoethyl)-3-cyclobutyl-5-fluoroquinazolin-4(3H)-one (B6): 3-cyclobutyl-2-ethyl-5-fluoroquinazolin-4(3H)-one (1.3 g) was added in a round bottom flask, followed by addition of carbon tetrachloride (30 ml), N-bromosuccinimide (1.9 g) and azobisisobutyronitrile (0.9 g). The reaction system was allowed for reaction at 100° C. for 8 hours under the protection of argon. After the reaction, the system was evaporated to dry the solvent under reduced pressure, and the resultant was diluted with water and extracted with dichloromethane. The organic phase was washed with water and saturated brine, respectively, and dried with anhydrous sodium sulfate. The organic phase was filtered and evaporated to dryness under reduced pressure to obtain a crude product. The crude product was purified by pressurized silica gel column chromatography to obtain compound B6. LC/MS: M+H 325.04.

2-(1-(4-Amino-3-(3-fluoro-4-methoxyphenyl)-1H-pyrazolo[3,4-d]pyrimidin-1-yl)ethyl)-3-cyclobutyl-5-fluoroquinazolin-4(3H)-one (1): 2-(1-bromoethyl)-3-cyclobutyl-5-fluoroquinazolin-4(3H)-one (120 mg) was added in a round bottom flask, followed by addition of N,N-dimethylformamide (2 ml), 3-(3-fluoro-4-methoxyphenyl)-1H-pyrazolo[3,4-d]pyrimidin-4-amine (96 mg) and potassium carbonate (100 mg). The reaction system was allowed for reaction for 8 hours under the protection of argon. After the reaction, the system was evaporated to dry the solvent under reduced pressure, and the resultant was diluted with water and extracted with dichloromethane. The organic phase was washed with water and saturated brine, respectively, and dried with anhydrous sodium sulfate. The organic phase was filtered and evaporated to dryness under reduced pressure to obtain a crude product. The crude product was purified by pressurized silica gel column chromatography to obtain compound 1. LC/MS: M+H 504.20.

Example 2: 2-((4-amino-3-(3-fluoro-4-methoxyphenyl)-1H-pyrazolo [3,4-d]pyrimidin-1-yl)methyl)-3-cyclohexyl-5-fluoroquinazolin-4(3H)-one

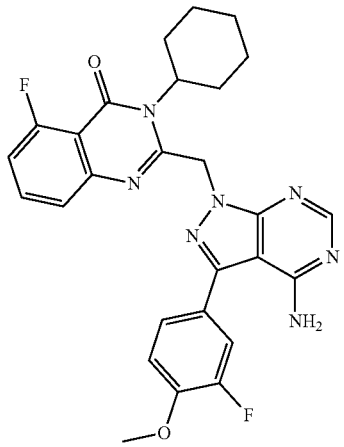 [SMILES: COc1ccc(-c2nn(Cc3nc4cccc(F)c4c(=O)n3C3CCCCC3)c3ncnc(N)c23)cc1F]

The synthesis of the compound of Example 2 was completed by using procedures similar to those described in Example 1. MS(ESI) m/z(M+1)+: 518.21.

Example 3: 2-(1-(4-amino-3-(3-fluoro-4-methoxyphenyl)-1H-pyrazolo [3,4-d]pyrimidin-1-yl)ethyl)-3-cyclohexyl-5-fluoroquinazolin-4(3H)-one

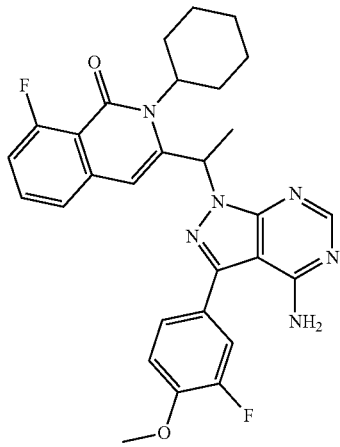 [SMILES: COc1ccc(-c2nn(C(C)c3cc4cccc(F)c4c(=O)n3C3CCCCC3)c3ncnc(N)c23)cc1F]

The synthesis of the compound of Example 3 was completed by using procedures similar to those described in Example 1. MS(ESI) m/z(M+1)+: 532.23.

Example 4: 2-((4-amino-3-(3-fluoro-4-methoxyphenyl)-1H-pyrazolo [3,4-d]pyrimidin-1-yl)methyl)-3-cyclopentyl-5-fluoroquinazolin-4(3H)-one

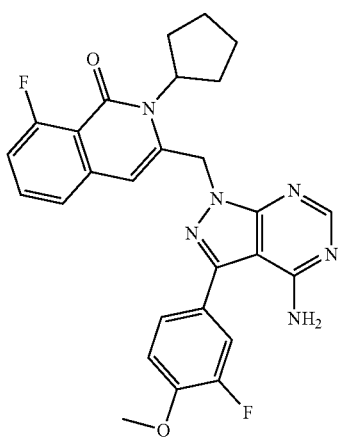 [SMILES: COc1ccc(-c2nn(Cc3cc4cccc(F)c4c(=O)n3C3CCCC3)c3ncnc(N)c23)cc1F]

The synthesis of the compound of Example 4 was completed by using procedures similar to those described in Example 1. MS(ESI) m/z(M+1)+: 504.20.

Example 5: 2-(1-(4-amino-3-(3-fluoro-4-methoxyphenyl)-1H-pyrazolo [3,4-d]pyrimidin-1-yl)ethyl)-3-cyclopentyl-5-fluoroquinazolin-4(3H)-one

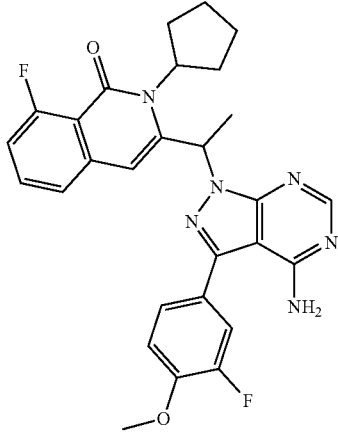 [SMILES: COc1ccc(-c2nn(C(C)c3cc4cccc(F)c4c(=O)n3C3CCCC3)c3ncnc(N)c23)cc1F]

The synthesis of the compound of Example 5 was completed by using procedures similar to those described in Example 1. MS(ESI) m/z(M+1)+: 518.21.

Example 6: 2-((4-amino-3-(3-fluoro-4-methoxyphenyl)-1H-pyrazolo [3,4-d]pyrimidin-1-yl)methyl)-3-cyclopropyl-5-fluoroquinazolin-4(3H)-one

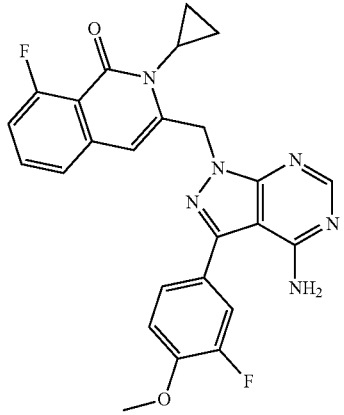 [SMILES: COc1ccc(-c2nn(Cc3cc4cccc(F)c4c(=O)n3C3CC3)c3ncnc(N)c23)cc1F]

The synthesis of the compound of Example 6 was completed by using procedures similar to those described in Example 1. MS(ESI) m/z(M+1)+: 476.17.

Example 7: 2-((4-amino-3-(3-fluoro-4-methoxyphenyl)-1H-pyrazolo [3,4-d]pyrimidin-1-yl)methyl)-3-cyclobutyl-5-fluoroquinazolin-4(3H)-one

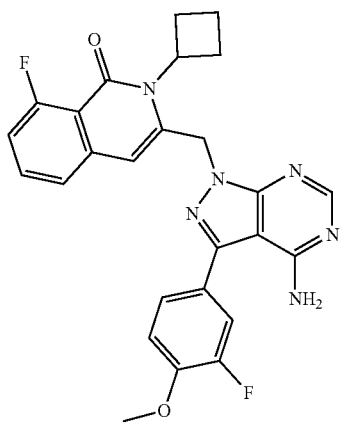 [SMILES: COc1ccc(-c2nn(Cc3cc4cccc(F)c4c(=O)n3C3CCC3)c3ncnc(N)c23)cc1F]

The synthesis of the compound of Example 7 was completed by using procedures similar to those described in Example 1. MS(ESI) m/z(M+1)+: 490.18.

Example 8: 2-(1-(4-amino-3-(3-fluoro-4-methoxyphenyl)-1H-pyrazolo [3,4-d]pyrimidin-1-yl)ethyl)-3-cyclopropyl-5-fluoroquinazolin-4(3H)-one

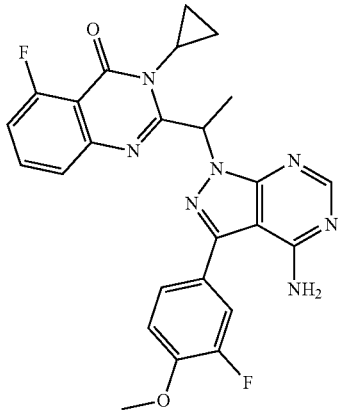 [SMILES: COc1ccc(-c2nn(C(C)c3nc4cccc(F)c4c(=O)n3C3CC3)c3ncnc(N)c23)cc1F]

The synthesis of the compound of Example 8 was completed by using procedures similar to those described in Example 1. MS(ESI) m/z(M+1)+: 490.18.

Example 9: 2-(1-(4-amino-3-(3-fluoro-4-methoxyphenyl)-1H-pyrazolo [3,4-d]pyrimidin-1-yl)propyl)-3-cyclopropyl-5-fluoroquinazolin-4(3H)-one

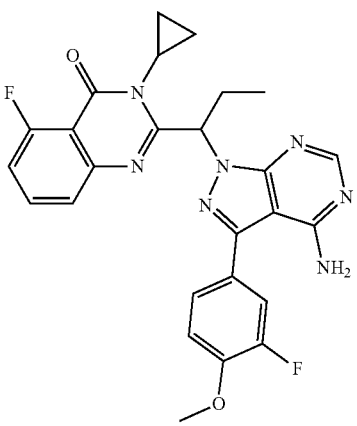 [SMILES: CCC(c1nc2cccc(F)c2c(=O)n1C1CC1)n1nc(-c2ccc(OC)c(F)c2)c2c(N)ncnc21]

The synthesis of the compound of Example 9 was completed by using procedures similar to those described in Example 1. MS(ESI) m/z(M+1)+: 504.20.

Example 10: 2-(1-(4-amino-3-(3-fluoro-4-methoxy-phenyl)-1H-pyrazolo [3,4-d]pyrimidin-1-yl)ethyl)-3-cyclopropylquinazolin-4(3H)-one

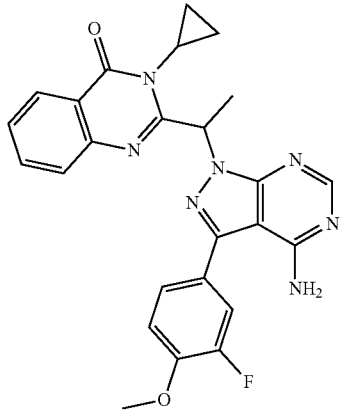 [SMILES: COc1ccc(-c2nn(C(C)c3nc4ccccc4c(=O)n3C3CC3)c3ncnc(N)c23)cc1F]

The synthesis of the compound of Example 10 was completed by using procedures similar to those described in Example 1. MS(ESI) m/z(M+1)+: 472.19.

Example 11: 2-(1-(4-amino-3-(3-fluoro-4-methoxy-phenyl)-1H-pyrazolo [3,4-d]pyrimidin-1-yl)propyl)-3-cyclopropylquinazolin-4(3H)-one

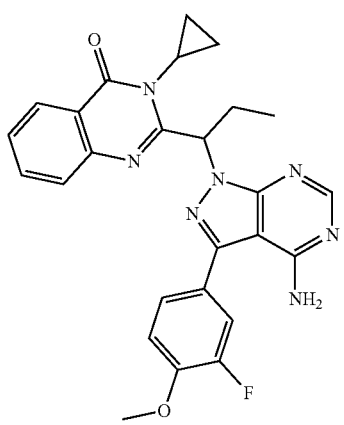 [SMILES: CCC(c1nc2ccccc2c(=O)n1C1CC1)n1nc(-c2ccc(OC)c(F)c2)c2c(N)ncnc21]

The synthesis of the compound of Example 11 was completed by using procedures similar to those described in Example 1. MS(ESI) m/z(M+1)+: 486.21.

Example 12: 2-(1-(4-amino-3-(3-fluorophenyl)-1H-pyrazolo [3,4-d]pyrimidin-1-yl)ethyl)-3-cyclopentyl-5-fluoroquinazolin-4(3H)-one

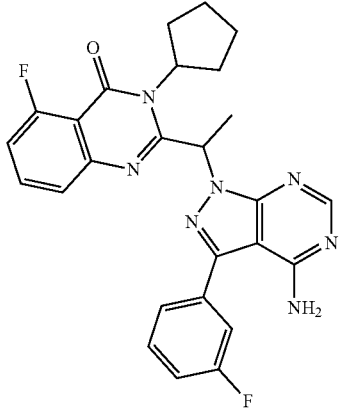 [SMILES: CC(c1nc2cccc(F)c2c(=O)n1C1CCCC1)n1nc(-c2cccc(F)c2)c2c(N)ncnc21]

The synthesis of the compound of Example 12 was completed by using procedures similar to those described in Example 1. MS(ESI) m/z(M+1)+: 488.20.

Example 13: 2-(1-(4-amino-3-phenyl-1H-pyrazolo [3,4-d]pyrimidin-1-yl)ethyl)-3-cyclopentyl-5-fluoro-quinazolin-4(3H)-one

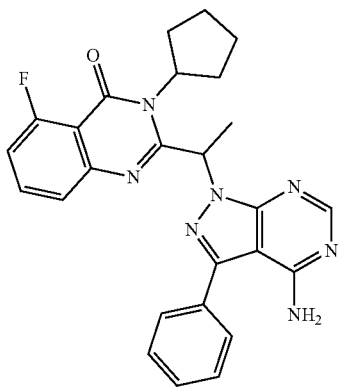 [SMILES: CC(c1nc2cccc(F)c2c(=O)n1C1CCCC1)n1nc(-c2ccccc2)c2c(N)ncnc21]

The synthesis of the compound of Example 13 was completed by using procedures similar to those described in Example 1. MS(ESI) m/z(M+1)+: 470.21.

Example 14: 2-(1-(4-amino-3-(4-methoxyphenyl)-1H-pyrazolo [3,4-d]pyrimidin-1-yl)ethyl)-3-cyclopentyl-5-fluoroquinazolin-4(3H)-one

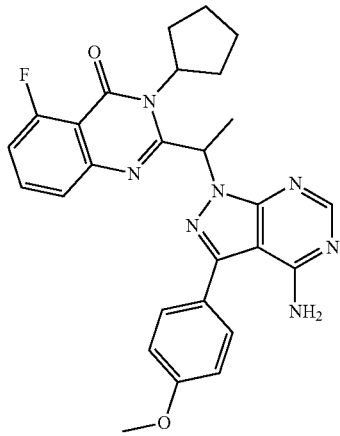 [SMILES: COc1ccc(-c2nn(C(C)c3nc4cccc(F)c4c(=O)n3C3CCCC3)c3ncnc(N)c23)cc1]

The synthesis of the compound of Example 14 was completed by using procedures similar to those described in Example 1. MS(ESI) m/z(M+1)+: 500.22.

Example 15: 2-(1-(4-amino-3-(4-isopropoxyphenyl)-1H-pyrazolo [3,4-d]pyrimidin-1-yl)ethyl)-3-cyclopentyl-5-fluoroquinazolin-4(3H)-one

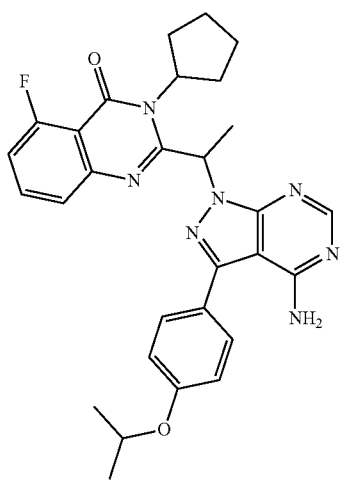 [SMILES: CC(C)Oc1ccc(-c2nn(C(C)c3nc4cccc(F)c4c(=O)n3C3CCCC3)c3ncnc(N)c23)cc1]

The synthesis of the compound of Example 15 was completed by using procedures similar to those described in Example 1. MS(ESI) m/z(M+1)+: 528.25.

Example 16: 2-(1-(4-amino-3-(3-fluorophenyl)-1H-pyrazolo [3,4-d]pyrimidin-1-yl)ethyl)-3-cyclobutyl-5-fluoroquinazolin-4(3H)-one

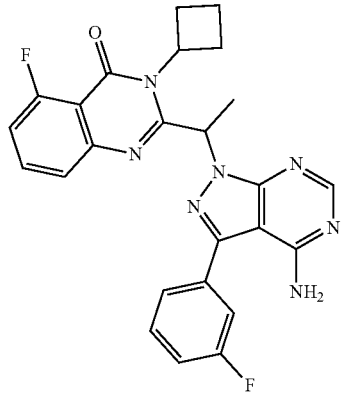 [SMILES: CC(c1nc2cccc(F)c2c(=O)n1C1CCC1)n1nc(-c2cccc(F)c2)c2c(N)ncnc21]

The synthesis of the compound of Example 16 was completed by using procedures similar to those described in Example 1. MS(ESI) m/z(M+1)+: 474.19.

Example 17: 2-(1-(4-amino-3-phenyl-1H-pyrazolo [3,4-d]pyrimidin-1-yl)ethyl)-3-cyclobutyl-5-fluoroquinazolin-4(3H)-one

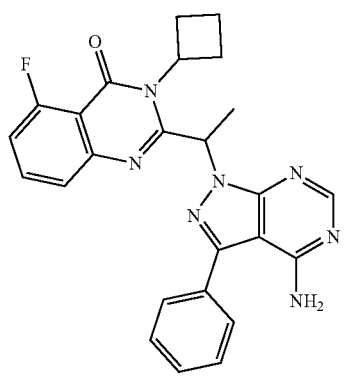 [SMILES: CC(c1nc2cccc(F)c2c(=O)n1C1CCC1)n1nc(-c2ccccc2)c2c(N)ncnc21]

The synthesis of the compound of Example 17 was completed by using procedures similar to those described in Example 1. MS(ESI) m/z(M+1)+: 456.20.

Example 18: 2-(1-(4-amino-3-(3-fluoro-4-isopropoxyphenyl)-1H-pyrazolo [3,4-d]pyrimidin-1-yl)ethyl)-3-cyclopentyl-5-fluoroquinazolin-4(3H)-one

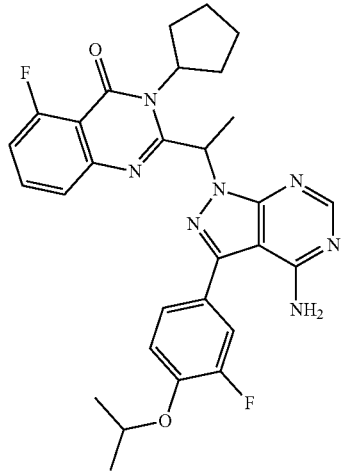 [SMILES: CC(C)Oc1ccc(-c2nn(C(C)c3nc4cccc(F)c4c(=O)n3C3CCCC3)c3ncnc(N)c23)cc1F]

The synthesis of the compound of Example 18 was completed by using procedures similar to those described in Example 1. MS(ESI) m/z(M+1)+: 546.25.

Example 19: 2-(1-(4-amino-3-(4-methoxyphenyl)-1H-pyrazolo [3,4-d]pyrimidin-1-yl)ethyl)-3-cyclobutyl-5-fluoroquinazolin-4(3H)-one

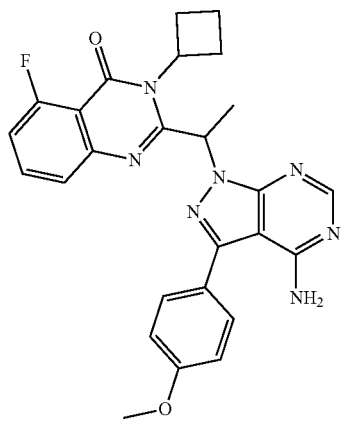 [SMILES: COc1ccc(-c2nn(C(C)c3nc4cccc(F)c4c(=O)n3C3CCC3)c3ncnc(N)c23)cc1]

The synthesis of the compound of Example 19 was completed by using procedures similar to those described in Example 1. MS(ESI) m/z(M+1)+: 486.21.

Example 20: 2-(1-(4-amino-3-(4-isopropoxyphenyl)-1H-pyrazolo [3,4-d]pyrimidin-1-yl)ethyl)-3-cyclobutyl-5-fluoroquinazolin-4(3H)-one

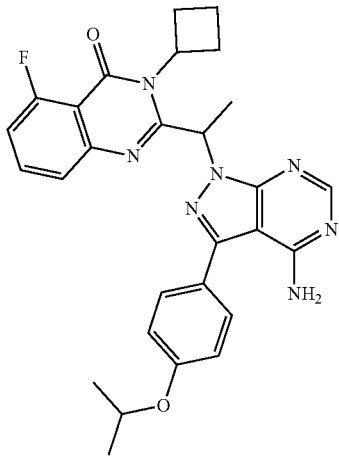 [SMILES: CC(C)Oc1ccc(-c2nn(C(C)c3nc4cccc(F)c4c(=O)n3C3CCC3)c3ncnc(N)c23)cc1]

The synthesis of the compound of Example 20 was completed by using procedures similar to those described in Example 1. MS(ESI) m/z(M+1)+: 514.24.

Example 21: 2-(1-(4-amino-3-(3-fluoro-4-isopropoxyphenyl)-1H-pyrazolo [3,4-d]pyrimidin-1-yl)ethyl)-3-cyclobutyl-5-fluoroquinazolin-4(3H)-one

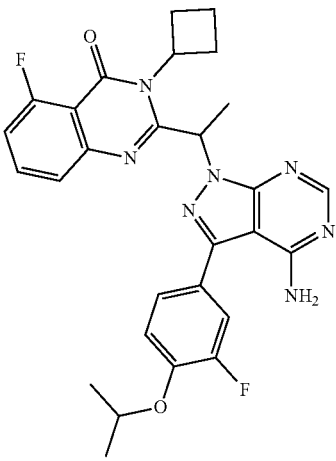 [SMILES: CC(C)Oc1ccc(-c2nn(C(C)c3nc4cccc(F)c4c(=O)n3C3CCC3)c3ncnc(N)c23)cc1F]

The synthesis of the compound of Example 21 was completed by using procedures similar to those described in Example 1. MS(ESI) m/z(M+1)+: 532.23.

Example 22: 2-(1-(4-amino-3-(3-fluoro-4-methoxy-phenyl)-1H-pyrazolo [3,4-d]pyrimidin-1-yl)ethyl)-3-cyclopropyl-6-fluoroquinazolin-4(3H)-one

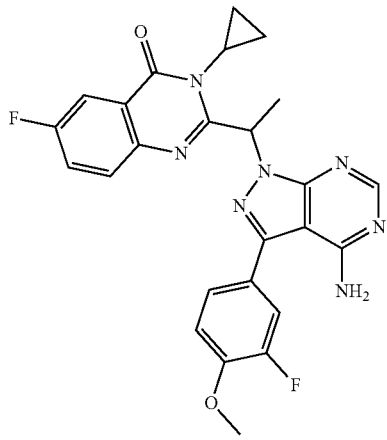 [SMILES: COc1ccc(-c2nn(C(C)c3nc4ccc(F)cc4c(=O)n3C3CC3)c3ncnc(N)c23)cc1F]

The synthesis of the compound of Example 22 was completed by using procedures similar to those described in Example 1. MS(ESI) m/z(M+1)+: 490.18.

Example 23: 2-(1-(4-amino-3-(3-fluoro-4-methoxy-phenyl)-1H-pyrazolo [3,4-d]pyrimidin-1-yl)propyl)-3-cyclopropyl-6-fluoroquinazolin-4(3H)-one

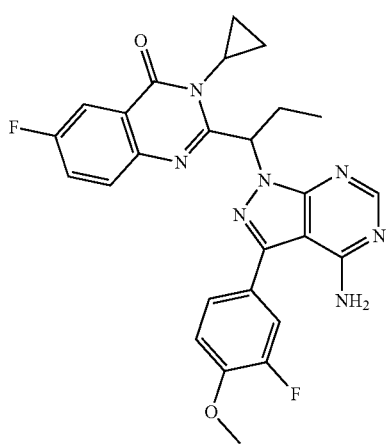 [SMILES: CCC(c1nc2ccc(F)cc2c(=O)n1C1CC1)n1nc(-c2ccc(OC)c(F)c2)c2c(N)ncnc21]

The synthesis of the compound of Example 23 was completed by using procedures similar to those described in Example 1. MS(ESI) m/z(M+1)+: 504.20.

Example 24: 2-(1-(4-amino-3-(4-isopropylphenyl)-1H-pyrazolo [3,4-d]pyrimidin-1-yl)ethyl)-3-cyclopentyl-5-fluoroquinazolin-4(3H)-one

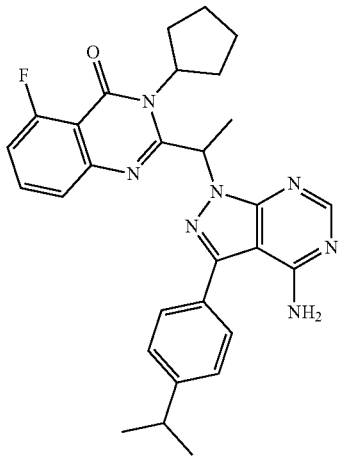 [SMILES: CC(C)c1ccc(-c2nn(C(C)c3nc4cccc(F)c4c(=O)n3C3CCCC3)c3ncnc(N)c23)cc1]

The synthesis of the compound of Example 24 was completed by using procedures similar to those described in Example 1. MS(ESI) m/z(M+1)+: 512.26.

Example 25: 2-(1-(4-amino-3-(3-fluoro-4-methylphenyl)-1H-pyrazolo [3,4-d]pyrimidin-1-yl)ethyl)-3-cyclopentyl-5-fluoroquinazolin-4(3H)-one

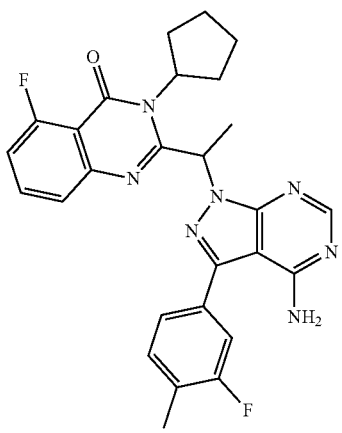 [SMILES: Cc1ccc(-c2nn(C(C)c3nc4cccc(F)c4c(=O)n3C3CCCC3)c3ncnc(N)c23)cc1F]

The synthesis of the compound of Example 25 was completed by using procedures similar to those described in Example 1. MS(ESI) m/z(M+1)+: 502.22.

Example 26: 2-(1-(4-amino-3-(quinolin-3-yl)-1H-pyrazolo [3,4-d]pyrimidin-1-yl)ethyl)-3-cyclopentyl-5-fluoroquinazolin-4(3H)-one

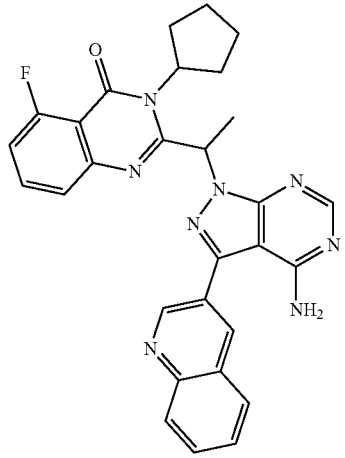 [SMILES: CC(c1nc2cccc(F)c2c(=O)n1C1CCCC1)n1nc(-c2cnc3ccccc3c2)c2c(N)ncnc21]

The synthesis of the compound of Example 26 was completed by using procedures similar to those described in Example 1. MS(ESI) m/z(M+1)+: 521.22.

Example 27: 2-(1-(4-amino-3-(3,4-dimethoxyphenyl)-1H-pyrazolo [3,4-d]pyrimidin-1-yl)ethyl)-3-cyclobutyl-5-fluoroquinazolin-4(3H)-one

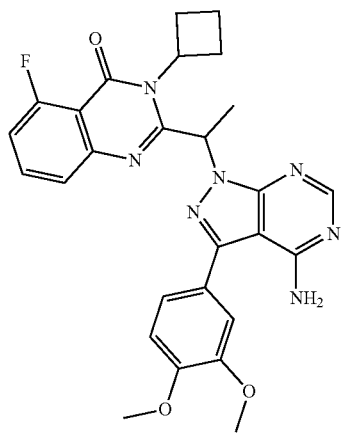 [SMILES: COc1ccc(-c2nn(C(C)c3nc4cccc(F)c4c(=O)n3C3CCC3)c3ncnc(N)c23)cc1OC]

The synthesis of the compound of Example 27 was completed by using procedures similar to those described in Example 1. MS(ESI) m/z(M+1)+: 516.22.

Example 28: 2-(1-(4-amino-3-(4-isopropylphenyl)-1H-pyrazolo [3,4-d]pyrimidin-1-yl)ethyl)-3-cyclobutyl-5-fluoroquinazolin-4(3H)-one

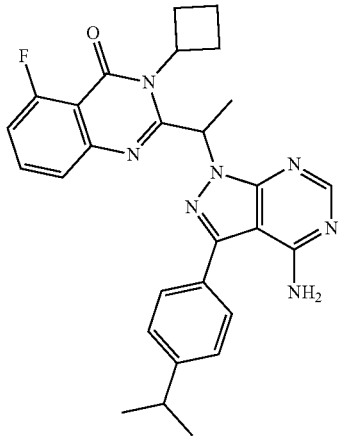 [SMILES: CC(C)c1ccc(-c2nn(C(C)c3nc4cccc(F)c4c(=O)n3C3CCC3)c3ncnc(N)c23)cc1]

The synthesis of the compound of Example 28 was completed by using procedures similar to those described in Example 1. MS(ESI) m/z(M+1)+: 498.24.

Example 29: 2-(1-(4-amino-3-(3-fluoro-4-methoxyphenyl)-1H-pyrazolo [3,4-d]pyrimidin-1-yl)ethyl)-8-chloro-3-cyclobutylquinazolin-4(3H)-one

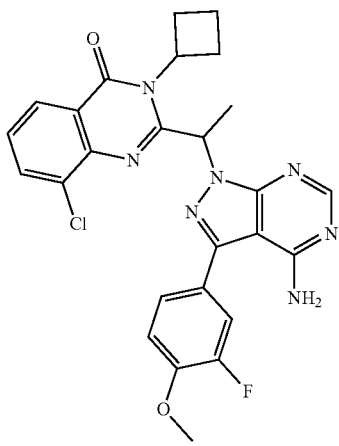 [SMILES: COc1ccc(-c2nn(C(C)c3nc4c(Cl)cccc4c(=O)n3C3CCC3)c3ncnc(N)c23)cc1F]

The synthesis of the compound of Example 29 was completed by using procedures similar to those described in Example 1. MS(ESI) m/z(M+1)+: 520.17.

Example 30: 2-(1-(4-amino-3-(3-fluoro-4-methoxyphenyl)-1H-pyrazolo [3,4-d]pyrimidin-1-yl)ethyl)-8-chloro-3-cyclopentylquinazolin-4(3H)-one

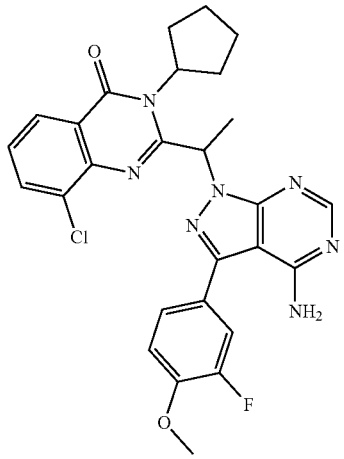 [SMILES: COc1ccc(-c2nn(C(C)c3nc4c(Cl)cccc4c(=O)n3C3CCCC3)c3ncnc(N)c23)cc1F]

The synthesis of the compound of Example 30 was completed by using procedures similar to those described in Example 1. MS(ESI) m/z(M+1)+: 534.18.

Example 31: 2-(1-(4-amino-3-(4-methoxyphenyl)-1H-pyrazolo [3,4-d]pyrimidin-1-yl)ethyl)-8-chloro-3-cyclopentylquinazolin-4(3H)-one

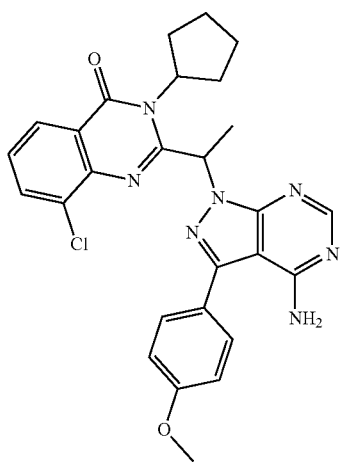 [SMILES: COc1ccc(-c2nn(C(C)c3nc4c(Cl)cccc4c(=O)n3C3CCCC3)c3ncnc(N)c23)cc1]

The synthesis of the compound of Example 31 was completed by using procedures similar to those described in Example 1. MS(ESI) m/z(M+1)+: 516.19.

Example 32: 2-(1-(4-amino-3-(4-methoxy-3-methylphenyl)-1H-pyrazolo [3,4-d]pyrimidin-1-yl)ethyl)-8-chloro-3-cyclopentylquinazolin-4(3H)-one

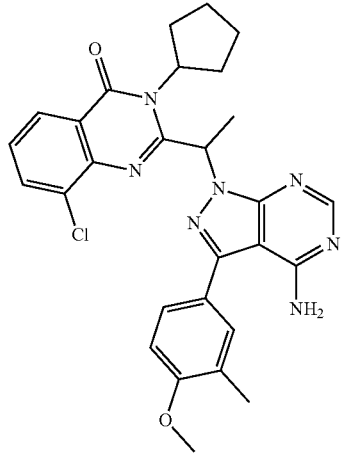 [SMILES: COc1ccc(-c2nn(C(C)c3nc4c(Cl)cccc4c(=O)n3C3CCCC3)c3ncnc(N)c23)cc1C]

The synthesis of the compound of Example 32 was completed by using procedures similar to those described in Example 1. MS(ESI) m/z(M+1)+: 530.21.

Example 33: 2-(1-(4-amino-3-(3-fluoro-4-methoxyphenyl)-1H-pyrazolo[3,4-d]pyrimidin-1-yl)ethyl)-3-cyclopentyl-6-fluoroquinazolin-4-(3H)-one

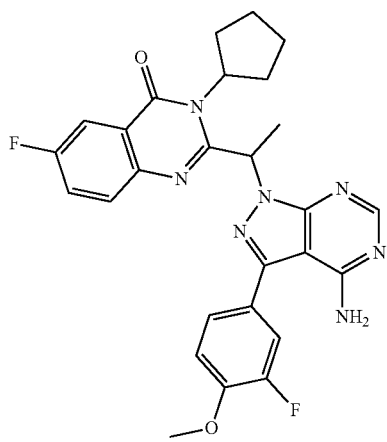 [SMILES: COc1ccc(-c2nn(C(C)c3nc4ccc(F)cc4c(=O)n3C3CCCC3)c3ncnc(N)c23)cc1F]

The synthesis of the compound of Example 33 was completed by using procedures similar to those described in Example 1. MS(ESI) m/z(M+1)+: 518.21.

Example 34: 2-(1-(4-amino-3-(4-methoxy-3-methylphenyl)-1H-pyrazolo [3,4-d]pyrimidin-1-yl)ethyl)-3-cyclobutyl-5-fluoroquinazolin-4(3H)-one

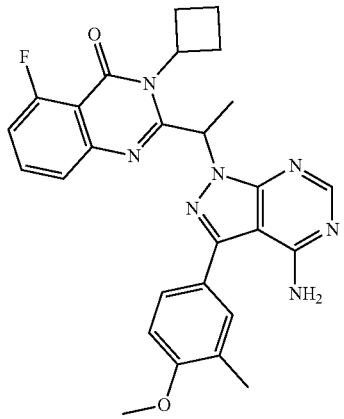 [SMILES: COc1ccc(-c2nn(C(C)c3nc4cccc(F)c4c(=O)n3C3CCC3)c3ncnc(N)c23)cc1C]

The synthesis of the compound of Example 34 was completed by using procedures similar to those described in Example 1. MS(ESI) m/z(M+1)+: 500.22.

Example 35: 2-(1-(4-amino-3-(benzo[d][1,3]dioxol-5-yl)-1H-pyrazolo [3,4-d]pyrimidin-1-yl)ethyl)-3-cyclobutyl-5-fluoroquinazolin-4(3H)-one

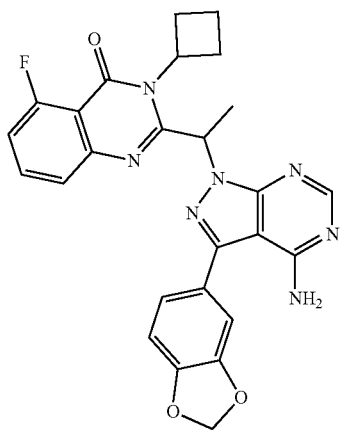 [SMILES: CC(c1nc2cccc(F)c2c(=O)n1C1CCC1)n1nc(-c2ccc3c(c2)OCO3)c2c(N)ncnc21]

The synthesis of the compound of Example 35 was completed by using procedures similar to those described in Example 1. MS(ESI) m/z(M+1)+: 500.19.

Example 36: 2-(1-(4-amino-3-(4-methoxy-3-methylphenyl)-1H-pyrazolo [3,4-d]pyrimidin-1-yl)ethyl)-3-cyclopentyl-5-fluoroquinazolin-4(3H)-one

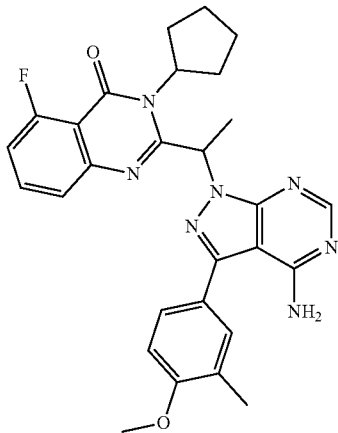 [SMILES: COc1ccc(-c2nn(C(C)c3nc4cccc(F)c4c(=O)n3C3CCCC3)c3ncnc(N)c23)cc1C]

The synthesis of the compound of Example 36 was completed by using procedures similar to those described in Example 1. MS(ESI) m/z(M+1)+: 514.24.

Example 37: 2-(1-(4-amino-3-(4-methoxyphenyl)-1H-pyrazolo [3,4-d]pyrimidin-1-yl)ethyl)-3-cyclobutylquinazolin-4(3H)-one

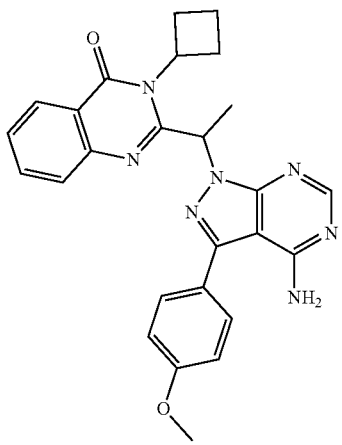 [SMILES: COc1ccc(-c2nn(C(C)c3nc4ccccc4c(=O)n3C3CCC3)c3ncnc(N)c23)cc1]

The synthesis of the compound of Example 37 was completed by using procedures similar to those described in Example 1. MS(ESI) m/z(M+1)+: 468.22.

Example 38: 2-(1-(4-amino-3-(3,4-dimethoxyphe-nyl)-1H-pyrazolo [3,4-d]pyrimidin-1-yl)ethyl)-3-cyclobutylquinazolin-4(3H)-one

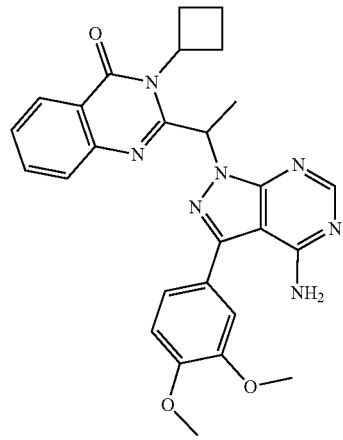 [SMILES: COc1ccc(-c2nn(C(C)c3nc4ccccc4c(=O)n3C3CCC3)c3ncnc(N)c23)cc1OC]

The synthesis of the compound of Example 38 was completed by using procedures similar to those described in Example 1. MS(ESI) m/z(M+1)+: 498.23.

Example 39: 2-(1-(4-amino-3-(4-methoxy-3-meth-ylphenyl)-1H-pyrazolo [3,4-d]pyrimidin-1-yl)ethyl)-3-cyclobutylquinazolin-4(3H)-one

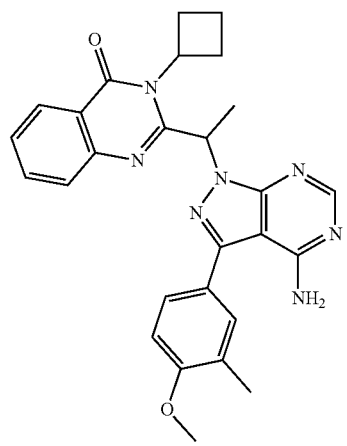 [SMILES: COc1ccc(-c2nn(C(C)c3nc4ccccc4c(=O)n3C3CCC3)c3ncnc(N)c23)cc1C]

The synthesis of the compound of Example 39 was completed by using procedures similar to those described in Example 1. MS(ESI) m/z(M+1)+: 482.23.

Example 40: 2-(1-(4-amino-3-(4-methoxyphenyl)-1H-pyrazolo [3,4-d]pyrimidin-1-yl)propyl)-3-cyclo-propyl-5-fluoroquinazolin-4(3H)-one

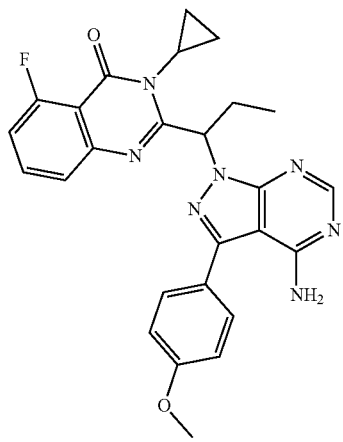 [SMILES: CCC(c1nc2cccc(F)c2c(=O)n1C1CC1)n1nc(-c2ccc(OC)cc2)c2c(N)ncnc21]

The synthesis of the compound of Example 40 was completed by using procedures similar to those described in Example 1. MS(ESI) m/z(M+1)+: 486.21.

Example 41: 2-(1-(4-amino-3-(4-methoxy-3-meth-ylphenyl)-1H-pyrazolo [3,4-d]pyrimidin-1-yl)ethyl)-3-cyclopropyl-6-fluoroquinazolin-4-(3H)-one

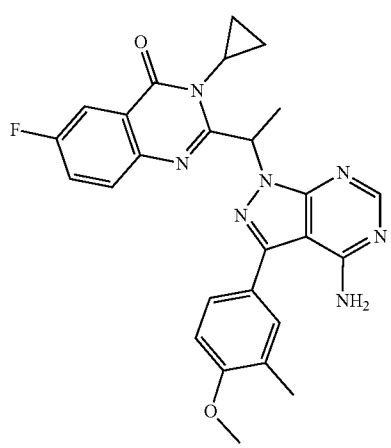 [SMILES: COc1ccc(-c2nn(C(C)c3nc4ccc(F)cc4c(=O)n3C3CC3)c3ncnc(N)c23)cc1C]

The synthesis of the compound of Example 41 was completed by using procedures similar to those described in Example 1. MS(ESI) m/z(M+1)+: 486.21.

Example 42: 2-(1-(4-amino-3-(4-methoxyphenyl)-1H-pyrazolo [3,4-d]pyrimidin-1-yl)ethyl)-3-cyclopropyl-6-fluoroquinazolin-4(3H)-one

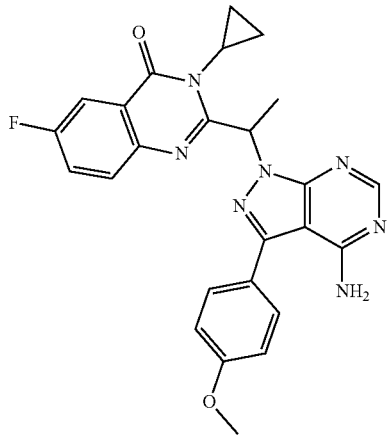 [SMILES: COc1ccc(-c2nn(C(C)c3nc4ccc(F)cc4c(=O)n3C3CC3)c3ncnc(N)c23)cc1]

The synthesis of the compound of Example 42 was completed by using procedures similar to those described in Example 1. MS(ESI) m/z(M+1)+: 472.19.

Example 43: 2-(1-(4-amino-3-(3-fluoro-4-methylphenyl)-1H-pyrazolo [3,4-d]pyrimidin-1-yl)ethyl)-3-cyclopropyl-6-fluoroquinazolin-4-(3H)-one

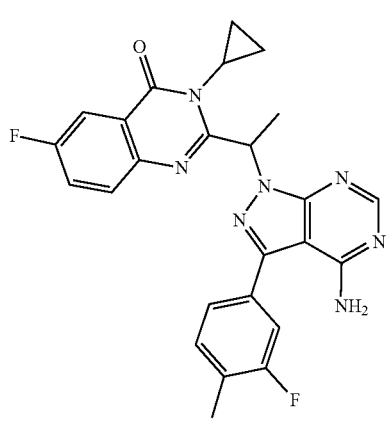 [SMILES: Cc1ccc(-c2nn(C(C)c3nc4ccc(F)cc4c(=O)n3C3CC3)c3ncnc(N)c23)cc1F]

The synthesis of the compound of Example 43 was completed by using procedures similar to those described in Example 1. MS(ESI) m/z(M+1)+: 474.19.

Example 44: 2-(1-(4-amino-3-(4-methoxy-3-methylphenyl)-1H-pyrazolo [3,4-d]pyrimidin-1-yl)ethyl)-3-cyclopropylquinazolin-4(3H)-one

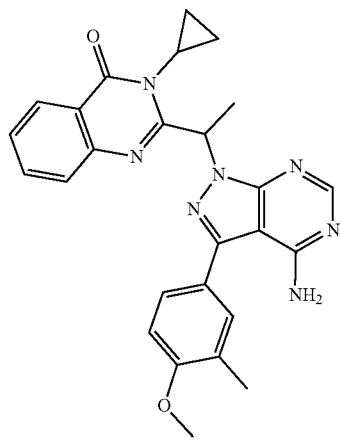 [SMILES: COc1ccc(-c2nn(C(C)c3nc4ccccc4c(=O)n3C3CC3)c3ncnc(N)c23)cc1C]

The synthesis of the compound of Example 44 was completed by using procedures similar to those described in Example 1. MS(ESI) m/z(M+1)+: 468.22.

Example 45: 2-(1-(4-amino-3-(4-methoxyphenyl)-1H-pyrazolo [3,4-d]pyrimidin-1-yl)ethyl)-3-cyclopropylquinazolin-4(3H)-one

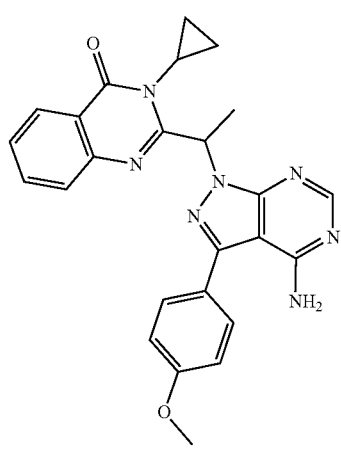 [SMILES: COc1ccc(-c2nn(C(C)c3nc4ccccc4c(=O)n3C3CC3)c3ncnc(N)c23)cc1]

The synthesis of the compound of Example 45 was completed by using procedures similar to those described in Example 1. MS(ESI) m/z(M+1)+: 454.20.

Example 46: 2-(1-(4-amino-3-(benzo[d][1,3]dioxol-5-yl)-1H-pyrazolo [3,4-d]pyrimidin-1-yl)ethyl)-3-cyclopentyl-5-fluoroquinazolin-4(3H)-one

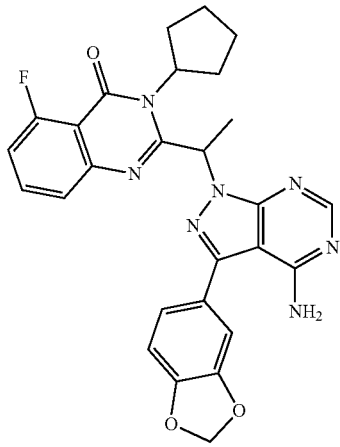 [SMILES: CC(c1nc2cccc(F)c2c(=O)n1C1CCCC1)n1nc(-c2ccc3c(c2)OCO3)c2c(N)ncnc21]

The synthesis of the compound of Example 46 was completed by using procedures similar to those described in Example 1. MS(ESI) m/z(M+1)+: 514.20.

Example 47: 2-(1-(4-amino-3-(3,4-dimethoxyphenyl)-1H-pyrazolo [3,4-d]pyrimidin-1-yl)propyl)-3-cyclopropyl-5-fluoroquinazolin-4(3H)-one

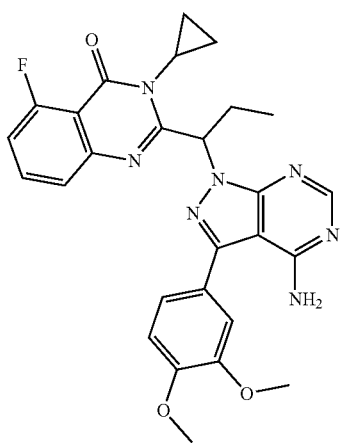 [SMILES: CCC(c1nc2cccc(F)c2c(=O)n1C1CC1)n1nc(-c2ccc(OC)c(OC)c2)c2c(N)ncnc21]

The synthesis of the compound of Example 47 was completed by using procedures similar to those described in Example 1. MS(ESI) m/z(M+1)+: 516.22.

Example 48: 4-(4-amino-1-(1-(3-cyclopropyl-5-fluoro-4-oxo-3,4-dihydroquinazolin-2-yl)propyl)-1H-pyrazolo[3,4-d]pyrimidin-3-yl)-N-methylbenzamide

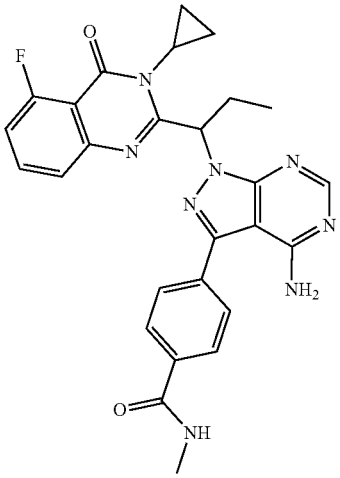 [SMILES: CCC(c1nc2cccc(F)c2c(=O)n1C1CC1)n1nc(-c2ccc(C(=O)NC)cc2)c2c(N)ncnc21]

The synthesis of the compound of Example 48 was completed by using procedures similar to those described in Example 1. MS(ESI) m/z(M+1)+: 513.22.

Example 49: N-(4-(4-amino-1-(1-(3-cyclopropyl-5-fluoro-4-oxo-3,4-dihydroquinazolin-2-yl)propyl)-1H-pyrazolo[3,4-d]pyrimidin-3-yl)phenyl)acetamide

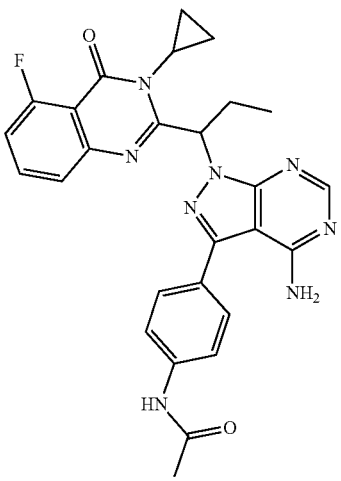 [SMILES: CCC(c1nc2cccc(F)c2c(=O)n1C1CC1)n1nc(-c2ccc(NC(C)=O)cc2)c2c(N)ncnc21]

The synthesis of the compound of Example 49 was completed by using procedures similar to those described in Example 1. MS(ESI) m/z(M+1)+: 513.22.

Example 50: 2-(1-(4-amino-3-(6-methoxypyridin-3-yl)-1H-pyrazolo [3,4-d]pyrimidin-1-yl)propyl)-3-cyclopropyl-5-fluoroquinazolin-4(3H)-one

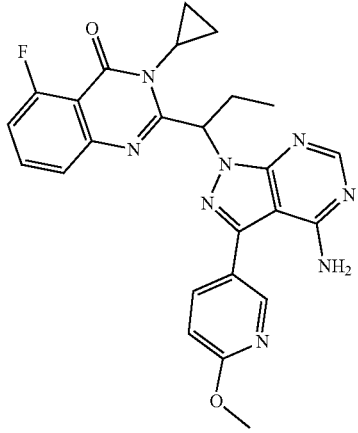 [SMILES: CCC(c1nc2cccc(F)c2c(=O)n1C1CC1)n1nc(-c2ccc(OC)nc2)c2c(N)ncnc21]

The synthesis of the compound of Example 50 was completed by using procedures similar to those described in Example 1. MS(ESI) m/z(M+1)+: 487.20.

Example 51: 2-(1-(4-amino-3-(benzo[d][1,3]dioxol-5-yl)-1H-pyrazolo [3,4-d]pyrimidin-1-yl)propyl)-3-cyclopropyl-5-fluoroquinazolin-4(3H)-one

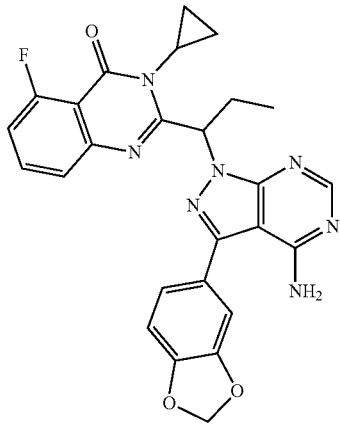 [SMILES: CCC(c1nc2cccc(F)c2c(=O)n1C1CC1)n1nc(-c2ccc3c(c2)OCO3)c2c(N)ncnc21]

The synthesis of the compound of Example 51 was completed by using procedures similar to those described in Example 1. MS(ESI) m/z(M+1)+: 500.18.

Example 52: 4-(4-amino-1-(1-(3-cyclobutyl-5-fluoro-4-oxo-3,4-dihydroquinazolin-2-yl)ethyl)-1H-pyrazolo[3,4-d]pyrimidinepyridin-3-yl)-N-methyl-benzamide

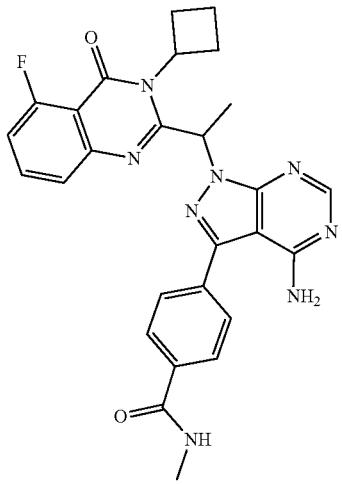 [SMILES: CNC(=O)c1ccc(-c2nn(C(C)c3nc4cccc(F)c4c(=O)n3C3CCC3)c3ncnc(N)c23)cc1]

The synthesis of the compound of Example 52 was completed by using procedures similar to those described in Example 1. MS(ESI) m/z(M+1)+: 513.21.

Example 53: N-(4-(4-amino-1-(1-(3-cyclobutyl-5-fluoro-4-oxo-3,4-dihydro quinazolin-2-yl)ethyl)-1H-pyrazolo[3,4-d]pyrimidin-3-yl)phenyl)acetamide

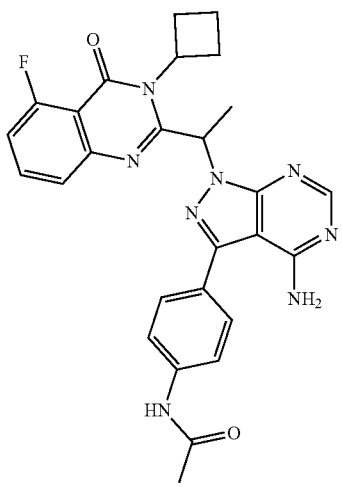 [SMILES: CC(=O)Nc1ccc(-c2nn(C(C)c3nc4cccc(F)c4c(=O)n3C3CCC3)c3ncnc(N)c23)cc1]

The synthesis of the compound of Example 53 was completed by using procedures similar to those described in Example 1. MS(ESI) m/z(M+1)+: 513.21.

Example 54: 2-(1-(4-amino-3-(6-methoxypyridin-3-yl)-1H-pyrazolo [3,4-d]pyrimidin-1-yl)ethyl)-3-cyclobutyl-5-fluoroquinazolin-4(3H)-one

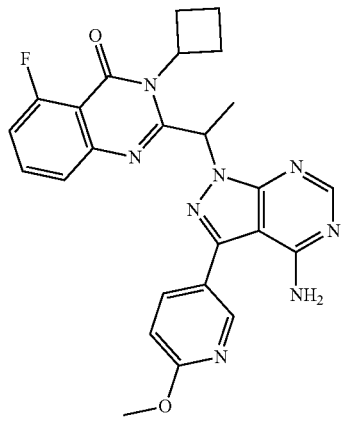 [SMILES: COc1ccc(-c2nn(C(C)c3nc4cccc(F)c4c(=O)n3C3CCC3)c3ncnc(N)c23)cn1]

The synthesis of the compound of Example 54 was completed by using procedures similar to those described in Example 1. MS(ESI) m/z(M+1)+: 487.20.

Example 55: 2-(1-(4-amino-3-(4-ethylphenyl)-1H-pyrazolo [3,4-d]pyrimidin-1-yl)ethyl)-3-cyclobutyl-5-fluoroquinazolin-4(3H)-one

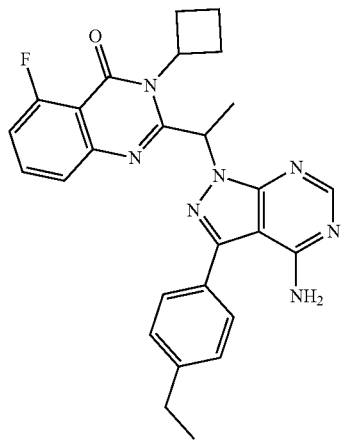 [SMILES: CCc1ccc(-c2nn(C(C)c3nc4cccc(F)c4c(=O)n3C3CCC3)c3ncnc(N)c23)cc1]

The synthesis of the compound of Example 55 was completed by using procedures similar to those described in Example 1. MS(ESI) m/z(M+1)+: 484.22.

Example 56: 2-(1-(4-amino-3-(3-fluoro-4-methoxyphenyl)-1H-pyrazolo [3,4-d]pyrimidin-1-yl)propyl)-3-cyclopropyl-6,7-difluoroquinazolin-4(3H)-one

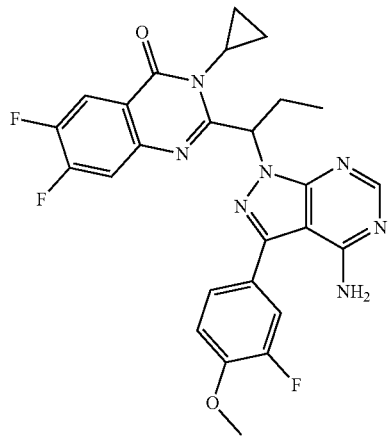 [SMILES: CCC(c1nc2cc(F)c(F)cc2c(=O)n1C1CC1)n1nc(-c2ccc(OC)c(F)c2)c2c(N)ncnc21]

The synthesis of the compound of Example 56 was completed by using procedures similar to those described in Example 1. MS(ESI) m/z(M+1)+: 522.18.

Example 57: 4-(4-amino-1-(1-(3-cyclopropyl-6,7-difluoro-4-oxo-3,4-dihydroquinazolin-2-yl)propyl)-1H-pyrazolo[3,4-d]pyrimidin-3-yl)-N-methylbenzamide

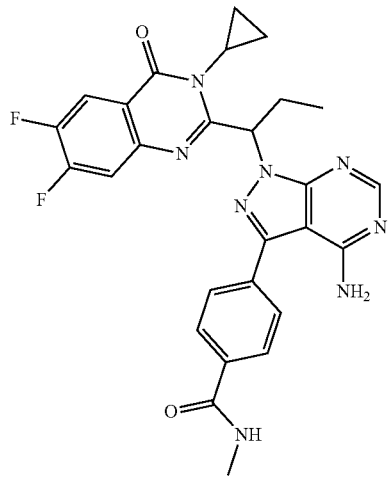 [SMILES: CCC(c1nc2cc(F)c(F)cc2c(=O)n1C1CC1)n1nc(-c2ccc(C(=O)NC)cc2)c2c(N)ncnc21]

The synthesis of the compound of Example 57 was completed by using procedures similar to those described in Example 1. MS(ESI) m/z(M+1)+: 531.20.

Example 58: 2-(1-(4-amino-3-(3-fluoro-4-methoxy-phenyl)-1H-pyrazolo [3,4-d]pyrimidin-1-yl)ethyl)-3-cyclopropyl-7-(trifluoromethyl)quinazolin-4(3H)-one

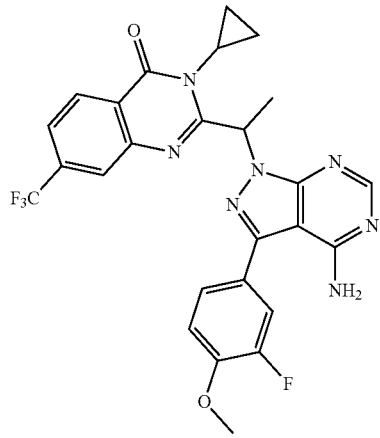

The synthesis of the compound of Example 58 was completed by using procedures similar to those described in Example 1. MS(ESI) m/z(M+1)+: 540.17.

Example 59: 2-(1-(4-amino-3-(4-methoxyphenyl)-1H-pyrazolo [3,4-d]pyrimidin-1-yl)ethyl)-3-cyclo-propyl-7-(trifluoromethyl)quinazolin-4(3H)-one

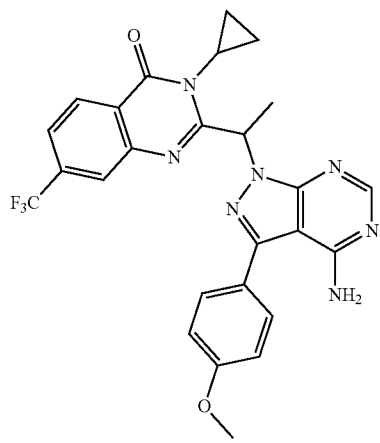 [SMILES: COc1ccc(-c2nn(C(C)c3nc4cc(C(F)(F)F)ccc4c(=O)n3C3CC3)c3ncnc(N)c23)cc1]

The synthesis of the compound of Example 59 was completed by using procedures similar to those described in Example 1. MS(ESI) m/z(M+1)+: 522.18.

Example 60: 2-(1-(4-amino-3-(3,4-dimethoxyphe-nyl)-1H-pyrazolo [3,4-d]pyrimidin-1-yl)ethyl)-3-cyclopropyl-7-(trifluoromethyl)quinazolin-4(3H)-one

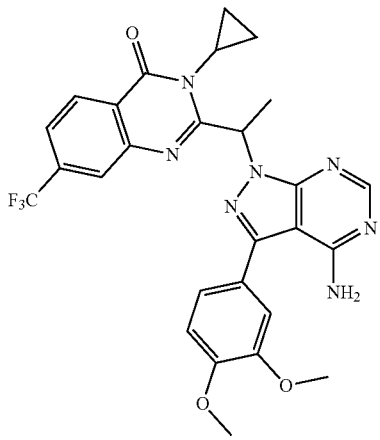 [SMILES: COc1ccc(-c2nn(C(C)c3nc4cc(C(F)(F)F)ccc4c(=O)n3C3CC3)c3ncnc(N)c23)cc1OC]

The synthesis of the compound of Example 60 was completed by using procedures similar to those described in Example 1. MS(ESI) m/z(M+1)+: 552.53.

Example 61: 2-(1-(4-amino-3-(4-methoxy-3-meth-ylphenyl)-1H-pyrazolo [3,4-d]pyrimidin-1-yl)pro-pyl)-3-cyclopropyl-5-fluoroquinazolin-4(3H)-one

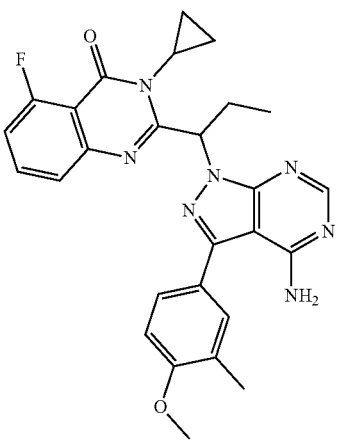 [SMILES: CCC(c1nc2cccc(F)c2c(=O)n1C1CC1)n1nc(-c2ccc(OC)c(C)c2)c2c(N)ncnc21]

The synthesis of the compound of Example 61 was completed by using procedures similar to those described in Example 1. MS(ESI) m/z(M+1)+: 500.22.

Example 62: N-(4-(4-amino-1-(1-(3-cyclopropyl-6,7-difluoro-4-oxo-3,4-dihydroquinazolin-2-yl)propyl)-1H-pyrazolo[3,4-d]pyrimidin-3-yl)phenyl)acetamide

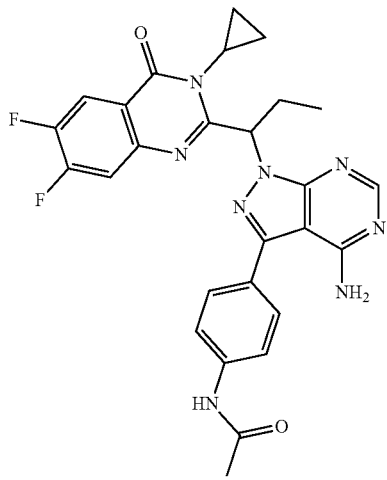 [SMILES: CCC(c1nc2cc(F)c(F)cc2c(=O)n1C1CC1)n1nc(-c2ccc(NC(C)=O)cc2)c2c(N)ncnc21]

The synthesis of the compound of Example 62 was completed by using procedures similar to those described in Example 1. MS(ESI) m/z(M+1)+: 531.20.

Example 63: 2-(1-(4-amino-3-(4-methoxyphenyl)-1H-pyrazolo[3,4-d]pyrimidin-1-yl)propyl)-3-cyclopropyl-6-fluoroquinazolin-4(3H)-one

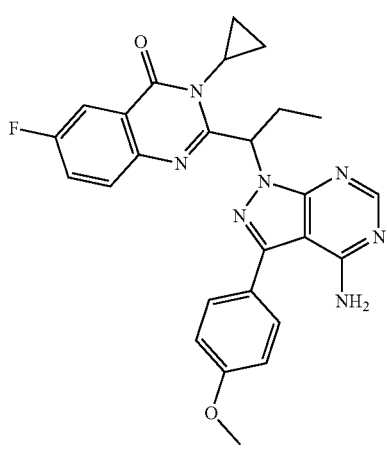 [SMILES: CCC(c1nc2ccc(F)cc2c(=O)n1C1CC1)n1nc(-c2ccc(OC)cc2)c2c(N)ncnc21]

The synthesis of the compound of Example 63 was completed by using procedures similar to those described in Example 1. MS(ESI) m/z(M+1)+: 486.20.

Example 64: 2-(1-(4-amino-3-(3,4-dimethoxyphenyl)-1H-pyrazolo[3,4-d]pyrimidin-1-yl)propyl)-3-cyclopropyl-6-fluoroquinazolin-4(3H)-one

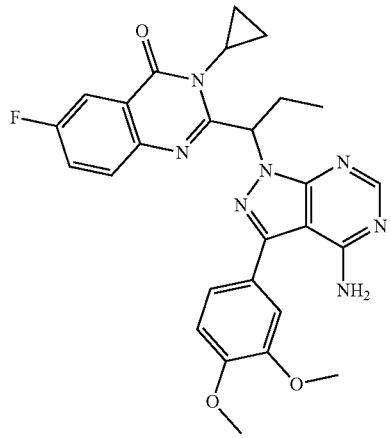 [SMILES: CCC(c1nc2ccc(F)cc2c(=O)n1C1CC1)n1nc(-c2ccc(OC)c(OC)c2)c2c(N)ncnc21]

The synthesis of the compound of Example 64 was completed by using procedures similar to those described in Example 1. MS(ESI) m/z(M+1)+: 516.21.

Example 65: 4-(4-amino-1-(1-(3-cyclopropyl-6-fluoro-4-oxo-3,4-dihydroquinazolin-2-yl)propyl)-1H-pyrazolo[3,4-d]pyrimidin-3-yl)-N-methylbenzamide

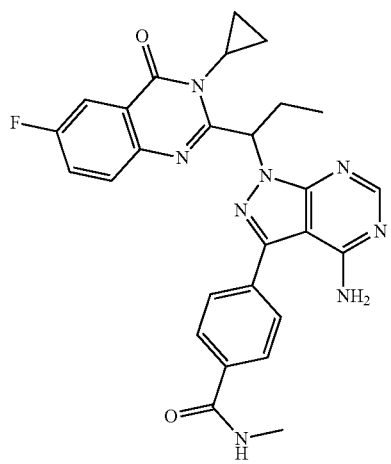 [SMILES: CCC(c1nc2ccc(F)cc2c(=O)n1C1CC1)n1nc(-c2ccc(C(=O)NC)cc2)c2c(N)ncnc21]

The synthesis of the compound of Example 65 was completed by using procedures similar to those described in Example 1. MS(ESI) m/z(M+1)+: 513.21.

Example 66: N-(4-(4-amino-1-(1-(3-cyclopropyl-6-fluoro-4-oxo-3,4-dihydroquinazolin-2-yl)propyl)-1H-pyrazolo[3,4-d]pyrimidin-3-yl)phenyl)acetamide

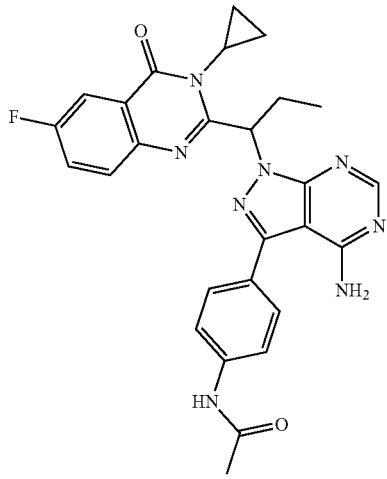 [SMILES: CCC(c1nc2ccc(F)cc2c(=O)n1C1CC1)n1nc(-c2ccc(NC(C)=O)cc2)c2c(N)ncnc21]

The synthesis of the compound of Example 66 was completed by using procedures similar to those described in Example 1. MS(ESI) m/z(M+1)+: 513.21.

Example 67: 2-(1-(4-amino-3-(6-methoxypyridin-3-yl)-1H-pyrazolo[3,4-d]pyrimidin-1-yl)propyl)-3-cyclopropyl-6-fluoroquinazolin-4-(3H)-one

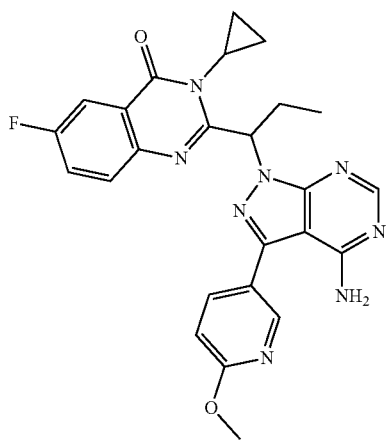 [SMILES: CCC(c1nc2ccc(F)cc2c(=O)n1C1CC1)n1nc(-c2ccc(OC)nc2)c2c(N)ncnc21]

The synthesis of the compound of Example 67 was completed by using procedures similar to those described in Example 1. MS(ESI) m/z(M+1)+: 487.20.

Example 68: 4-(4-amino-1-(1-(3-cyclobutyl-4-oxo-3,4-dihydroquinazolin-2-yl)ethyl)-1H-pyrazolo [3,4-d]pyrimidin-3-yl)-N-methylbenzamide

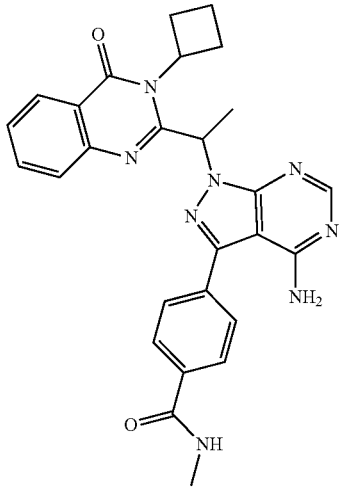 [SMILES: CNC(=O)c1ccc(-c2nn(C(C)c3nc4ccccc4c(=O)n3C3CCC3)c3ncnc(N)c23)cc1]

The synthesis of the compound of Example 68 was completed by using procedures similar to those described in Example 1. MS(ESI) m/z(M+1)+: 495.22.

Example 69: N-(4-(4-amino-1-(1-(3-cyclobutyl-4-oxo-3,4-dihydro quinazolin-2-yl)ethyl)-1H-pyrazolo [3,4-d]pyrimidin-3-yl)phenyl)acetamide

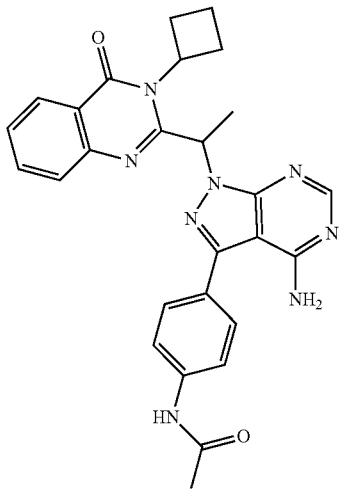 [SMILES: CC(=O)Nc1ccc(-c2nn(C(C)c3nc4ccccc4c(=O)n3C3CCC3)c3ncnc(N)c23)cc1]

The synthesis of the compound of Example 69 was completed by using procedures similar to those described in Example 1. MS(ESI) m/z(M+1)+: 495.22.

Example 70: 2-(1-(4-amino-3-(6-methoxypyridin-3-yl)-1H-pyrazolo [3,4-d]pyrimidin-1-yl)ethyl)-3-cyclobutylquinazolin-4(3H)-one

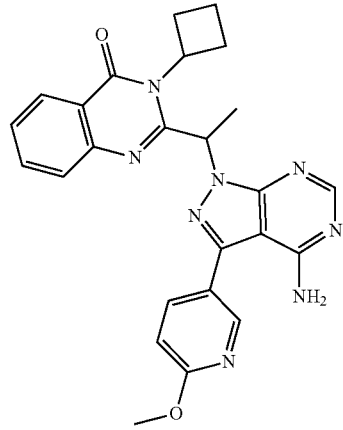 [SMILES: COc1ccc(-c2nn(C(C)c3nc4ccccc4c(=O)n3C3CCC3)c3ncnc(N)c23)cn1]

The synthesis of the compound of Example 70 was completed by using procedures similar to those described in Example 1. MS(ESI) m/z(M+1)+: 469.21.

Example 71: 2-(1-(4-amino-3-(3-methoxyphenyl)-1H-pyrazolo [3,4-d]pyrimidin-1-yl)ethyl)-3-cyclobutylquinazolin-4(3H)-one

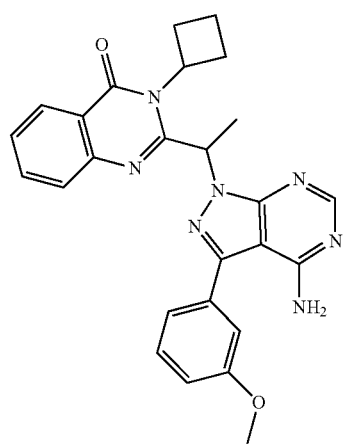 [SMILES: COc1cccc(-c2nn(C(C)c3nc4ccccc4c(=O)n3C3CCC3)c3ncnc(N)c23)c1]

The synthesis of the compound of Example 71 was completed by using procedures similar to those described in Example 1. MS(ESI) m/z(M+1)+: 468.21.

Example 72: 2-(1-(4-amino-3-(3-hydroxyphenyl)-1H-pyrazolo [3,4-d]pyrimidin-1-yl)ethyl)-3-cyclobutylquinazolin-4(3H)-one

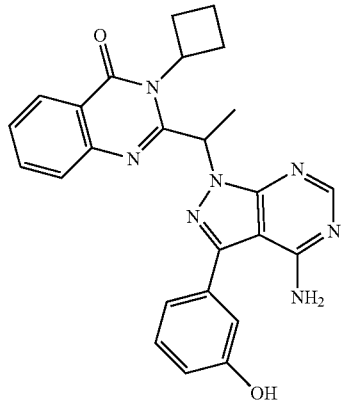 [SMILES: CC(c1nc2ccccc2c(=O)n1C1CCC1)n1nc(-c2cccc(O)c2)c2c(N)ncnc21]

The synthesis of the compound of Example 72 was completed by using procedures similar to those described in Example 1. MS(ESI) m/z(M+1)+: 454.20.

Example 73: 2-(1-(4-amino-3-(3-methoxyphenyl)-1H-pyrazolo [3,4-d]pyrimidin-1-yl)ethyl)-3-cyclobutyl-5-fluoroquinazolin-4(3H)-one

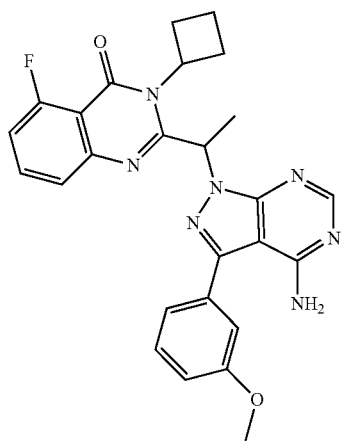 [SMILES: COc1cccc(-c2nn(C(C)c3nc4cccc(F)c4c(=O)n3C3CCC3)c3ncnc(N)c23)c1]

The synthesis of the compound of Example 73 was completed by using procedures similar to those described in Example 1. MS(ESI) m/z(M+1)+: 486.20.

Example 74: 2-(1-(4-amino-3-(3-hydroxyphenyl)-1H-pyrazolo [3,4-d]pyrimidin-1-yl)ethyl)-3-cyclobutyl-5-fluoroquinazolin-4(3H)-one

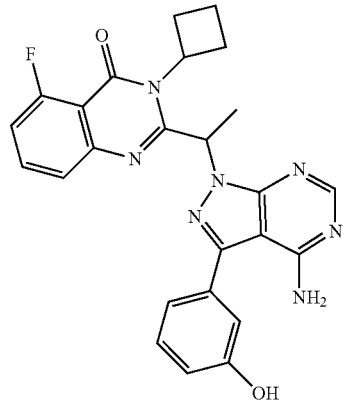 [SMILES: CC(c1nc2cccc(F)c2c(=O)n1C1CCC1)n1nc(-c2cccc(O)c2)c2c(N)ncnc21]

The synthesis of the compound of Example 74 was completed by using procedures similar to those described in Example 1. MS(ESI) m/z(M+1)+: 472.19.

Example 75: 2-(1-(4-amino-3-(3-hydroxyphenyl)-1H-pyrazolo[3,4-d]pyrimidin-1-yl)ethyl)-3-cyclopropyl-6-fluoroquinazolin-4(3H)-one

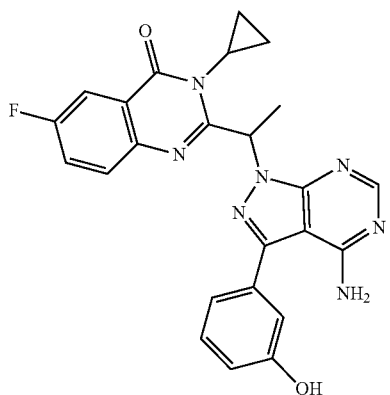 [SMILES: CC(c1nc2ccc(F)cc2c(=O)n1C1CC1)n1nc(-c2cccc(O)c2)c2c(N)ncnc21]

The synthesis of the compound of Example 75 was completed by using procedures similar to those described in Example 1. MS(ESI) m/z(M+1)+: 458.17.

Example 76: 2-(1-(4-amino-3-(3-methoxyphenyl)-1H-pyrazolo [3,4-d]pyrimidin-1-yl)ethyl)-3-cyclopropyl-6-fluoroquinazolin-4(3H)-one

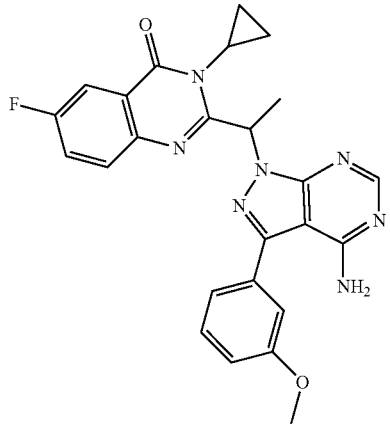 [SMILES: COc1cccc(-c2nn(C(C)c3nc4ccc(F)cc4c(=O)n3C3CC3)c3ncnc(N)c23)c1]

The synthesis of the compound of Example 76 was completed by using procedures similar to those described in Example 1. MS(ESI) m/z(M+1)+: 472.19.

Example 77: 2-(1-(4-amino-3-(3-hydroxyphenyl)-1H-pyrazolo [3,4-d]pyrimidin-1-yl)ethyl)-3-cyclopropylquinazolin-4(3H)-one

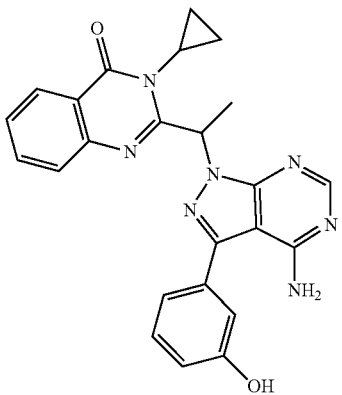 [SMILES: CC(c1nc2ccccc2c(=O)n1C1CC1)n1nc(-c2cccc(O)c2)c2c(N)ncnc21]

The synthesis of the compound of Example 77 was completed by using procedures similar to those described in Example 1. MS(ESI) m/z(M+1)+: 440.18.

Example 78: 2-(1-(4-amino-3-(3-methoxyphenyl)-1H-pyrazolo [3,4-d]pyrimidin-1-yl)ethyl)-3-cyclopropylquinazolin-4(3H)-one

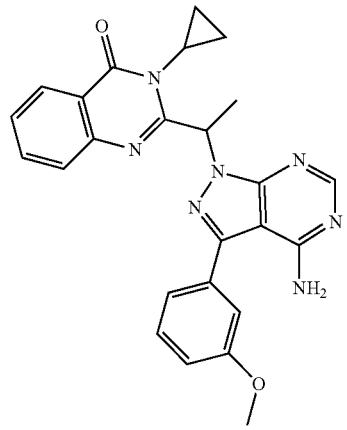 [SMILES: COc1cccc(-c2nn(C(C)c3nc4ccccc4c(=O)n3C3CC3)c3ncnc(N)c23)c1]

The synthesis of the compound of Example 78 was completed by using procedures similar to those described in Example 1. MS(ESI) m/z(M+1)+: 454.20.

Example 79: 2-((S)-1-(4-amino-3-(3-fluoro-4-methoxyphenyl)-1H-pyrazolo[3,4-d]pyrimidin-1-yl)ethyl)-3-cyclobutyl-5-fluoroquinazolin-4(3H)-one

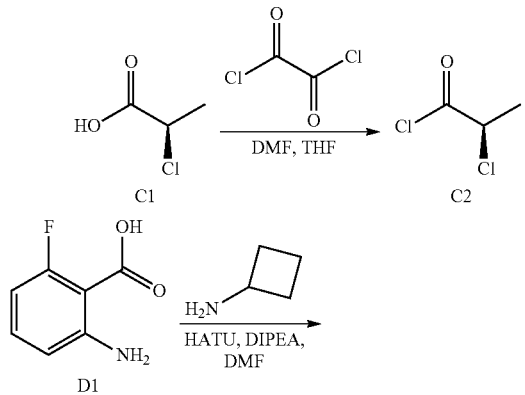

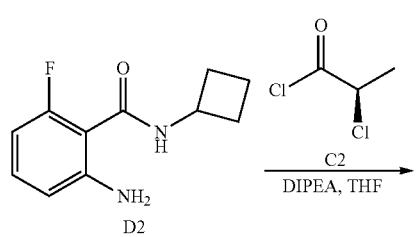

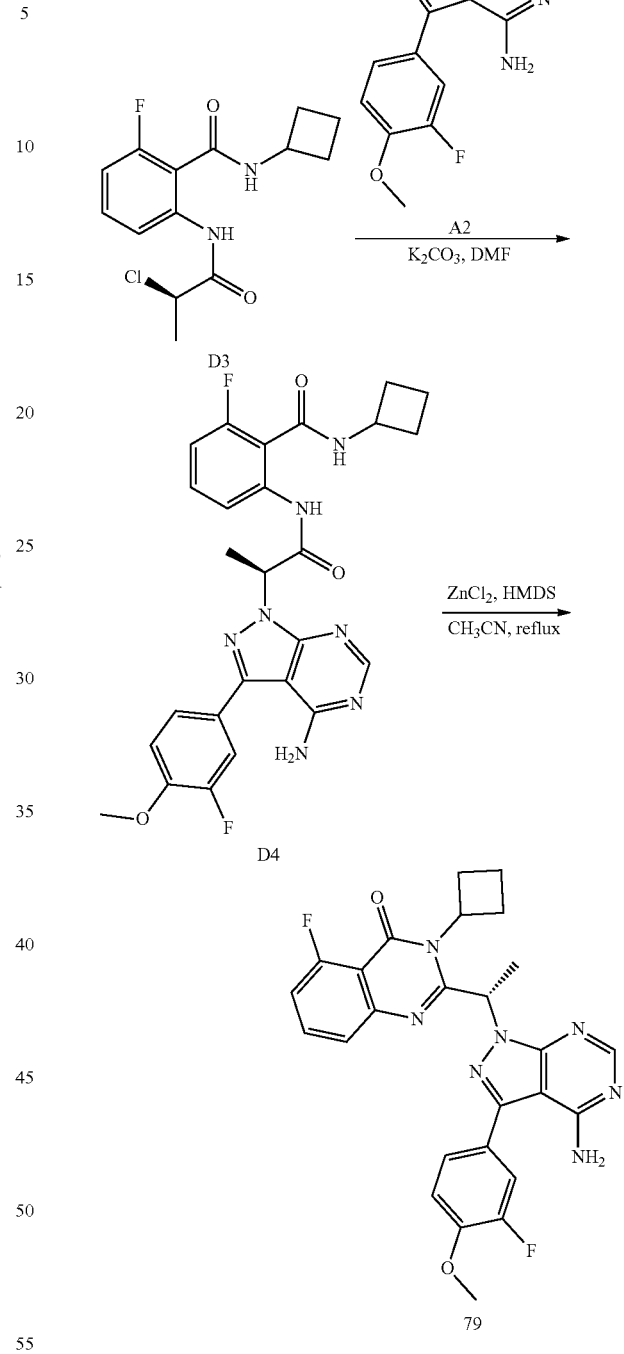

(R)-2-Chloropropionyl chloride (C2): (R)-2-chloropropionic acid (1.5 g) was added in a round bottom flask, followed by addition of tetrahydrofuran (20 ml), and N,N-dimethylformamide (0.5 ml). The system was cooled to 0° C. with an ice-water bath, and then oxalyl chloride (1.4 ml) was slowly added thereto. The reaction system was stirred at 0° C. for one hour, then returned to room temperature, and was allowed for reaction for another 14 hours. After the reaction, the system was evaporated to dry the solvent under reduced pressure to obtain a crude oil C2. LC/MS: M+H 126.97.

2-Amino-N-cyclobutyl-6-fluorobenzamide (D2): 2-amino-6-fluorobenzoic acid (1.0 g) was added in a round bottom flask, followed by addition of tetrahydrofuran (20 ml), N,N-diisopropyl ethylamine (2.3 ml), HATU (2.9 g) and cyclobutylamine (0.66 ml). The system was then cooled to 0° C. with an ice-water bath. The reaction system was stirred at 0° C. for one hour, then returned to room temperature, and was allowed for reaction for another 12 hours. After the reaction, the system was evaporated to dry the solvent under reduced pressure, and the resultant was diluted with water and extracted with ethyl acetate. The organic phase was washed with water and saturated brine, respectively, and dried with anhydrous sodium sulfate. The organic phase was filtered and evaporated to dryness under reduced pressure to obtain a crude product. The crude product was purified by pressurized silica gel column chromatography to obtain compound D2. LC/MS: M+H 209.11.

(R)-2-(2-Chloropropionamido)-N-cyclobutyl-6-fluorobenzamide (D3): 2-amino-N-cyclobutyl-6-fluorobenzamide (1.3 g) was added in a round bottom flask, followed by addition of tetrahydrofuran (30 ml) and N,N-diisopropyl ethylamine (3.4 ml). The system was then cooled to 0° C. with an ice-water bath, and (R)-2-chloropropionyl chloride (0.88 g) was slowly added thereto. The reaction system was stirred at 0° C. for one hour, then returned to room temperature, and was allowed for reaction for another 12 hours. After the reaction, the system was evaporated to dry the solvent under reduced pressure, and the resultant was diluted with water and extracted with ethyl acetate. The organic phase was washed with water and saturated brine, respectively, and dried with anhydrous sodium sulfate. The organic phase was filtered and evaporated to dryness under reduced pressure to obtain a crude product. The crude product was purified by pressurized silica gel column chromatography to obtain compound D3. LC/MS: M+H 299.09.

2-((S)-2-(4-amino-3-(3-fluoro-4-methoxyphenyl)-1H-pyrazolo[3,4-d]pyrimidin-1-yl)propionamido)-N-cyclobutyl-6-fluorobenzamide (D4): (R)-2-(2-chloropropionamido)-N-cyclobutyl-6-fluorobenzamide (100 mg) was added in a round bottom flask, followed by addition of N,N-dimethylformamide (2 ml), 3-(3-fluoro-4-methoxyphenyl)-1H-pyrazolo[3,4-d]pyrimidin-4-amine (174 mg) and potassium carbonate (93 mg). The reaction system was allowed for reaction at room temperature for 8 hours under the protection of argon. After the reaction, the system was evaporated to dry the solvent under reduced pressure, and the resultant was diluted with water and extracted with dichloromethane. The organic phase was washed with water and saturated brine, respectively, and dried with anhydrous sodium sulfate. The organic phase was filtered and evaporated to dryness under reduced pressure to obtain a crude product. The crude product was purified by pressurized silica gel column chromatography to obtain compound D4. LC/MS: M+H 522.20.

2-((S)-1-(4-amino-3-(3-fluoro-4-methoxyphenyl)-1H-pyrazolo[3,4-d]pyrimidin-1-yl)ethyl)-3-cyclobutyl-5-fluoroquinazolin-4(3H)-one(79): 2-((S)-2-(4-amino-3-(3-fluoro-4-methoxyphenyl)-1H-pyrazolo[3,4-d]pyrimidin-1-yl)propionamido)-N-cyclobutyl-6-fluorobenzamide (100 mg) was added in a round bottom flask, followed by addition of acetonitrile (2 ml), zinc chloride (102 mg) and hexamethyldisilazane (132 µl). The reaction system was allowed for reaction under reflux for 8 hours under the protection of argon. After the reaction, the system was evaporated to dry the solvent under reduced pressure, and the resultant was diluted with water and extracted with dichloromethane. The organic phase was washed with water and saturated brine, respectively, and dried with anhydrous sodium sulfate. The organic phase was filtered and evaporated to dryness under reduced pressure to obtain a crude product. The crude product was purified by pressurized silica gel column chromatography to obtain compound 79. LC/MS: M+H 504.19.

Example 80: 2-((R)-1-(4-amino-3-(3-fluoro-4-methoxyphenyl)-1H-pyrazolo[3,4-d]pyrimidin-1-yl)ethyl)-3-cyclobutyl-5-fluoroquinazolin-4(3H)-one

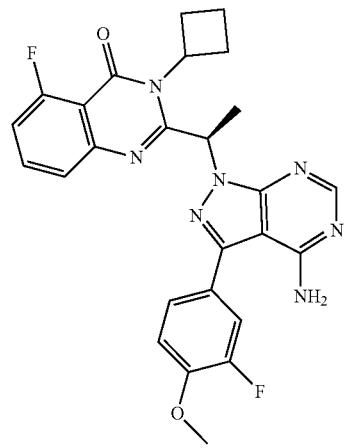 [SMILES: COc1ccc(-c2nn([C@H](C)c3nc4cccc(F)c4c(=O)n3C3CCC3)c3ncnc(N)c23)cc1F]

The synthesis of the compound of Example 80 was completed by using procedures similar to those described in Example 79. MS(ESI) m/z(M+1)+: 504.19.

Example 81: 2-((S)-1-(4-amino-3-(3-fluoro-4-methoxyphenyl)-1H-pyrazolo [3,4-d]pyrimidin-1-yl)propyl)-3-cyclopropyl-5-fluoroquinazolin-4(3H)-one

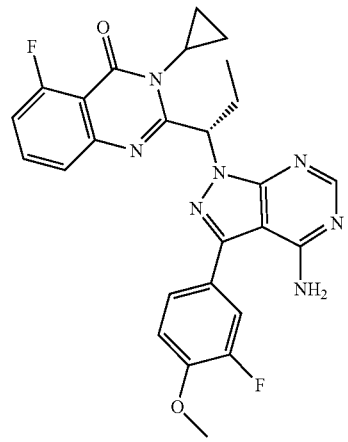 [SMILES: CC[C@@H](c1nc2cccc(F)c2c(=O)n1C1CC1)n1nc(-c2ccc(OC)c(F)c2)c2c(N)ncnc21]

The synthesis of the compound of Example 81 was completed by using procedures similar to those described in Example 79. MS(ESI) m/z(M+1)+: 504.19.

Example 82: 2-((R)-1-(4-amino-3-(3-fluoro-4-methoxyphenyl)-1H-pyrazolo [3,4-d]pyrimidin-1-yl)propyl)-3-cyclopropyl-5-fluoroquinazolin-4(3H)-one

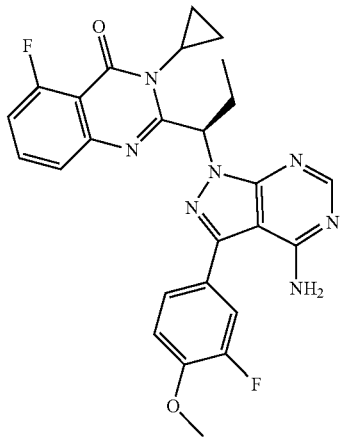 [SMILES: CC[C@H](c1nc2cccc(F)c2c(=O)n1C1CC1)n1nc(-c2ccc(OC)c(F)c2)c2c(N)ncnc21]

The synthesis of the compound of Example 82 was completed by using procedures similar to those described in Example 79. MS(ESI) m/z(M+1)+: 504.19.

Example 83: In Vitro Test of Inhibitory Activity (Enzyme Activity)

In vitro enzyme activity experiments were performed to determine the $IC_{50}$ values of the compounds against PI3K family type I kinases (PI3Kα, PI3Kβ, PI3Kγ, PI3Kδ) and type II kinases (PIK3C2A, PIK3C2B). Protein kinases PI3Kα, PI3Kγ, PI3Kδ, PIK3C2A, and PIK3C2B were all purchased from Invitrogen (US); protein kinase PI3Kβ was purchased from sigma (US); the three substrates PIP2: PS, PI and PI: PS were purchased from Invitrogen (US).

Protein kinases diluted to a certain concentration, i.e., PI3Kα 5.4 μL (with a final concentration of 0.16 ng/μL), PI3Kβ 5.4 μL (with a final concentration of 6 ng/μL), PI3Kδ 5.4 μL (with a final concentration of 1 ng/μL), PI3Kγ 5.4 μL (with a final concentration of 5 ng/μL), PIK3C2A 5.4 μL (with a final concentration of 5 ng/μL), and PIK3C2B 5.4 μL (with a final concentration of 10 ng/μL) were respectively reacted with 1 μL of the serially diluted drug compounds for 1 hour at room temperature (final drug concentrations were 10 μM, 1 μM, 0.3 μM, 0.1 μM, 0.03 μM, 0.01 μM, 0.003 μM, and 0.001 μM, respectively).

To each reaction tube of the above PI3K family type I kinases, 6 μL of a mixture of ATP (Promega, US) and substrate PIP2:PS (final concentrations of ATP in the reaction systems of kinases PI3Kα, and PI3Kβ were 10 μM, and final concentrations of ATP in the reaction systems of kinases PI3Kδ, and PI3Kγ were 50 μM, and final concentrations of the substrate PIP2:PS were all 50 μM) was added, and reacted at 37° C. for 1 hour. The reaction buffer was 50 mM Hepes (pH 7.5) (Promega, USA), 3 mM $MgCl_2$, 1 mM EGTA (Promega, US), 100 mM NaCl, 0.03% CHAPS (Promega, US).

To each reaction tube of the above PI3K family type II kinases, 6 μL of a mixture of ATP and substrate PI (final concentrations were 50 μM and 100 μM, respectively) was added, and reacted at 37° C. for 1 hour. The reaction buffer was 50 mM Hepes (pH 7.5), 3 mM $MgCl_2$, 1 mM EGTA, 100 mM NaCl, 0.03% CHAPS.

5 μL of kinase solution after reaction was placed in a 384-well plate (Corning, US), and 5 μL of ADP-Glo™ reagent (Promega, US) was added thereto and reacted at room temperature for 40 minutes to stop the kinase reaction and exhaust the remaining ATP; 10 μL of kinase detection reagent was added to convert ADP into ATP, and coupled luciferase/luciferin reaction was utilized to detect the newly synthesized ATP. Envision was utilized for readout and plotting, and Graphpad $IC_{50}$ value was calculated. The experimental results were shown in Table 2 and Table 3.

Experiments have shown that the compound of the invention is a selective inhibitor of PI3Kδ, has strong inhibitory activity against PI3Kδ, and has an excellent selectivity relative to other PI3K family kinases, and particularly has a selectivity of 10-fold or more relative to the inhibitory activity against PI3Kγ, preferably 20-fold or more. PI3Kδ and PI3Kγ are mainly expressed in lymphocytes, while it has been reported that PI3Kγ is also expressed in cardiomyocytes. If PI3Kγ is inhibited at the same time, cardiac function will be affected, and for example the neovascularization in patients with ischaemic heart disease may be affected (Circ Res. 2010 Mar. 5; 106(4): 757-768). Therefore, selectively inhibiting PI3Kδ activity while relatively lowly inhibiting PI3Kγ or without inhibiting PI3Kγ has clinical significance. Compared with the control compound TGR1202 (MedChemExpress, China), the activity of the compound of the invention was improved by 14-fold and the selectivity relative to PI3Kγ was improved by 38-fold.

TABLE 2

| No. | PI3Kα/nM | PI3Kβ/nM | PI3Kγ/nM | PI3Kδ/nM |
|---|---|---|---|---|
| Compound 1 | 7409 | 2955 | 4093 | 27.4 |
| Compound 5 | 5524 | >10000 | 1719 | 18.6 |
| Compound 6 | 1688 | 523.1 | 298.7 | 31 |
| Compound 7 | | | | 99.93 |
| Compound 8 | 1718 | 1303 | 147.9 | 14 |
| Compound 9 | 3354 | 1159 | 685.4 | 17.3 |
| Compound 10 | | | 122 | 102.8 | 6.4 |
| Compound 11 | | | 270 | 389 | 18.3 |
| Compound 12 | | | | 82 |
| Compound 14 | | >10000 | >10000 | 31.9 |
| Compound 19 | | | 547.4 | 688.7 | 37.9 |
| Compound 22 | 1687 | 344.2 | 485 | 4.1 |
| Compound 23 | 6444 | 998.7 | 922 | 9.5 |
| Compound 24 | | | | 21.53 |
| Compound 25 | | | | 17.5 |
| Compound 26 | | | | 55.7 |
| Compound 27 | 1097 | | 433.7 | 10.3 |
| Compound 28 | | | | 83.27 |
| Compound 29 | | | | 77.32 |
| Compound 34 | | | | 41.79 |
| Compound 35 | | | | 26.19 |
| Compound 36 | | | | 16.23 |
| Compound 37 | 4211 | 3278 | 753.2 | 1 |
| Compound 38 | 2233 | 581.4 | 261.5 | 9.59 |
| Compound 39 | | | | 23.49 |
| Compound 40 | | | | 28.9 |
| Compound 42 | 3770 | 690.1 | 575.9 | 8.3 |
| Compound 43 | | | | 27.3 |
| Compound 44 | | | | 39.8 |
| Compound 45 | | | | 27.2 |
| Compound 46 | | | | 34.7 |
| Compound 47 | | | | 32.1 |
| Compound 50 | | | | 48.5 |
| Compound 53 | | | | 43.77 |
| Compound 54 | | | | 38.97 |
| Compound 56 | | | | 56.73 |
| Compound 81 | | 790 | 470.5 | 16.4 |
| Compound 82 | | | | 36.7 |

TABLE 3

| IC50/nM | PIK3α | PIK3β | PIK3δ | PIK3γ | PI3KC2A | PI3KC2B |
|---|---|---|---|---|---|---|
| Compound 9 | 3354 | 1159 | 17.3 | 685.4 | >10000 | 9961 |
| TGR1202 | | >10000 | 260 | 362 | | |

Example 84: Test of the Efficacy in Rat Model of Rheumatoid Arthritis

In this example, the experimental results of Compound 9 were tested in a rat model of adjuvant arthritis.

The experimental procedures were illustrated as follows:

(1) Sprague-Dawley (SD) rats, female, weighing 180 g±20 g, were purchased from Beijing Vital River Laboratory Animal Technology Co., Ltd. and maintained in an SPL laboratory. Drinking water and litter were sterilized by autoclaving, and all operations related to the rats were performed under sterile conditions.

(2) In the vehicle group and the treatment group, 10.0 mg/ml CFA (complete Freund's adjuvant, purchased from Sigma, US) was mixed thoroughly, and 0.1 ml of the CFA was injected intracutaneously into the right rear vola pedis of each rat on day 0 to induce inflammation; the normal group was injected with saline in the same way.

(3) Body weight and paw swelling were measured every 3 or 4 days after modeling. Depending on the paw swelling, the systemic inflammation became evident on the 20th day, and thereafter the successfully modeled female SD rats were randomly divided into 2 groups, 5 mice in each group, namely the vehicle group (0.5% methyl cellulose solution, 0.05 ml/kg/day, purchased from Sinopharml, China) and the treatment group of compound 9 (at a dose of 25 mg/kg/day); the 5 rats in the normal group were each given normal saline (0.05 ml/kg/day). The groups were each administrated by oral gavage, once a day, for 14 days.

(4) The body weight and paw swelling were measured every two days after administration, and the paw swelling was measured with a paw swelling meter. Before inflammation, a foot volume meter was used to measure the volume of left rear foot of each rat (non-inflammation side). After the inflammation, the volume of left rear foot was measured to obtain the swelling degree of the secondary paw (Δm1=|paw volume after injection−paw volume before injection|).

Figure 1B:
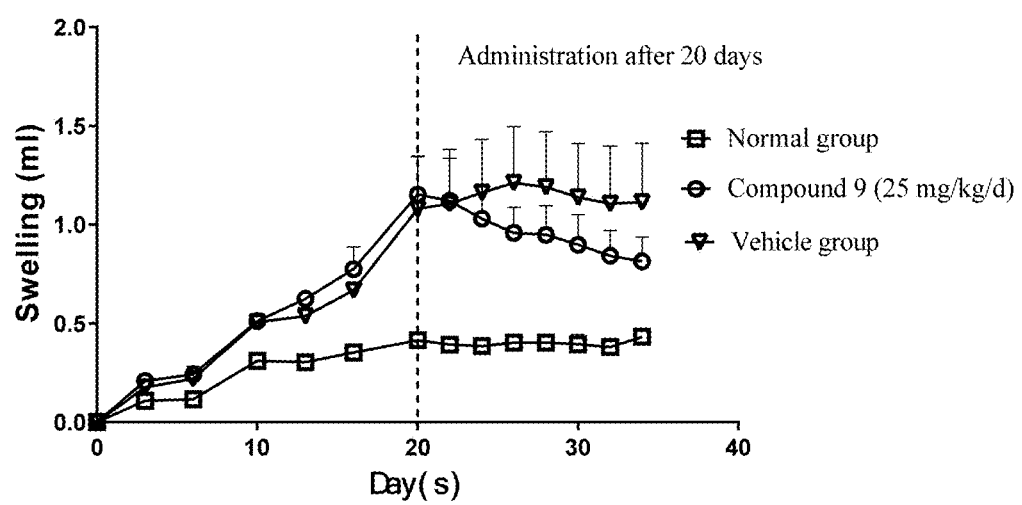
FIG. 1b shows the effect of Compound 9 of the invention, vehicle, and physiological saline on swelling of rat paws after administration.

The experimental results were shown in FIGS. 1a and 1b. Compound 9 had no significant effect on the body weight of rats in the rat model of adjuvant arthritis, as shown in FIG. 1a. The paw swelling of the rats after 14 days of administration of Compound 9 was significantly reduced as compared with the vehicle group, indicating that the compound of the invention has a therapeutic effect on rheumatoid arthritis.

Industrial Applicability

The invention provides a selective PI3Kδ kinase inhibitor, which can be used to inhibit PI3Kδ kinase activity, and treat, prevent, or ameliorate diseases, disorders or conditions which are regulated by or affected by PI3Kδ kinase activity or in which PI3Kδ kinase activity is involved. Therefore, the compounds of the invention can be formulated into corresponding medicaments, suitable for industrial applications.

What is claimed is:

1. A kinase inhibitor, comprising a compound of formula (I) or a pharmaceutically acceptable salt or acid thereof:

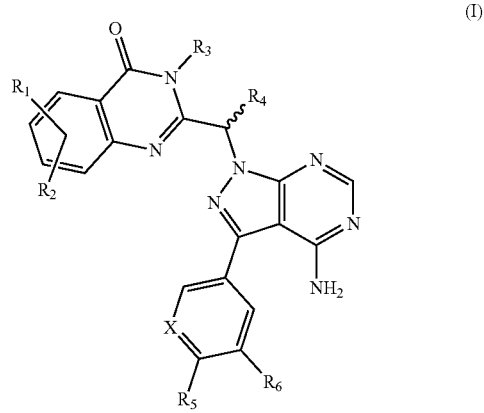

(I)

wherein,

X is selected from the group consisting of CH and N;

$R_1$ and $R_2$ are each independently selected from the group consisting of hydrogen, halogen, and $C_{1-6}$ haloalkyl;

$R_3$ is $C_{3-8}$ cycloalkyl;

$R_4$ is selected from the group consisting of hydrogen and $C_{1-6}$ alkyl;

$R_5$ is selected from the group consisting of hydrogen, $C_{1-6}$ alkyl, $C_{1-6}$ alkoxy, $C_{2-6}$ alkylamido, and $C_{1-6}$ alkylaminoacyl;

$R_6$ is selected from the group consisting of hydrogen, hydroxy, halogen, $C_{1-6}$ alkyl, and $C_{1-6}$ alkoxy;

or $R_5$ and $R_6$ together form a phenyl group or a dioxolane group.

2. The kinase inhibitor of claim 1, wherein X is CH.

3. The kinase inhibitor of claim 1, wherein $R_1$ and $R_2$ are each independently selected from the group consisting of hydrogen, fluorine, and trifluoromethyl.

4. The kinase inhibitor of claim 1, wherein $R_3$ is selected from the group consisting of cyclopropyl, cyclobutyl, cyclopentyl, and cyclohexyl.

5. The kinase inhibitor of claim 1, wherein $R_4$ is selected from the group consisting of hydrogen, methyl, and ethyl.

6. The kinase inhibitor of claim 1, wherein $R_5$ is selected from the group consisting of hydrogen, $C_{1-3}$ alkyl, $C_{1-3}$ alkoxy, $C_{2-3}$ alkylamido, and $C_{1-3}$ alkylaminoacyl.

7. The kinase inhibitor of claim 1, wherein $R_6$ is selected from the group consisting of hydrogen, hydroxy, halogen, $C_{1-3}$ alkyl, and $C_{1-3}$ alkoxy.

8. The kinase inhibitor of claim 1, wherein $R_5$ is methoxy, and $R_6$ is selected from the group consisting of hydrogen, fluorine, and methoxy.

9. The kinase inhibitor of claim 1, wherein the compound of formula (I) is selected from the group consisting of:
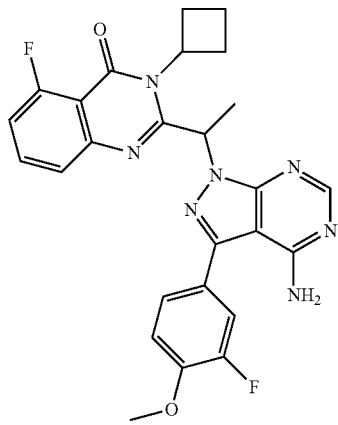
1
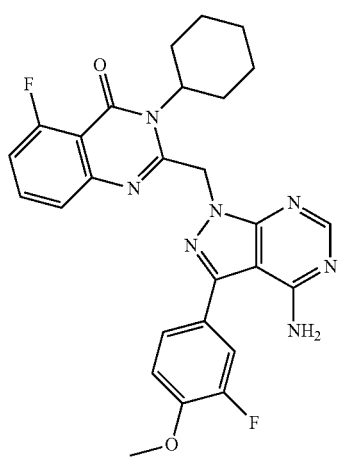
2
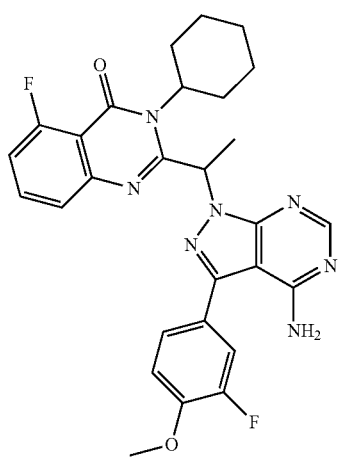
3
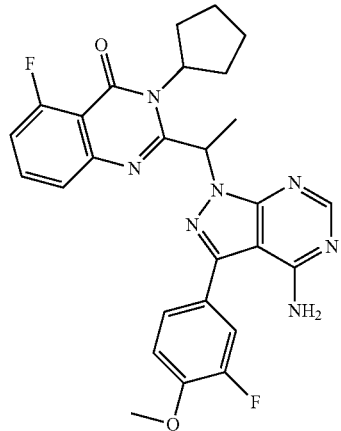
4
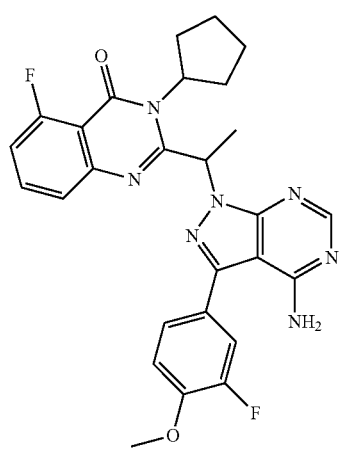
5
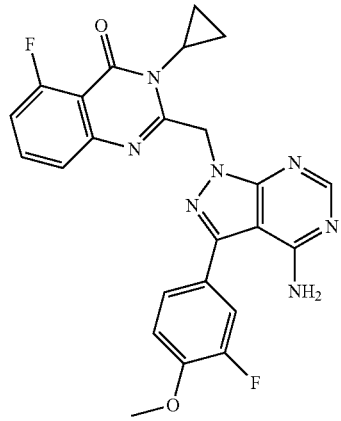
6

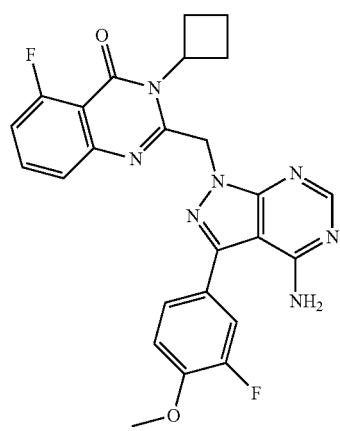
7
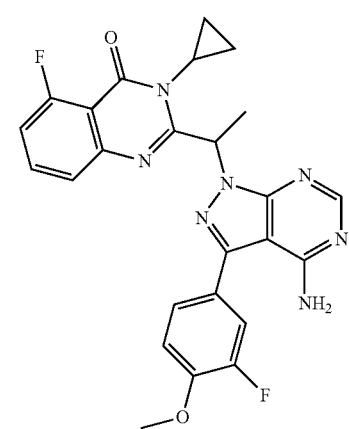
8
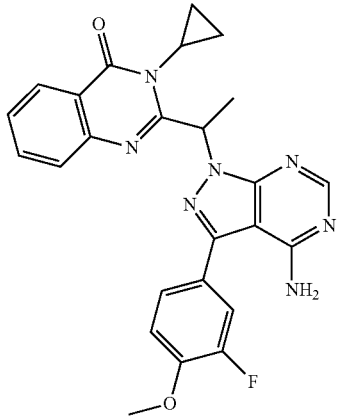
10
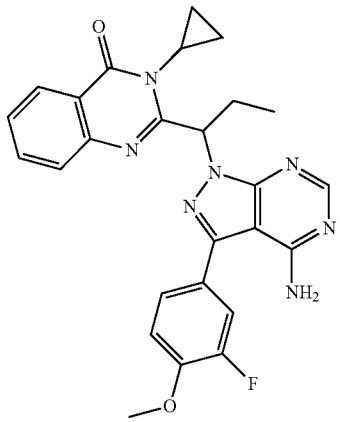
11
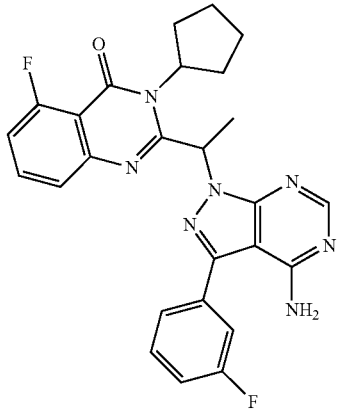
12
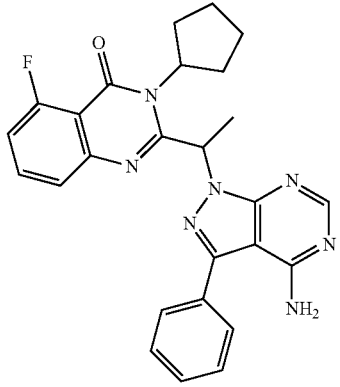
13

14
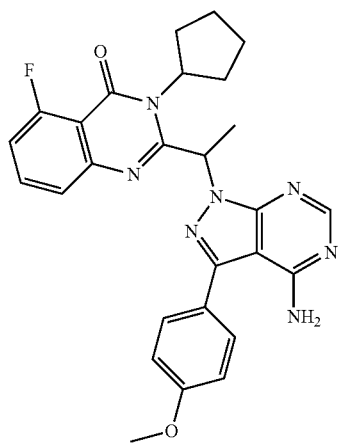
15
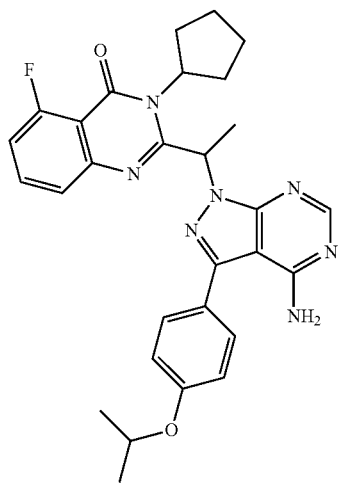
16
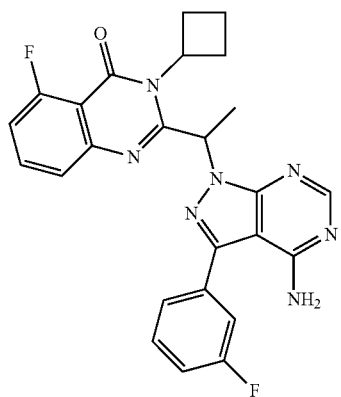
17
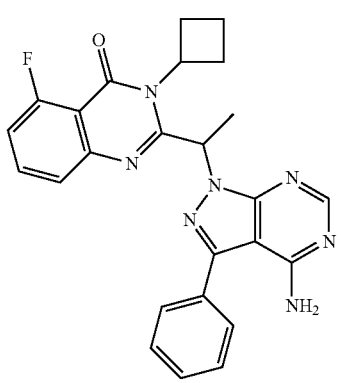
18
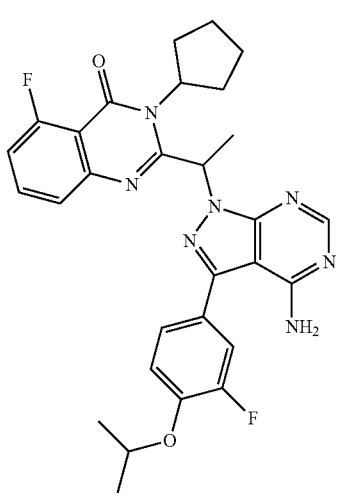
19
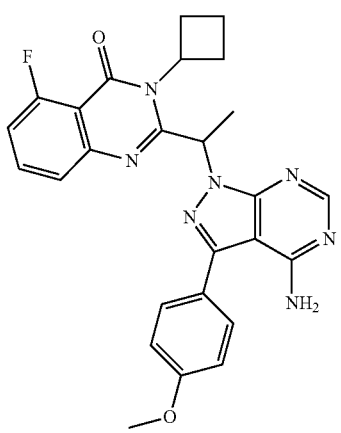

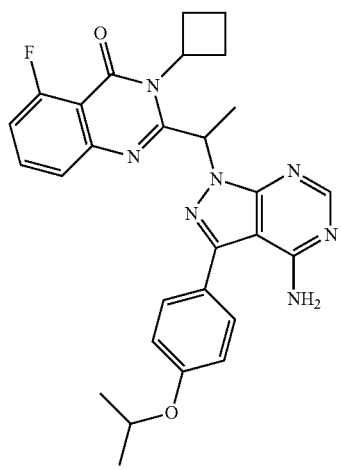
20
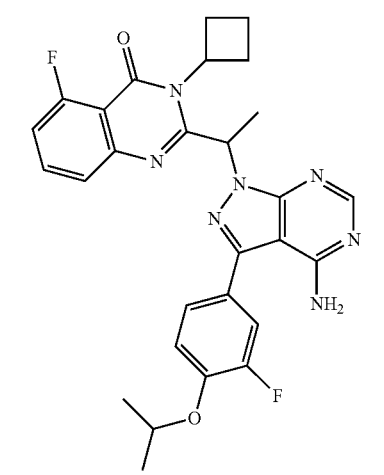
21
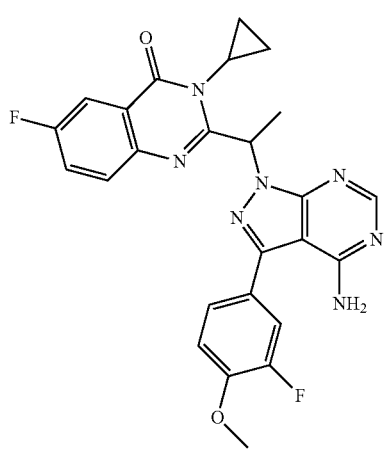
22
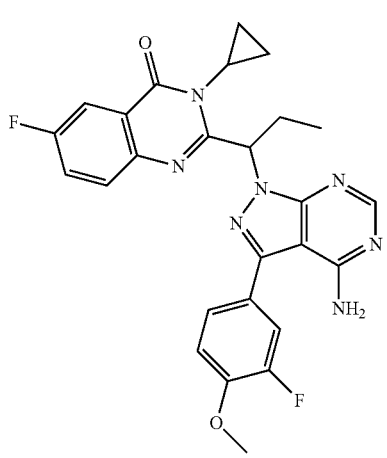
23
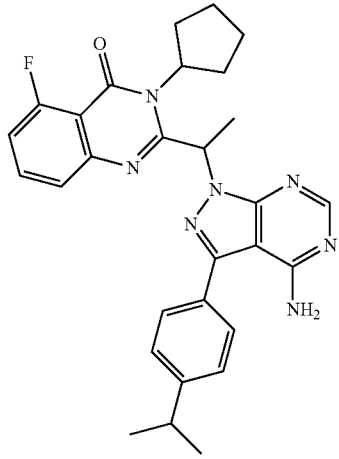
24
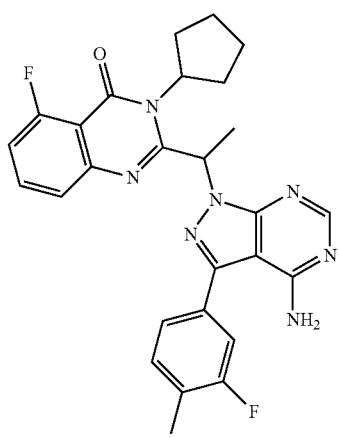
25

26
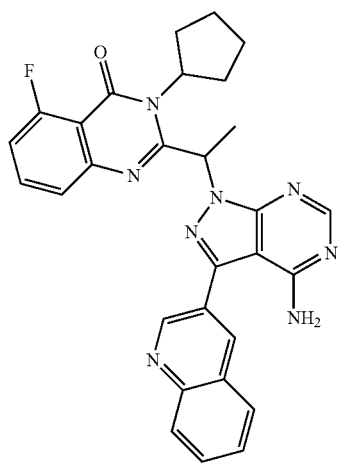
27
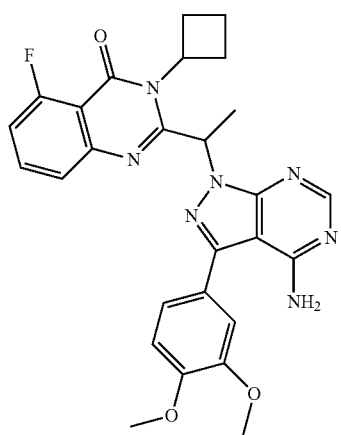
28
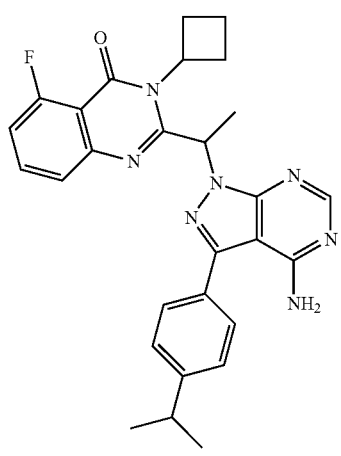
29
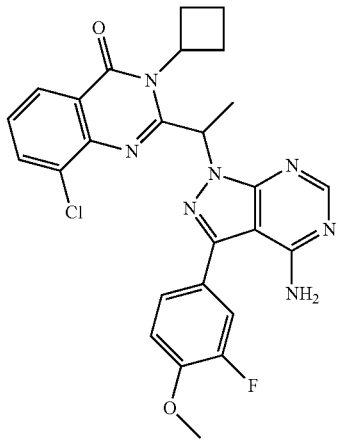
30
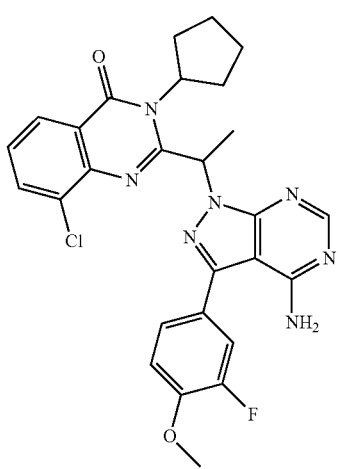
31
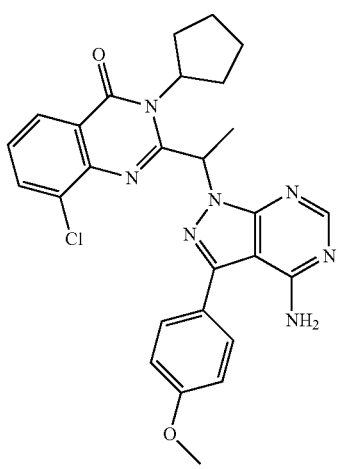

32
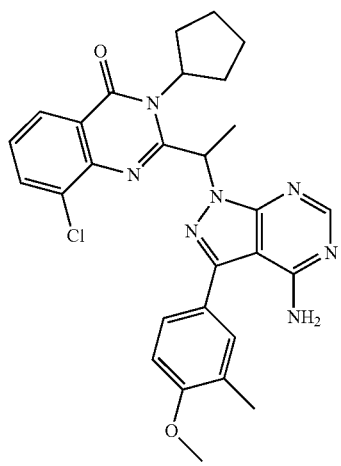
33
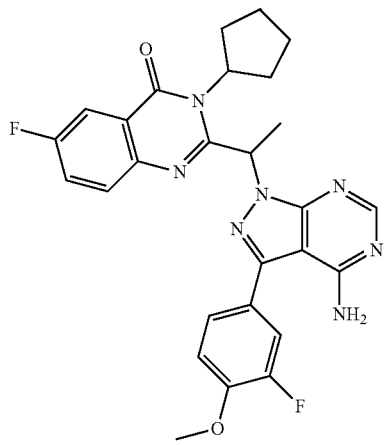
34
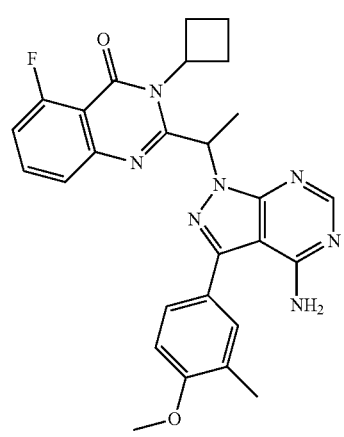
35
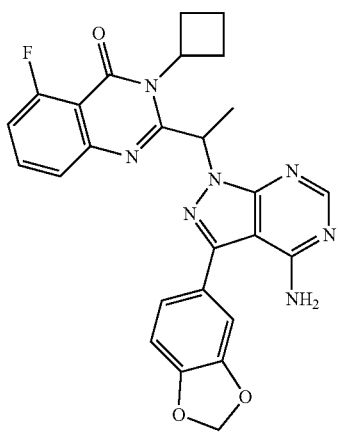
36
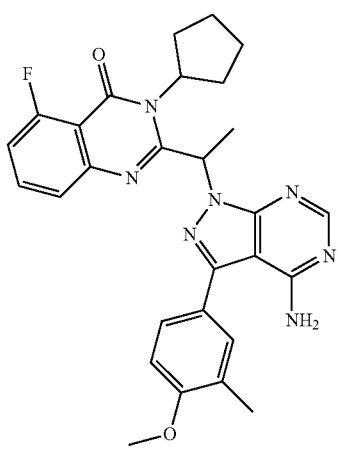
37
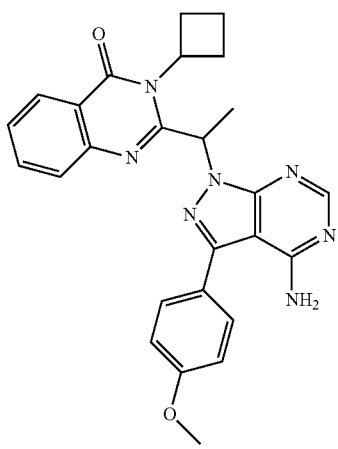

38
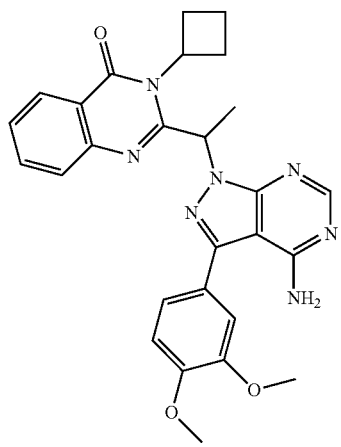
39
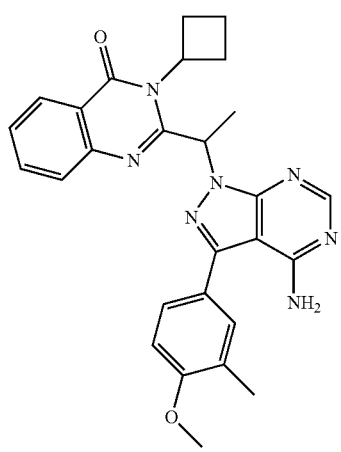
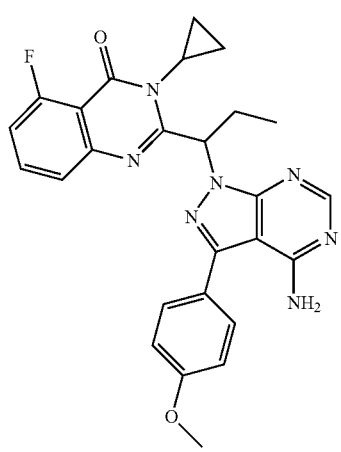
41
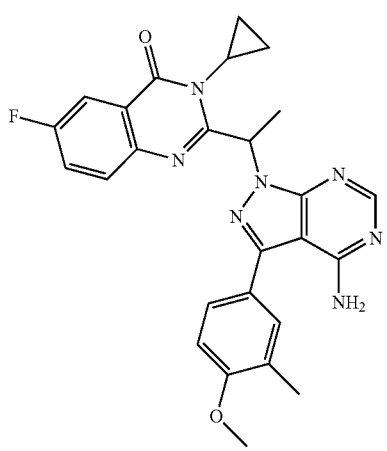
42
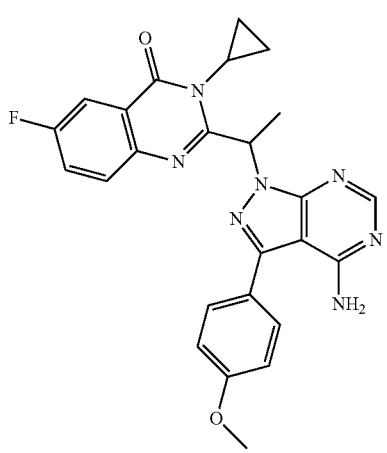
43
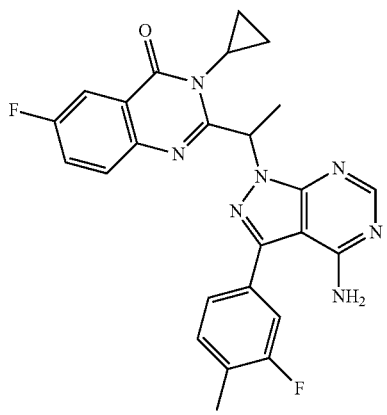

44
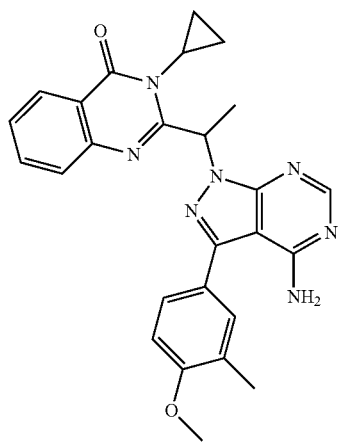
45
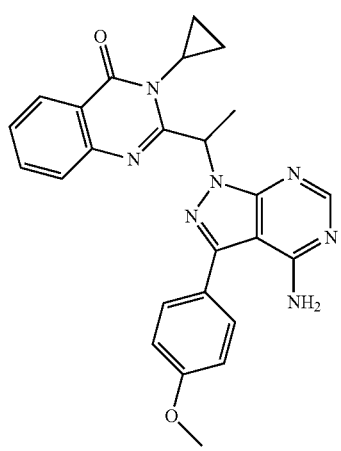
46
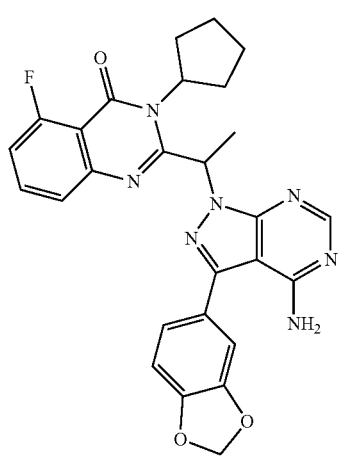
47
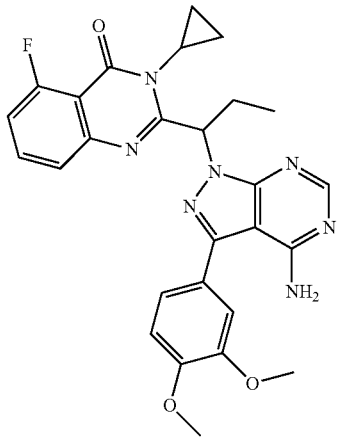
48
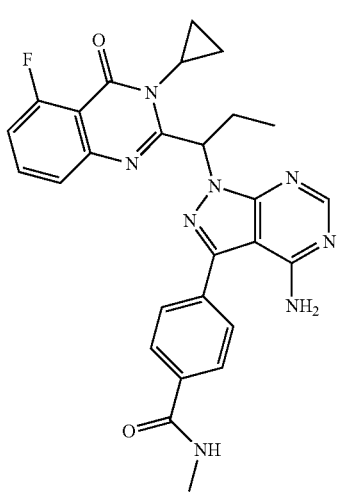
49
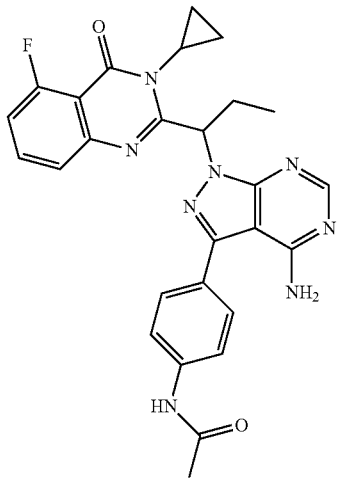

50
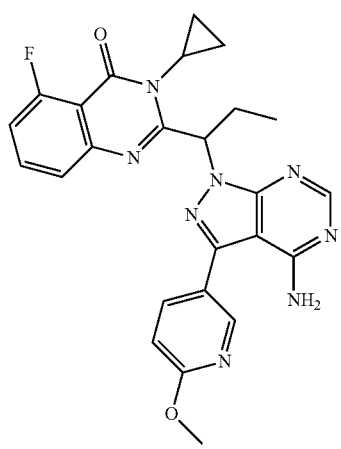
51
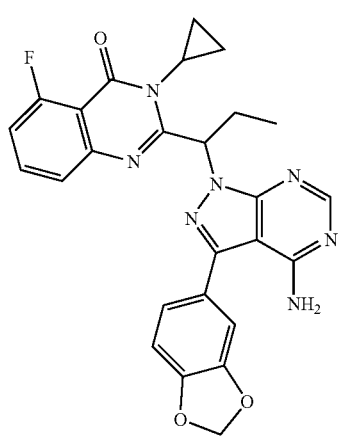
52
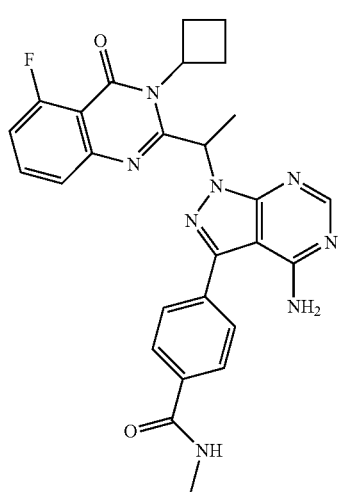
53
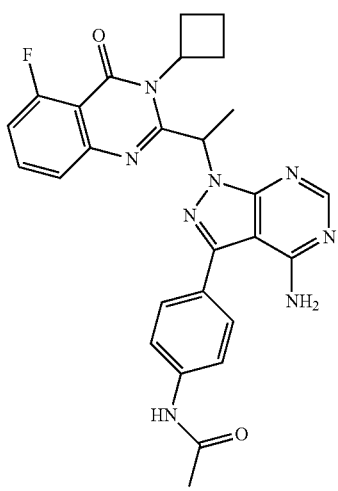
54
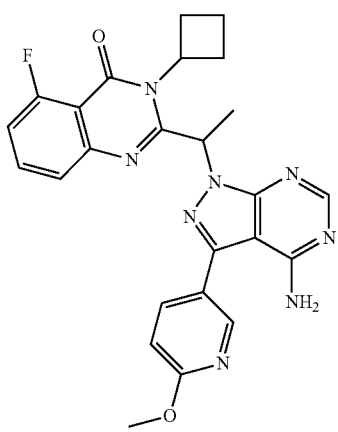
55
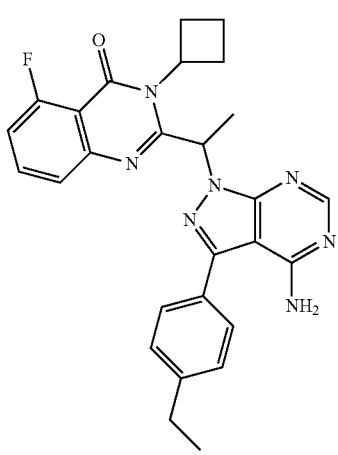

56
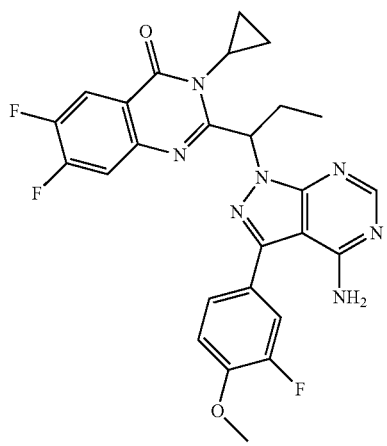
57
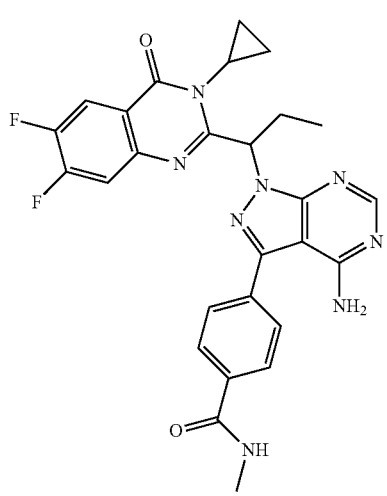
58
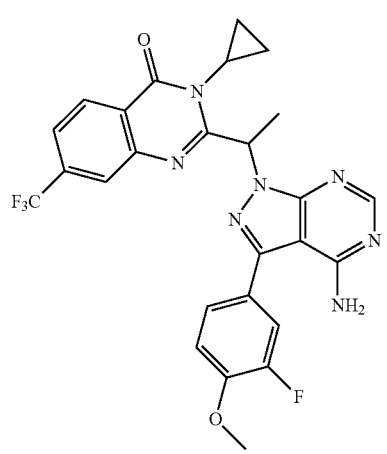
59
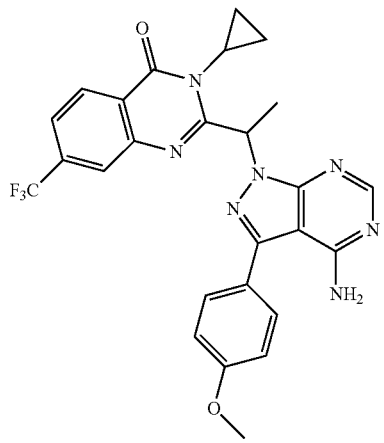
60
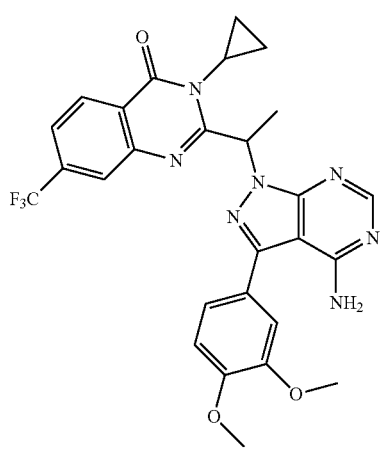
61
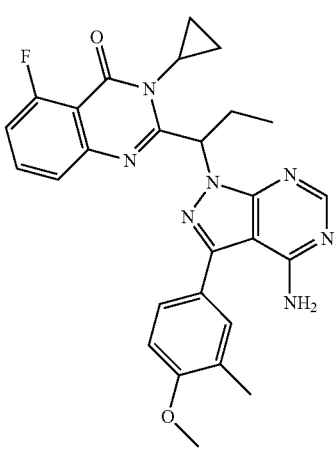

62
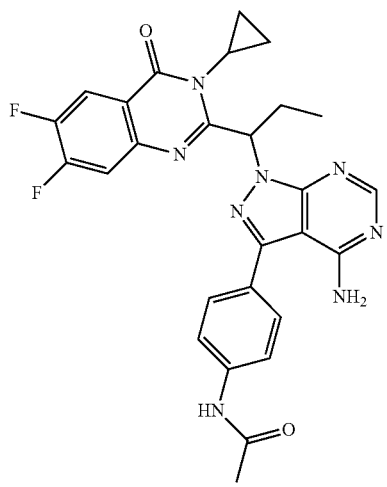
63
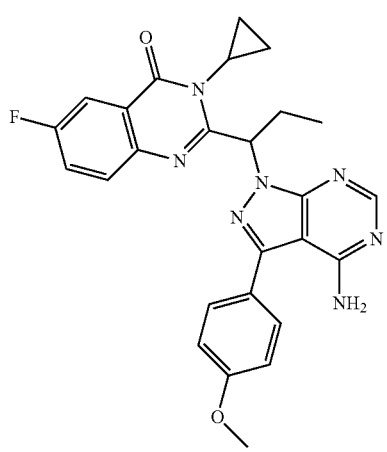
64
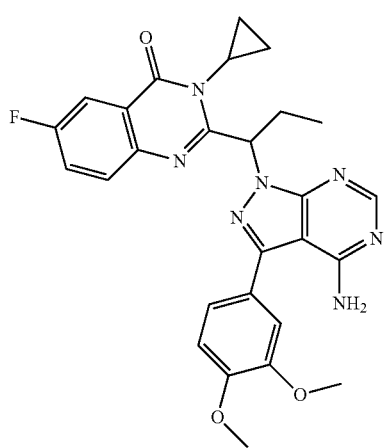
65
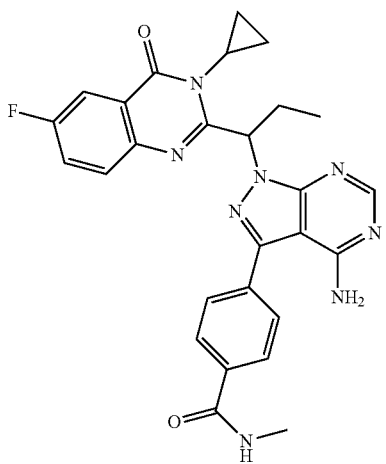
66
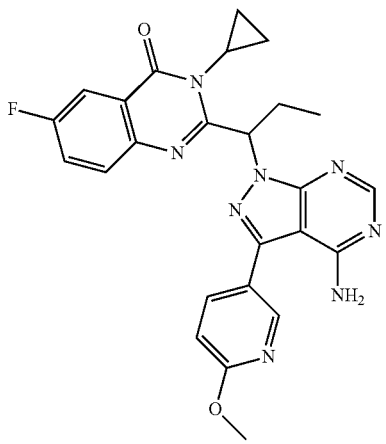
67

68
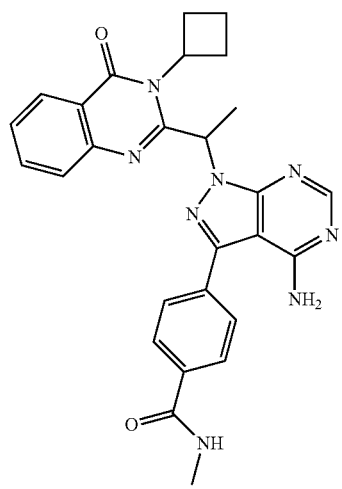
69
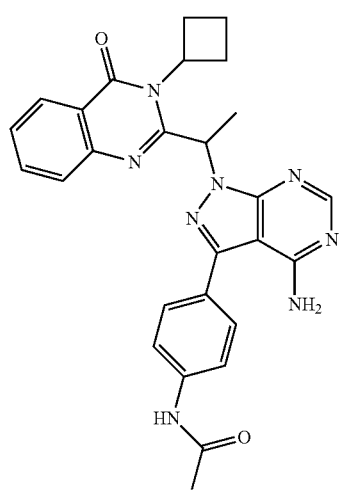
70
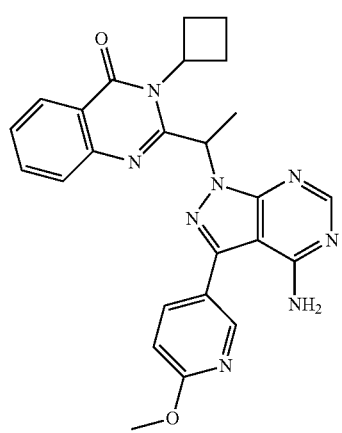
71
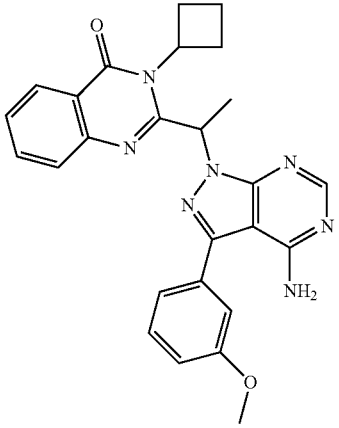
72
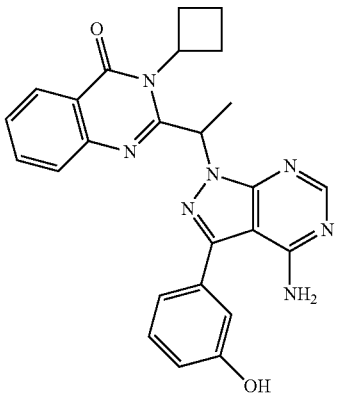
73
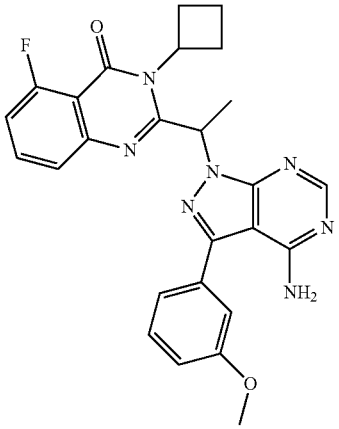
74
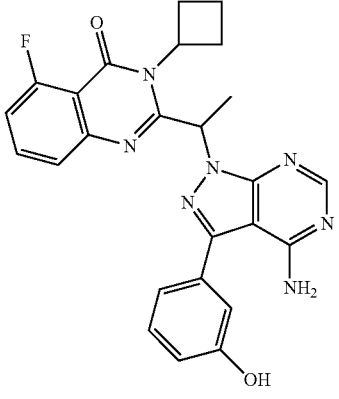

75
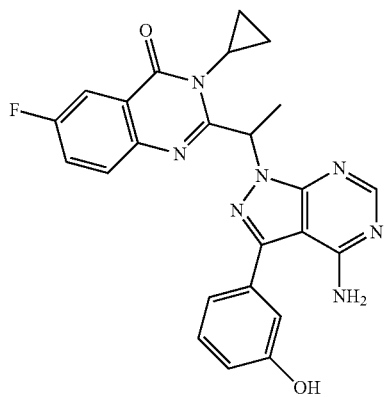
76
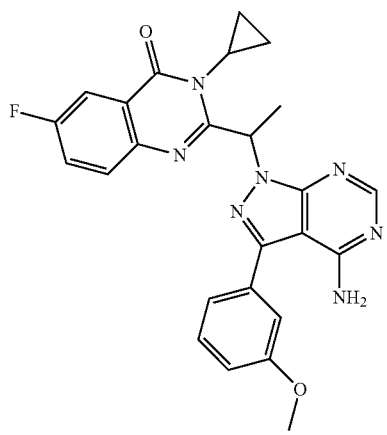
77
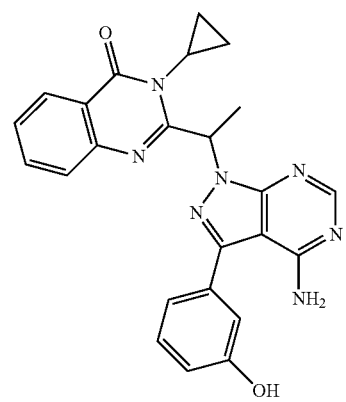
78
79
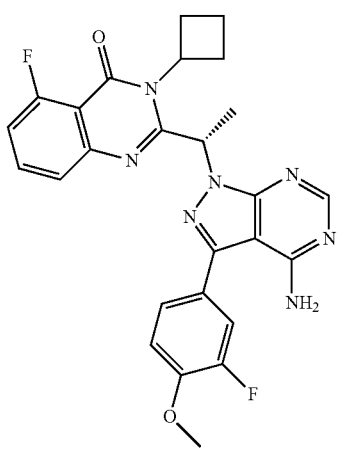
80
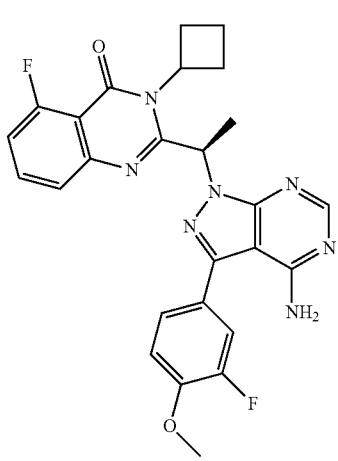
81
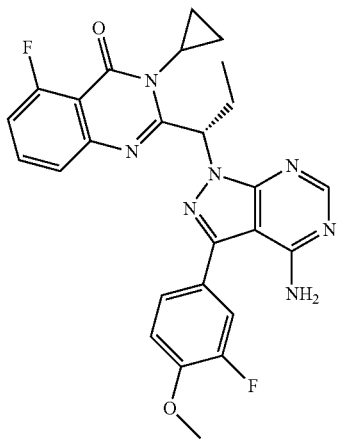

-continued

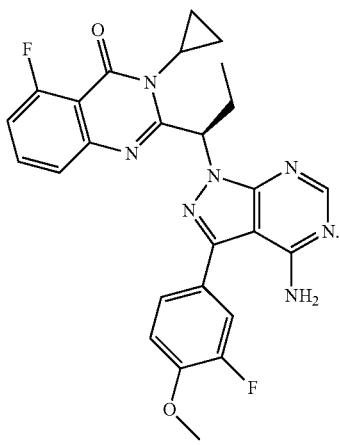

82

10. A pharmaceutical composition, comprising the kinase inhibitor of claim 1, and a pharmaceutically acceptable carrier or excipient.

11. A method for inhibiting PI3K8 tyrosine kinase activity in a subject, comprising administering the kinase inhibitor of claim 1 to the subject.

12. A method for therapeutic treatment of diseases or conditions associated with PI3K8 tyrosine kinase activity in a subject, comprising administering the kinase inhibitor of claim 1 to the subject.

13. The method of claim 12, wherein the diseases or conditions are selected from the group consisting of chronic lymphocytic leukemia, non-Hodgkin's lymphoma, Hodgkin's lymphoma, mantle cell lymphoma, chronic obstructive pulmonary disease, rheumatoid arthritis, systemic lupus erythematosus, and asthma.

* * * * *